United States Patent
Jiang et al.

(10) Patent No.: US 10,376,486 B2
(45) Date of Patent: Aug. 13, 2019

(54) COMPOSITIONS AND METHODS FOR REACTIVATING LATENT VIRAL INFECTIONS

(71) Applicant: The Regents of the University of California, Oakland, CA (US)

(72) Inventors: Guochun Jiang, Davis, CA (US); Satya Dandekar, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/426,437

(22) Filed: Feb. 7, 2017

(65) Prior Publication Data
US 2017/0258750 A1  Sep. 14, 2017

Related U.S. Application Data

(63) Continuation of application No. PCT/US2015/042716, filed on Jul. 29, 2015.
(Continued)

(51) Int. Cl.
*A61K 39/00* (2006.01)
*A61K 31/22* (2006.01)
(Continued)

(52) U.S. Cl.
CPC ............ *A61K 31/22* (2013.01); *A61K 31/167* (2013.01); *A61K 31/496* (2013.01);
(Continued)

(58) Field of Classification Search
None
See application file for complete search history.

(56) References Cited

U.S. PATENT DOCUMENTS 9,387,231 B2 * 7/2016 Finkel ................. A61K 38/191
2003/0166613 A1 9/2003 Aylward et al.
(Continued)

FOREIGN PATENT DOCUMENTS

WO 2014/071109 A1 5/2014
WO 2016/022358 A1 2/2016

OTHER PUBLICATIONS

Warrilow et al., "HIV Type 1 Inhibition by Protein Kinase Modulatory Compounds," AIDS Research and Human Retroviruses, vol. 22, No. 9: 854-864 (Year: 2006).*
(Continued)

*Primary Examiner* — M Franco G Salvoza
(74) *Attorney, Agent, or Firm* — Kilpatrick Townsend & Stockton LLP

(57) ABSTRACT

The present invention provides compositions comprising ingenol-3-angelate (PEP005) and one or more additional latency reactivation agents. The present invention also provides methods for reactivating a latent virus in a subject infected with the virus, the method comprising administering to the subject an effective amount of ingenol-3-angelate (PEP005) alone or in combination with one or more additional latency reactivation agents. In particular embodiments, the combination of compounds advantageously provides a synergistic effect at inducing reactivation of a latent virus such as HIV.

9 Claims, 12 Drawing Sheets

Specification includes a Sequence Listing.

Related U.S. Application Data

(60) Provisional application No. 62/035,333, filed on Aug. 8, 2014.

(51) Int. Cl.
| | |
|---|---|
| *A61K 45/06* | (2006.01) |
| *A61K 31/167* | (2006.01) |
| *A61K 31/496* | (2006.01) |
| *A61K 31/551* | (2006.01) |
| *A61K 39/12* | (2006.01) |

(52) U.S. Cl.
CPC ............ *A61K 31/551* (2013.01); *A61K 39/12* (2013.01); *A61K 45/06* (2013.01)

(56) References Cited

U.S. PATENT DOCUMENTS

| | | |
|---|---|---|
| 2013/0252331 A1 | 9/2013 | Bradner et al. |
| 2014/0079636 A1 | 3/2014 | Chimmanamada et al. |
| 2015/0030638 A1 | 1/2015 | Pianowski et al. |

OTHER PUBLICATIONS

Traylen et al., "Virus reactivation: a panoramic view in human infections," Future Virol. 6(4): 451-463 (Year: 2011).*
Chakravarty, "Viral Infection and Reactivation in Autoimmune Disease," Arthritis & Rheumatism, vol. 58, No. 10: 2949-2957 (Year: 2008).*
Nardis et al., "Latent Virus Reactivation Risk and Biological Drugs: Chronic Inflammatory and Immune-Mediated Disorders," International Journal of Immunopathology and Pharmacology, vol. 26, No. 4: 983-989 (Year: 2013).*
Ersvaer et al., "The Protein Kinase C Agonist PEP005 (Ingenol 3-Angelate) in the Treatment of Human Cancer: A Balance between Efficacy and Toxicity," Toxins 3: 174-194 (Year: 2010).*
Bartholomeuusen et al., "BET bromodomain inhibition activated transcription via a transient release of PTEFb from 7SK snRNP," Journal of Biological Chemistry, vol. 287, No. 43: 36609-36616 (Year: 2012).*
Abreu et al., Dual Role of Novel Ingenol Derivatives From Euphorbia *tirucalli* in HIV Replication: Inhibition of De Novo Infection and Activation of Viral LTR, PLoS One, vol. 9, 2014, p. e97257.
Amatangelo et al., Three-Dimensional Culture Sensitizes Epithelial Ovarian Cancer Cells to EZH2 Methyltransferase Inhibition, Cell Cycle, vol. 12, 2013, pp. 2113-2119.
Archin et al., Administration of Vorinostat Disrupts HIV-1 Latency in Patients on Antiretroviral Therapy, Nature, vol. 487, 2012, pp. 482-485.
Baldwin Jr., Series Introduction: The Transcription Factor NF-κB and Human Disease, The Journal of Clinical Investigation, vol. 107, No. 1, 2001, Jul. 16, 2013, pp. 3-6.
Beans et al., Highly Potent, Synthetically Accessible Prostratin Analogs Induce Latent HIV Expression in Vitro and Ex Vivo, PNAS, vol. 110 No. 29, Jul. 16, 2013, pp. 11698-11703.
Bedoya et al., SJ23B, a jatrophane diterpene activates classical PKCs and displays strong activity against HIV in vitro, Biochem Pharmacol, vol. 77, 2009, pp. 965-978.
Blanco-Molina et al., Ingenol Esters Induce Apoptosis in Jurkat Cells Through an AP-1 and NF-κB Independent Pathway, Chemistry & Biology, vol. 8, 2001, pp. 767-778.
Blazkova et al., CpG Methylation Controls Reactivation of HIV from Latency, PLoS Pathogens, Aug. 2009, vol. 5, Issue 8, e1000554, 14 pages.
Blazkova et al., Effect of Histone Deacetylase Inhibitors on HIV Production in Latently Infected, Resting CD4+ T Cells From Infected Individuals Receiving Effective Antiretroviral Therapy, The Journal of Infectious Diseases, vol. 206, 2012, pp. 765-769.
Bliss, C.I., The Toxicity of Poisons Applied Jointly, Annals of Applied Biology, vol. 26, 1939, pp. 585-615.
Bullen et al, New ex vivo Approaches Distinguish Effective and Ineffective Single Agents for Reversing HIV-1 Latency in vivo, Nat Med, vol. 20, 2014, pp. 425-429.
Chomont et al., HIV Reservoir Size and Persistence are Driven by T Cell Survival and Homeostatic Proliferation, Nature Medicine, vol. 15, 2009, pp. 893-900.
Chou, T., Theoretical Basis, Experimental Design, and Computerized Simulation of Synergism and Antagonism in Drug Combination Studies, Pharmacological Review, vol. 58, No. 3, 2006, pp. 621-681.
Chun et al., Presence of an Inducible HIV-1 Latent Reservoir During Highly Active Antiretroviral Therapy, Proc Natl Acad Sci, vol. 94, 1997, pp. 13193-13197.
Contreras et al., HMBA Releases P-TEFb from HEXIM1 and 7SK snRNA via PI3K/Akt and Activates HIV Transcription, PLoS Pathogens, Oct. 2007, vol. 3, Issue 10, pp. 1459-1469, e146.
Danaher et al., Histone Deacetylase Inhibitors Induce Reactivation of Herpes Simplex Virus Type 1 in a Latency-Associated Transcript (LAT)-Independent Manner in Neuronal Cells, J Neurovirol., Jul. 2005, 11(3), pp. 306-317.
Dechristopher et al., Designed, synthetically accessible bryostatin analogues potently induce activation of latent HIV reservoirs in vitro, Nature Chemistry, vol. 4, Sep. 2012, pp. 705-710.
Don et al., Essential Requirement for Sphingosine Kinase 2 in a Sphingolipid Apoptosis Pathway Activated by FTY720 Analogues, J Biol Chem, vol. 282, 2007, pp. 15833-15842.
Elliott et al., Activation of HIV Transcription with Short-Course Vorinostat in HIV-Infected Patients on Suppressive Antiretroviral Therapy, PLoS Pathog, vol. 10, 2014, p. e1004473.
Emiliani et al., Mutations in the tat Gene Are Responsible for Human Immunodeficiency Virus Type 1 Postintegration Latency in The U1 Cell Line, Journal of Virology, vol. 72, 1998, pp. 1666-1670.
Ferreira et al., Antiproliferative Activity of *Rhinella* Marina and *Rhaebo guttatus* Venom Extracts From Southern Amazon, Toxicon, vol. 72, 2013, pp. 43-51.
Fidler et al., Ingenol Mebutate Gel (Picato): A Novel Agent for the Treatment of Actinic Keratoses, P&T, vol. 39, No. 1, 2014, pp. 40-46.
Finzi et al., Identification of a Reservoir for HIV-1 in Patients on Highly Active Antiretroviral Therapy, Science, vol. 278, 1997, pp. 1295-1300.
Freitas et al., Adipokines, Hormones Related to Body Composition, and Insulin Resistance in HIV Fat Redistribution Syndrome, BMC Infect Dis, vol. 14, 2014, 13 pages.
Friedman et al., Epigenetic Silencing of HIV-1 by the Histone H3 Lysine 27 Methyltransferase Enhancer of Zeste 2, Journal of Virology, vol. 85, No. 17, 2011, pp. 9078-9089.
Giacomet et al., No Cure of HIV Infection in a Child Despite Early Treatment and Apparent Viral Clearance, Lancet, vol. 384, 2014, p. 1320.
Guadalupe et al., Severe CD4+ T-Cell Depletion in Gut Lymphoid Tissue During Primary Human Immunodeficiency Virus Type 1 Infection and Substantial Delay in Restoration Following Highly Active Antiretroviral Therapy, Journal of Virology, vol. 77, No. 21, 2003, pp. 11708-11717.
Guadalupe et al., Viral Suppression and Immune Restoration in the Gastrointestinal Mucosa of Human Immunodeficiency Virus Type 1-Infected Patients Initiating Therapy during Primary or Chronic Infection, Journal of Virology, vol. 80, No. 16, 2006, pp. 8236-8247.
Hamer et al., Rational Design of Drugs That Induce Human Immunodeficiency Virus Replication, Journal of Virology, Oct. 2003, vol. 77, No. 19, pp. 10227-10236.
Hirao et al., Early Mucosal Sensing of SIV Infection by Paneth Cells Induces IL-1β Production and Initiates Gut Epithelial Disruption, PLoS Pathog, vol. 10, Issue 8, 2014, p. e1004311.
Hiscott et al., Hostile takeovers: viral appropriation of the NF-κB pathway, The Journal of Clinical Investigation, Jan. 2001, vol. 107, No. 2, pp. 143-151.
Ho et al., Replication-Competent Noninduced Proviruses in the Latent Reservoir Increase Barrier to HIV-1 Cure, Cell, vol. 155, 2013, pp. 540-551.

(56) References Cited

OTHER PUBLICATIONS

Huang et al., Picomolar Dichotomous Activity of Gnidimacrin Against HIV-1, PLoS One, vol. 6, 2011, e26677, 8 pages.

Jiang et al, c-Myc and Sp1 Contribute to Proviral Latency by Recruiting Histone Deacetylase 1 to the Human Immunodeficiency Virus Type 1 Promoter, Journal of Virology, vol. 81, 2007, pp. 10914-10923.

Jiang et al., Recruitment of DNA Damage Checkpoint Proteins to Damage in Transcribed and Nontranscribed Sequences, Molecular and Cellular Biology, vol. 26, No. 1, 2006, pp. 39-49.

Jiang et al., Synergistic Reactivation of Latent HIV Expression by Ingenol-3-Angelate, PEP005,Targeted NF-kB Signaling in Combination with JQ1 Induced p-TEFb Activation, PLoS Pathogens, vol. 11, Issue 7, Jul. 30, 2015, pp. 1-27.

Jiang et al., Targeting NF-κB Signaling with PKC Agonists as an Emerging Strategy for Combating HIV Latency, AIDS Research and Human Retroviruses, 2014, pp. 1-14.

Jiang et al., Reactivation of HIV Latency by a Newly Modified Ingenol Derivative Via Protein Kinase Cδ-NF-κB Signaling, AIDS, 2014, pp. 1-14.

Johnson et al., Knockin Mice Expressing a Chimeric p53 Protein Reveal Mechanistic Differences in How p53 Triggers Apoptosis and Senescence, Proc Natl Acad Sci, vol. 105, 2008, pp. 1215-1220.

Jordan et al., HIV Reproducibly Establishes a Latent Infection After Acute Infection of T Cells in vitro, The EMBO Journal, vol. 22, No. 8, 2003, pp. 1868-1877.

Kalinina et al., Modelling Binding Between CCR5 and CXCR4 Receptors and Their Ligands Suggests the Surface Electrostatic Potential of the Co-Receptor to be a Key Player in the HIV-1 Tropism, Retrovirology, vol. 10, 2013, 11 pages.

Kohler et al., Human immunodeficiency virus type 1 (HIV-1) induces activation of multiple STATs in CD4+ cells of lymphocyte or monocyte/macrophage lineages, Journal of Leukocyte Biology, vol. 73, Mar. 2003, pp. 407-416.

Kulkosky et al., Prostratin: Activation of Latent HIV-1 Expression Suggests a Potential Inductive Adjuvant Therapy for HAART, Blood, vol. 98, No. 10, 2001, pp. 3006-3015.

Kumar et al., Human Immunodeficiency Virus Type 1 RNA Levels in Different Regions of Human Brain: Quantification Using Real-time Reverse Transcriptase-polymerase Chain Reaction, Journal of NeuroVirology, vol. 13, 2007, pp. 210-224.

Laird et al., Ex Vivo analysis identifies effective HIV-1 latency-reversing drug combinations, The Journal of Clinical Investigation, vol. 125, No. 5, 2015, pp. 1901-1912.

Lavigne et al., Interaction of HP1 and Brg1/Brm with the Globular Domain of Histone H3 is Required for HP1-Mediated Repression, PLoS Genet, vol. 5, 2009, p. e1000769.

Lerner et al., The Gut Mucosal Viral Reservoir in HIV-Infected Patients is not the Major Source of Rebound Plasma Viremia Following Interruption of Highly Active Antiretroviral Therapy, Journal of Virology, vol. 85, No. 10, 2011, pp. 4772-4782.

Liang et al., Syntheses, Biological Evaluation and SAR of Ingenol Mebutate Analogues for Treatment of Actinic Keratosis and Non-Melanoma Skin Cancer, Bioorganic & Medicinal Chemistry Letters, vol. 23, 2013, pp. 5624-5629.

Lopez-Cabrera et al., Transcriptional Regulation of the Gene Encoding the Human C-type Lectin Leukocyte Receptor AIM/CD69 and Functional Characterization of Its Tumor Necrosis Factor-alpha-responsive Elements, The Journal of Biological Chemistry, vol. 270, No. 37, 1995, pp. 21545-21551.

Lucera et al., The Histone Deacetylase Inhibitor Vorinostat (SAHA) Increases the Susceptibility of Uninfected CD4$^+$ T Cells to HIV by Increasing the Kinetics and Efficiency of Postentry Viral Events, Journal of Virology, vol. 88, No. 18, 2014, pp. 10803-10812.

Macal et al., Effective CD4+ T-cell restoration in gut-associated lymphoid tissue of HIV-infected patients is associated with enhanced Th17 cells and polyfunctional HIV-specific T-cell responses, Mucosal Immunol, vol. 1, 2008, pp. 475-488.

Margolis et al., Combined Approaches for HIV Cure, Curr Opin HIV AIDS, vol. 8, No. 3, 2013, pp. 230-235.

Mehla et al., Bryostatin Modulates Latent HIV-1 Infection via PKC and AMPK Signaling but Inhibits Acute Infection in a Receptor Independent Manner, PLoS One, vol. 5, 2010, p. e11160.

Nasi et al., Aging with HIV Infection: A Journey to the Center of InflammAIDS, Immunosenescence and NeuroHIV, Immunology Letters, vol. 162, 2014, pp. 329-323.

Pandelo Jose et al., Reactivation of Latent HIV-1 by New Semi-Synthetic Ingenol Esters, Virology, vol. 462, Issue 1, Jul. 9, 2014, pp. 328-339.

Persaud et al., Absence of Detectable HIV-1 Viremia After Treatment Cessation in an Infant, The New England Journal of Medicine, vol. 369, 2013, pp. 1828-1835.

Rasmussen et al., Comparison of HDAC Inhibitors in Clinical Development: Effect on HIV Production in Latently Infected Cells and T-cell Activation, Human Vaccines & Immunotherapeutics, vol. 9, Issue 5, 2013, pp. 993-1001.

Richman et al., The Challenge of Finding a Cure for HIV Infection, Science, vol. 323, 2009, pp. 1304-1307.

Shalit, P., Management of dyslipidemia in patients with human immunodeficiency virus, Reviews in Cardiovascular Medicine, vol. 15, Suppl 1, 2014, pp. S38-S46.

Shan et al., A Novel PCR Assay for Quantification of HIV-1 RNA, Journal of Virology, vol. 87, No. 11, 2013, pp. 6521-6525.

Shan et al., Stimulation of HIV-1-Specific Cytolytic T Lymphocytes Facilitates Elimination of Latent Viral Reservoir After Virus Reactivation, Immunity, vol. 36, 2012, pp. 491-501.

Shirakawa et al., Reactivation of latent HIV by histone deacetylase inhibitors, Trends Microbiol, Jun. 2013, 21(6), pp. 277-285; doi:10.1016/j.tim.2013.02.005.

Siliciano et al., Long-Term follow-up studies confirm the stability of the latent reservoir for HIV-1 in resting CD4$^+$ T cells, Nature Medicine, vol. 9, No. 6, 2003, pp. 727-728.

Sorg et al., Structure/Activity Relationships of Polyfunctional Diterpenes of the Ingenane Type. I. Tumor-Promoting Activity of Homologous, Aliphatic 3-Esters of Ingenol and of Delta 7,8-Isoingenol-3-Tetradecanoate, Carcinogenesis, vol. 8, No. 1, 1987, pp. 1-4.

Soriano-Sarabia et al., Quantitation of Replication-Competent HIV-1 in Populations of Resting CD4$^+$ T Cells, Journal of Virology, vol. 88, No. 24, 2014, pp. 14070-14077.

Spina et al., An In-Depth Comparison of Latent HIV-1 Reactivation in Multiple Cell Model Systems and Resting CD4+ T Cells from Aviremic Patients, PLoS Pathog, vol. 9, 2013, p. e1003834.

Stacey et al., Induction of a Striking Systemic Cytokine Cascade prior to Peak Viremia in Acute Human Immunodeficiency Virus Type 1 Infection, in Contrast to More Modest and Delayed Responses in Acute Hepatitis B and C Virus Infections, Journal of Virology, vol. 83, No. 8, 2009, 15 pages.

Tang et al., Infection of Female Primary Lower Genital Tract Epithelial Cells after Natural Pseudotyping of HIV-1: Possible Implications for Sexual Transmission of HIV-1, PLoS One, vol. 9, Issue 7, 2014, p. e101367.

Tripathy et al., H3K27 Demethylation at the Proviral Promoter Sensitizes Latent HIV to the Effects of Vorinostat in Ex Vivo Cultures of Resting CD4$^+$ T Cells, Journal of Virology, vol. 89, No. 16, 2015, pp. 8392-8405.

Verma et al., Identification of Potent, Selective, Cell-Active Inhibitors of the Histone Lysine Methyltransferase EZH2, ACS Medicinal Chemistry Letters, vol. 3, 2012, pp. 1091-1096.

Whitney et al., Rapid Seeding of the Viral Reservoir Prior to SIV Viraemia in Rhesus Monkeys, Nature, vol. 512, Aug. 7, 2014, 15 pages.

Wong et al., Recovery of Replication-Competent HIV Despite Prolonged Suppression of Plasma Viremia, Science, vol. 278, 1997, pp. 1291-1295.

Zhou et al., RNA Polymerase II Elongation Control, Annu Rev Biochem, vol. 81, 2012, pp. 119-143.

Fejer et al., "Characterization of Transgenic Mice Containing Adenovirus Early Region 3 Genomic DNA," Journal of Virology, Sep. 1994, vol. 68, No. 9, pp. 5871-5881.

(56) References Cited

OTHER PUBLICATIONS

He et al., "Synergistic activation of the CMV promoter by NF-κB P50 and PKG," Biochemical and Biophysical Research Communications, 2004, vol. 321, pp. 13-20.

* cited by examiner

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
tttttttttt tttttttttt tttttttgaag                              30

<210> SEQ ID NO 2
<211> LENGTH: 26
<212> TYPE: DNA
<213> ORGANISM: Artificial Sequence
<220> FEATURE:
<223> OTHER INFORMATION: Synthetic probe
```

<400> SEQUENCE: 2
tgcctgtact gggtctctct ggttag    26

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
agcttgctac aagggacttt cc    22

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
acccagtaca ggcaaaaagc ag    22

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
ggagcgacca tcttcttca    19

<210> SEQ ID NO 6
<211> LENGTH: 17
<212> TYPE: DNA
<213> ORGANISM: Artificial Sequence
<220> FEATURE:
<223> OTHER INFORMATION: Synthetic primer

<400> SEQUENCE: 6
agggtgtcgc cctcgaa    17

<210> SEQ ID NO 7
<211> LENGTH: 22
<212> TYPE: DNA
<213> ORGANISM: Artificial Sequence
<220> FEATURE:
<223> OTHER INFORMATION: Synthetic probe

<400> SEQUENCE: 7
ctacaagacc cgcgccgagg tg    22

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gccctcagat gctrcatata a    21

COMPOSITIONS AND METHODS FOR REACTIVATING LATENT VIRAL INFECTIONS

CROSS-REFERENCES TO RELATED APPLICATIONS

This application is a continuation of International Patent Application No. PCT/US2015/042716 filed Jul. 29, 2015, which claims priority to U.S. Provisional Application No. 62/035,333, filed Aug. 8, 2014, which applications are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. AI043274 and DK061297, awarded by the National Institutes of Health. The Government has certain rights in this invention.

REFERENCE TO A SEQUENCE LISTING

The Sequence Listing written in file SequenceListing 070772-1038060.txt created on Feb. 7, 2017, 1,842 bytes, machine format IBM-PC, MS-Windows operating system, is hereby incorporated by reference in its entirety for all purposes.

BACKGROUND OF THE INVENTION

Anti-retroviral therapy (ART) is effective in suppressing HIV replication but it fails to eliminate latent viral reservoirs in HIV infected resting CD4+ T cells which, in blood, consist mainly of central and transitional memory CD4+ T cells [1-4]. Current ART options do not eradicate HIV from infected cells. In addition, these cells are invisible to the virus-specific immune responses in the setting of viral latency [5,6]. The viral reservoir is rapidly seeded and HIV latency might be established immediately after virus infection [7,8]. Despite initiation of ART in infants within hours of birth to HIV infected mothers, stable viral reservoirs were established and viral rebound occurred when therapy was interrupted [9]. In the simian immunodeficiency virus (SIV) model of AIDS, stable viral reservoirs are established within 2.5 days of infection [10]. The viral reactivation was detected in rhesus macaques following therapy interruption despite the initiation of ART at 3 days post SIV infection [10,11]. Collectively, these studies demonstrate that a very early initiation of ART may not be sufficient to prevent nor eliminate latent virus reservoirs [9,11,12]. It has been observed that the morbidity of HIV persistence in HIV-positive individuals on long-term ART includes drug toxicities and a higher risk of developing complications including dyslipidemia, cardiovascular disease and insulin resistance [13-15]. Therefore, a therapeutic cure of HIV is urgently needed that leads to viral eradication and experimental strategies for directly targeting HIV latent reservoirs need to be developed. The present invention satisfies these needs and provides related advantages as well.

BRIEF SUMMARY OF THE INVENTION

In certain aspects, the present invention provides a composition comprising ingenol-3-angelate (PEP005) and one or more additional latency reactivation agents.

In some embodiments, the one or more additional latency reactivation agents is selected from the group consisting of a positive transcription elongation factor b activator, a histone methyltransferase (HMT) inhibitor, a histone deacetylase (HDAC) inhibitor, a DNA methyltransferase inhibitor, an NF-κB activator, an Akt/HEXIM-1 modulator, a Jak/Stat pathway modulator, a diterpene compound (e.g., an ingenol derivative, a phorbol ester), a macrolide lactone, a diacylglycerol (DAG) lactone, a protein kinase C (PKC) activator, and combinations thereof.

In some embodiments, the composition comprises a combination of ingenol-3-angelate (PEP005) and JQ1. In other embodiments, the composition comprises a combination of ingenol-3-angelate (PEP005) and GSK343. In yet other embodiments, the composition comprises a combination of ingenol-3-angelate (PEP005) and vorinostat (suberanilohydroxamic acid; SAHA). In certain embodiments, the composition further comprises a viral therapy vaccine. In certain embodiments, the composition further comprises a pharmaceutically acceptable carrier, excipient, or diluent.

In certain other aspects, the present invention provides a method for reactivating a latent virus in a subject infected with the virus, the method comprising administering to the subject an effective amount of ingenol-3-angelate (PEP005) alone or in combination with one or more additional latency reactivation agents.

In some embodiments, the one or more additional latency reactivation agents is selected from the group consisting of a positive transcription elongation factor b activator, a histone methyltransferase (HMT) inhibitor, a histone deacetylase (HDAC) inhibitor, a DNA methyltransferase inhibitor, an NF-κB activator, an Akt/HEXIM-1 modulator, a Jak/Stat pathway modulator, a diterpene compound (e.g., an ingenol derivative, a phorbol ester), a macrolide lactone, a diacylglycerol (DAG) lactone, a protein kinase C (PKC) activator, and combinations thereof. In certain embodiments, the method further comprises co-administering a viral therapy vaccine.

In some embodiments, the method comprises co-administering a combination of ingenol-3-angelate (PEP005) and JQ1. In other embodiments, the method comprises co-administering a combination of ingenol-3-angelate (PEP005) and GSK343. In yet other embodiments, the method comprises co-administering a combination of ingenol-3-angelate (PEP005) and vorinostat (suberanilohydroxamic acid; SAHA). In particular embodiments, a combination of ingenol-3-angelate (PEP005) and one or more additional latency reactivation agents (e.g., JQ1, GSK343, and/or SAHA) is capable of synergistically inducing reactivation of the latent virus.

In yet other aspects, the present invention provides a kit comprising: (a) ingenol-3-angelate (PEP005); and (b) one or more additional latency reactivation agents.

In some embodiments, the one or more additional latency reactivation agents is selected from the group consisting of a positive transcription elongation factor b activator, a histone methyltransferase (HMT) inhibitor, a histone deacetylase (HDAC) inhibitor, a DNA methyltransferase inhibitor, an NF-κB activator, an Akt/HEXIM-1 modulator, a Jak/Stat pathway modulator, a diterpene compound (e.g., an ingenol derivative, a phorbol ester), a macrolide lactone, a diacylglycerol (DAG) lactone, a protein kinase C (PKC) activator, and combinations thereof. In certain embodiments, the kit further comprises a viral therapy vaccine.

In some embodiments, the kit comprises a combination of ingenol-3-angelate (PEP005) and JQ1. In other embodiments, the kit comprises a combination of ingenol-3-angelate (PEP005) and GSK343. In yet other embodiments, the kit comprises a combination of ingenol-3-angelate (PEP005) and vorinostat (suberanilohydroxamic acid; SAHA).

Other objects, features, and advantages of the present invention will be apparent to one of skill in the art from the following detailed description and figures.

DETAILED DESCRIPTION OF THE INVENTION

I. Introduction

Figure 1:
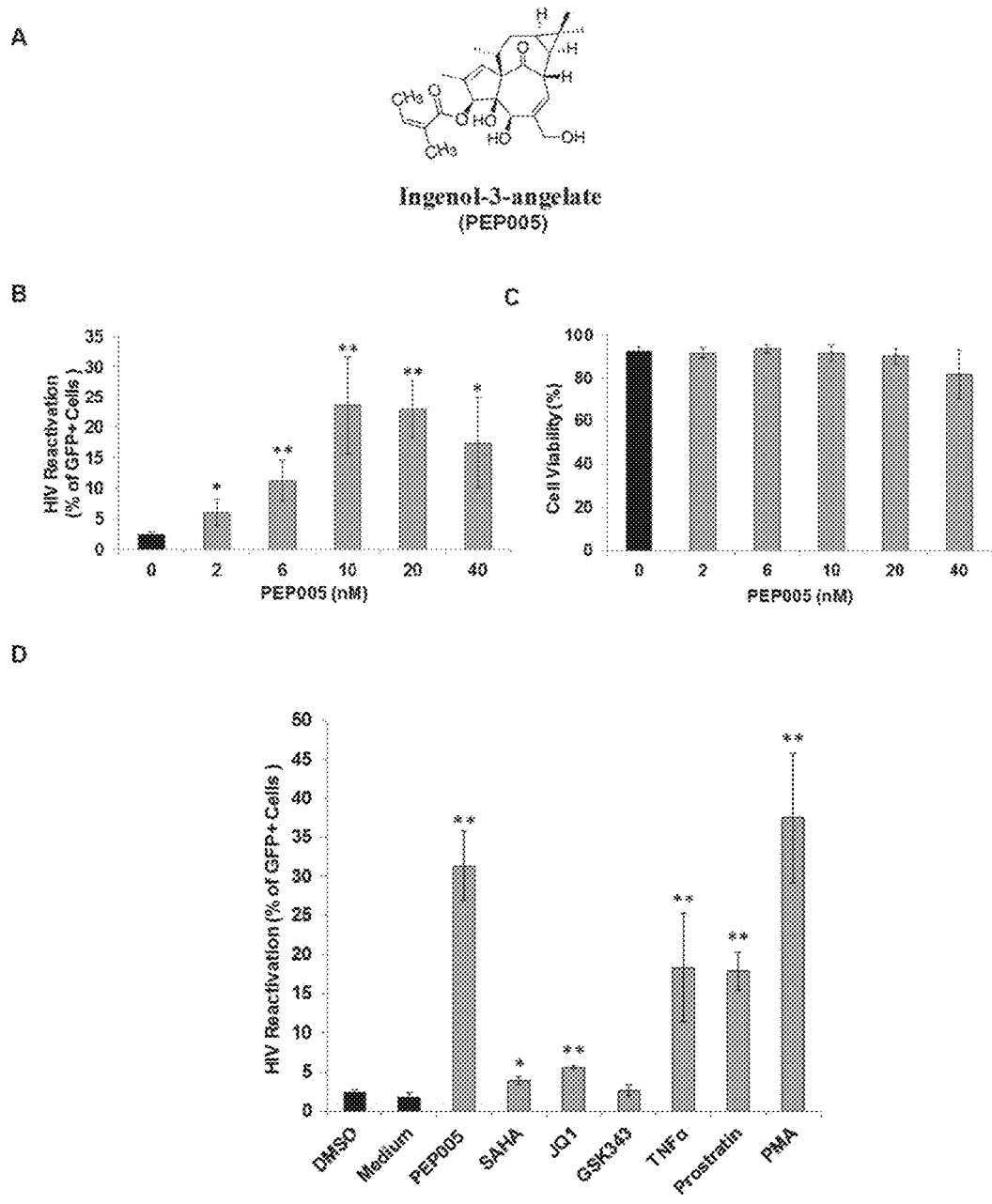
FIG. 1: PEP005 induces reactivation of HIV latency in vitro. J-Lat A1 cells were exposed to different concentrations of PEP005 and virus reactivation was measured by GFP expression using flow cytometry. Cell viability was determined by Live/Dead dye staining. (A) Chemical Structure of PEP005. (B, C) PEP005 reactivates HIV in a dose-dependent manner and displays minimal cytotoxicity. (D) PEP005 potently reactivates latent HIV in cell lines compared with other LRAs. J-Lat A1 cells were treated with 10 nM PEP005, 500 nM SAHA, 2 µM JQ1, 2 µM GSK343, 10 ng/ml TNF, 2 µM Prostratin, or 5 ng/ml PMA for 24 hours and the percentage of GFP expression was evaluated using flow cytometry. *, $p<0.05$; **, $p<0.01$.

Stable latent viral reservoirs in HIV infected individuals are rapidly reactivated following the interruption of antiretroviral therapy (ART). Despite an early initiation of ART, viral reservoirs are established and persist as demonstrated in the case of the Mississippi baby and from recent studies of the SIV model of AIDS. Therefore, new strategies are needed for the eradication of the latent HIV reservoirs. The present inventors have discovered that ingenol-3-angelate (PEP005), a member of a new class of anti-cancer ingenol compounds, effectively reactivated HIV from latency in primary CD4+ T cells from HIV infected individuals receiving ART. Importantly, a combination of PEP005 and JQ1, a p-TEFb agonist, reactivated HIV from latency at a level that was on average 7.5-fold higher compared to PEP005 alone. As such, the potency of synergistic effects of PEP005 and JQ1 provides novel opportunities for advancing HIV eradication strategies. In summary, ingenols represent a new group of compounds for combating HIV latency.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "subject", "patient" or "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

A "therapeutically effective amount" includes an amount or quantity effective, at dosages and for periods of time necessary, to achieve the desired therapeutic or prophylactic result.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering an effective amount of the compounds described herein for reactivating a latent viral infection caused by a virus such as HIV.

By "co-administer" it is meant that a first compound described herein is administered at the same time, just prior to, or just after the administration of a second compound described herein, e.g., the sequential or simultaneous administration of ingenol-3-angelate (PEP005) and one or more latency reactivation agents. For example, two or more compounds can be co-administered by administering a pharmaceutical composition adapted for oral administration that contains the two or more compounds. As another example, two or more compounds can be co-administered by administering one compound and then administering the other compound. In some instances, the co-administered compounds are administered by the same route. In other instances, the co-administered compounds are administered via different routes. For example, one compound can be administered orally, and the other compound can be administered, e.g., sequentially or simultaneously, via intravenous or intramuscular injection.

The terms "anti-retroviral therapy" or "ART" include administering one or more compounds simultaneously or sequentially to reduce or suppress the replication of a virus within an infected individual. This can be achieved, for example, by administering various classes of anti-retroviral compounds to an infected individual that inhibit various steps of the replication cycle. These classes of compounds include, but are not limited to, fusion inhibitors, nucleoside reverse transcriptase inhibitors, integrase inhibitors, protease inhibitors, and combinations thereof. For example, anti-retroviral therapy can be used to treat viral infections caused by human immunodeficiency virus (HIV), cytomegalovirus (CMV), or adenovirus. One non-limiting goal of this therapy in HIV, for example, is to decrease the viral levels and increase the amount of CD4+ T cells in infected individuals.

The term "latent virus" includes a state of the viral life cycle where the viral genome has integrated into the chromosomal DNA of the infected cell, but replication of the genome and viral proliferation in the infected cell is dormant. In some instances, the dormant viral replication impedes the treatment of viral infection with anti-retroviral therapy because anti-retroviral therapy targets various stages of the viral replication cycle. For example, latent HIV virus cannot be treated using anti-retroviral therapy, and is known problem inhibiting the functionality of anti-retroviral treatment techniques.

The term "latent reservoir" includes a cell or group of cells that are infected with a latent virus such as, for example, latent HIV.

The term "reactivating a latent virus" includes administering a compound or combination of compounds to induce a latent virus infected cell into an active replication and proliferation state. The term includes, inter alia, administering one or more latency reactivation agents described herein.

The terms "latency reactivation agent" or "latency reversing agent" include a compound or combination of compounds capable of reactivating a latent virus. For example, the terms include a single compound that is capable of inducing reactivation of a latent virus. As another example, the terms also include a combination of two or more compounds that are capable of synergistically or additively inducing reactivation of a latent virus. Latency reactivation agents are useful for treating a variety of latent viral infections including, but not limited to, latent HIV, CMV, and adenoviral infections. Latency reactivation agents include, but are not limited to, ingenol-3-angelate (PEP005), as well as any compound belonging to a class selected from a positive transcription elongation factor b activator, a histone methyltransferase (HMT) inhibitor, a histone deacetylase (HDAC) inhibitor, a DNA methyltransferase inhibitor, an NF-κB activator, an Akt/HEXIM-1 modulator, a Jak/Stat pathway modulator, a diterpene compound (e.g., an ingenol derivative, a phorbol ester), a macrolide lactone, a diacylglycerol (DAG) lactone, a protein kinase C (PKC) activator, and combinations thereof.

The term "effective amount" includes a dosage sufficient to produce a desired result with respect to the indicated disorder, condition, or mental state. The desired result may comprise a subjective or objective improvement in the recipient of the dosage. In one non-limiting example, an effective amount of PEP005 and JQ1 includes an amount sufficient to reactivate latent HIV expression. Also, for example, an effective amount includes an amount sufficient to suppress HIV infection of primary CD4+ T cells. Thus, an effective amount can be an amount that down-modulates cell surface expression of HIV co-receptors comprising CD4, CCR5, and/or CXCR4. The effective amount will vary with the type of subject being treated, the compound or combination of compounds applied, and/or the amount of anti-retroviral treatments administered to the subject.

The phrase "enhancing a therapeutic benefit" includes any of a number of subjective or objective factors indicating a beneficial response or improvement of the condition being treated as discussed herein. For example, enhancing the therapeutic benefit comprises administering two or more compounds to produce a desired clinical result greater than any one of the compounds administered separately. Also, for example, enhancing the therapeutic benefit comprises administering two or more latency reactivating agents to produce the desired clinical result greater than any one of the latency reactivating agents administered separately. In yet another example, enhancing the therapeutic benefit comprises administering two or more latency reactivation agents in combination with a viral therapy vaccine to more effectively combat and kill reactivated virally infected cells.

The term "pharmaceutically acceptable" includes a substance which does not interfere with the effectiveness or the biological activity of the active ingredients and which is not toxic to the hosts in the amounts used, and which hosts may be either humans or animals to which it is to be administered.

The term "low to minimal cytotoxicity" includes measuring the toxic effect of an administered compound or compounds in host cells based on the amount of the compound(s) administered. Thus, low to minimal cytotoxicity can be an amount that is not toxic to the cells or at a level of toxicity that the majority of cells are unaffected.

The term "global T cell activation" includes inducing a large scale immune response in a host organism. In some instances, global T cell activation could trigger a fatal systemic immune response.

The terms "synergistic" or "synergistically" include an enhanced therapeutic benefit or effect where a combination of two or more compounds produces a result that exceeds their expected additive effect. For example, synergistic latency reactivation agents enhance latent viral reactivation to an extent that exceeds their expected additive effect.

The term "viral therapy vaccine" includes compositions that are administered to a subject that increase the subject's response to a viral infection. In some instances, a viral therapy vaccine can be administered to a subject to increase the subject's immune response to a viral infection. For example, a viral therapy vaccine can be administered to a subject to increase the subject's ability to combat and kill virally infected cells that have been reactivated from their latent state.

The term "cytotoxic T lymphocytes (CTL) booster" includes compositions comprising proteins, DNA, RNA, and/or other biologic or non-biologic matter that can be used to improve CTL response and proliferation to combat and kill virally infected cells that have been reactivated from their latent state.

III. Description of the Embodiments

The present invention provides compositions comprising ingenol-3-angelate (PEP005) and one or more additional latency reactivation agents. The present invention also provides methods for reactivating a latent virus in a subject infected with the virus, the method comprising administering to the subject an effective amount of ingenol-3-angelate (PEP005) optionally in combination with one or more additional latency reactivation agents. In particular embodiments, a combination of ingenol-3-angelate (PEP005) with one or more additional latency reactivation agents advantageously provides a synergistic effect at inducing reactivation of a latent virus such as HIV. The present invention further provides kits comprising ingenol-3-angelate (PEP005) and one or more additional latency reactivation agents.

1. Compositions

In certain aspects, the present invention provides a composition comprising ingenol-3-angelate (PEP005) and one or more additional latency reactivation agents.

In some embodiments, the ingenol-3-angelate (PEP005) is present in an amount that is effective to enhance a therapeutic benefit of the one or more additional latency reactivation agents. In particular embodiments, the therapeutic benefit comprises reactivation of a latent virus in a subject infected with the virus. In certain instances, the latent virus is present as viral reservoirs in virus-infected cells (e.g., HIV-infected resting CD4+ T cells).

In some embodiments, the virus is selected from the group consisting of a human immunodeficiency virus (HIV), a cytomegalovirus (CMV), adenoviruses, papovaviruses, herpesviruses, varicella-zoster virus, Epstein-Barr virus, pox viruses, vaccinia virus, hepatitis B virus, rhinoviruses, hepatitis A virus, poliovirus, rubellavirus, hepatitis C virus, arboviruses, rabiesvirus, influenza viruses A and B, measles virus, mumps virus, and HTLV I and II. In particular embodiments, the virus is selected from the group consisting of a human immunodeficiency virus (HIV), a cytomegalovirus (CMV), and an adenovirus.

In some embodiments, the one or more additional latency reactivation agents is selected from the group consisting of a positive transcription elongation factor b activator, a histone methyltransferase (HMT) inhibitor, a histone deacetylase (HDAC) inhibitor, a DNA methyltransferase inhibitor, an NF-κB activator, an Akt/HEXIM-1 modulator, a Jak/Stat pathway modulator, a diterpene compound (e.g., an ingenol derivative, a phorbol ester), a macrolide lactone, a diacylglycerol (DAG) lactone, a protein kinase C (PKC) activator, and combinations thereof. Non-limiting examples of other latency reactivation agents include juglone (5HN, 5-hydroxynaphthalene-1,4-dione), disulfiram, AV6 (4-3',4'-dichloroanilino-6-methoxyquinoline), and combinations thereof.

Non-limiting examples of positive transcription elongation factor b activators include JQ1, hexamethylene bisacetamide (HMBA), and combinations thereof.

Non-limiting examples of histone methyltransferase (HMT) inhibitors include GSK343, BIX01294, chaetocin, 3-deazaneplanocin A (DZNep), and combinations thereof.

Non-limiting examples of histone deacetylase (HDAC) inhibitors include vorinostat (suberanilohydroxamic acid; SAHA), suberoyl bis-hydroxamic acid (SBHA), trichostatin A (TsA), scriptaid, oxamflatin, givinostat (ITF2357), belinostat (PXD101), droxinostat, CG05/CG06, valproic acid (VPA), sodium butyrate, apicidin, and combinations thereof.

Non-limiting examples of DNA methyltransferase inhibitors include decitabine, azacitidine, and combinations thereof.

Non-limiting examples of NF-κB activators include 12-deoxyphorbol-13-acetate (prostratin), phorbol myristate acetate (PMA), TNFα, and combinations ther Non-limiting examples of the Akt/HEXIM-1 modulator is hexamethylene bisacetamide (HMBA).

A non-limiting example of a Jak/Stat pathway modulator includes IL-7.

Non-limiting examples of diterpene compounds include an ingenol derivative, a phorbol ester, SJ23B, gnidimacrin, and combinations thereof. In some embodiments, the ingenol derivative is an ester of the diterpene ingenol and an organic acid. In certain embodiments, the organic acid is a saturated or unsaturated optionally substituted $C_1$-$C_{22}$ organic acid. In some instances, the ingenol derivative is selected from the group consisting of ingenol-3-trans-cinnamate (ING A), ingenol-3-hexanoate (ING B), ingenol-3-dodecanoate (ING C), 3-(2,4,6-dodecatrienoyl)-ingenol, 3-(2,4,6,8-tetradecatetranoyl)-ingenol, 20-hydroxy-ingenol-3-angelate, 20-O-acetyl-ingenol-3-angelate, and combinations thereof. In other instances, the ingenol derivative is any one of the compounds described in US 2015/0030638 and US 2003/0166613, the disclosures of which are hereby incorporated by reference in their entirety for all purposes. Non-limiting examples of phorbol esters include phorbol myristate acetate (PMA), 12-deoxyphorbol-13-acetate (prostratin), 12-deoxyphorbol 13-phenylacetate (DPP), and combinations thereof.

A non-limiting example of a macrolide lactone includes bryostatin.

In particular embodiments, the one or more additional latency reactivation agents is a positive transcription elongation factor b activator. In certain instances, the positive transcription elongation factor b activator is JQ1, i.e., the composition comprises a combination of ingenol-3-angelate (PEP005) and JQ1.

In particular embodiments, the one or more additional latency reactivation agents is a histone methyltransferase (HMT) inhibitor. In certain instances, the histone methyltransferase (HMT) inhibitor is GSK343, i.e., the composition comprises a combination of ingenol-3-angelate (PEP005) and GSK343.

In particular embodiments, the one or more additional latency reactivation agents is a histone deacetylase (HDAC) inhibitor. In certain instances, the histone deacetylase (HDAC) inhibitor is vorinostat (suberanilohydroxamic acid; SAHA), i.e., the composition comprises a combination of ingenol-3-angelate (PEP005) and SAHA.

In some embodiments, the composition further comprises a viral therapy vaccine. In particular embodiments, the viral therapy vaccine is present in an amount effective to enhance a therapeutic benefit of the latency reactivation agents. In certain embodiments, the therapeutic benefit comprises increasing a subject's immune response (e.g., cytotoxic T lymphocyte (CTL) response) by activating the proliferation of CTLs in the subject to more effectively combat and kill reactivated virally infected cells. In certain instances, the activated CTLs target viral proteins or fragments thereof that are presented on the surface of reactivated virally infected cells. Non-limiting examples of viral therapy vaccines include CTL boosters. Non-limiting examples of CTL boosters include viral proteins that are presented on the surface of infected cells, such as B Gag, Nef, Rev, Tat, and/or Env peptides.

In some embodiments, the composition further comprises a pharmaceutically acceptable excipient or diluent.

2. Methods

In certain other aspects, the present invention provides a method for reactivating a latent virus in a subject infected with the virus, the method comprising administering to the subject an effective amount of ingenol-3-angelate (PEP005).

In some embodiments, the effective amount of the ingenol-3-angelate (PEP005) is an amount that is capable of inducing RNA transcription from the latent virus in an infected cell (e.g., CD4+ T cell) from the subject. In certain instances, the latent virus is present as viral reservoirs in virus-infected cells (e.g., HIV-infected resting CD4+ T cells).

In some embodiments, the effective amount of the ingenol-3-angelate (PEP005) is an amount that displays low to minimal cytotoxicity without inducing global T cell activation (e.g., in the absence of major global T cell activation).

In some embodiments, the effective amount of the ingenol-3-angelate (PEP005) is an amount that suppresses or prevents the reactivated latent virus from infecting uninfected CD4+ T cells in the subject. In certain embodiments, the effective amount of the ingenol-3-angelate (PEP005) down-modulates the expression of cell surface receptors that are known to mediate viral (e.g., HIV) attachment and entry, thereby preventing the spread of viral infection to uninfected bystander CD4+ T cells.

In some embodiments, the ingenol-3-angelate (PEP005) is administered orally, topically, intravenously, intraperitoneally, intramuscularly, intralesionally, intrathecally, intranasally, subcutaneously, parenterally, or transmucosally.

In particular embodiments, the method of the present invention further comprises administering one or more additional latency reactivation agents selected from the group consisting of a positive transcription elongation factor b activator, a histone methyltransferase (HMT) inhibitor, a histone deacetylase (HDAC) inhibitor, a DNA methyltransferase inhibitor, an NF-κB activator, an Akt/HEXIM-1 modulator, a Jak/Stat pathway modulator, a diterpene compound (e.g., an ingenol derivative, a phorbol ester), a macrolide lactone, a diacylglycerol (DAG) lactone, a protein kinase C (PKC) activator, and combinations thereof. Non-limiting examples of other latency reactivation agents include juglone (5HN, 5-hydroxynaphthalene-1,4-dione), disulfiram, AV6 (4-3',4'-dichloroanilino-6-methoxyquinoline), and combinations thereof.

Non-limiting examples of positive transcription elongation factor b activators include JQ1, hexamethylene bisacetamide (HMBA), and combinations thereof.

Non-limiting examples of histone methyltransferase (HMT) inhibitors include GSK343, BIX01294, chaetocin, 3-deazaneplanocin A (DZNep), and combinations thereof.

Non-limiting examples of histone deacetylase (HDAC) inhibitors include vorinostat (suberanilohydroxamic acid; SAHA), suberoyl bis-hydroxamic acid (SBHA), trichostatin A (TsA), scriptaid, oxamflatin, givinostat (ITF2357), belinostat (PXD101), droxinostat, CG05/CG06, valproic acid (VPA), sodium butyrate, apicidin, and combinations thereof.

Non-limiting examples of DNA methyltransferase inhibitors include decitabine, azacitidine, and combinations thereof.

Non-limiting examples of NF-κB activators include 12-deoxyphorbol-13-acetate (prostratin), phorbol myristate acetate (PMA), TNFα, and combinations ther Non-limiting examples of the Akt/HEXIM-1 modulator is hexamethylene bisacetamide (HMBA).

A non-limiting example of a Jak/Stat pathway modulator includes IL-7.

Non-limiting examples of diterpene compounds include an ingenol derivative, a phorbol ester, SJ23B, gnidimacrin, and combinations thereof. In some embodiments, the ingenol derivative is an ester of the diterpene ingenol and an organic acid. In certain embodiments, the organic acid is a saturated or unsaturated optionally substituted $C_1$-$C_{22}$ organic acid. In some instances, the ingenol derivative is selected from the group consisting of ingenol-3-trans-cinnamate (ING A), ingenol-3-hexanoate (ING B), ingenol-3-dodecanoate (ING C), 3-(2,4,6-dodecatrienoyl)-ingenol, 3-(2,4,6,8-tetradecatetranoyl)-ingenol, 20-hydroxy-ingenol-3-angelate, 20-O-acetyl-ingenol-3-angelate, and combinations thereof. In other instances, the ingenol derivative is any one of the compounds described in US 2015/0030638 and US 2003/0166613, the disclosures of which are hereby incorporated by reference in their entirety for all purposes.

Non-limiting examples of phorbol esters include phorbol myristate acetate (PMA), 12-deoxyphorbol-13-acetate (prostratin), 12-deoxyphorbol 13-phenylacetate (DPP), and combinations thereof.

A non-limiting example of a macrolide lactone includes bryostatin.

In particular embodiments, the method of the present invention further comprises administering one or more additional latency reactivation agents comprising a positive transcription elongation factor b activator. In certain instances, the positive transcription elongation factor b activator is JQ1, i.e., the method comprises co-administering a combination of ingenol-3-angelate (PEP005) and JQ1.

In particular embodiments, the method of the present invention further comprises administering one or more additional latency reactivation agents comprising a histone methyltransferase (HMT) inhibitor. In certain instances, the positive transcription elongation factor b activator is GSK343, i.e., the method comprises co-administering a combination of ingenol-3-angelate (PEP005) and GSK343.

In particular embodiments, the method of the present invention further comprises administering one or more additional latency reactivation agents comprising a histone deacetylase (HDAC) inhibitor. In certain instances, the positive transcription elongation factor b activator is vorinostat (suberanilohydroxamic acid; SAHA), i.e., the method comprises co-administering a combination of ingenol-3-angelate (PEP005) and SAHA.

In preferred embodiments, a combination of the ingenol-3-angelate (PEP005) and the one or more additional latency reactivation agents (e.g., JQ1, GSK343, and/or SAHA) is capable of synergistically inducing reactivation of the latent virus.

In certain embodiments, the one or more additional latency reactivation agents is each independently administered orally, topically, intravenously, intraperitoneally, intramuscularly, intralesionally, intrathecally, intranasally, subcutaneously, parenterally, or transmucosally.

In certain embodiments, the method comprises administering an effective amount of ingenol-3-angelate (PEP005) alone or with one or more additional latency reactivation agents for reactivating a latent virus in a virally infected cell in a subject infected with the virus in combination with administering an effective amount of a viral therapy vaccine for increasing a subject's immune response (e.g., CTL response) to more effectively combat and kill the reactivated virally infected cell.

In some embodiments, the effective amount of the viral therapy vaccine is an amount that is capable of increasing the subject's immune response (e.g., cytotoxic T lymphocyte (CTL) response) by activating the proliferation of CTLs in the subject to more effectively combat and kill reactivated virally infected cells. In certain instances, the activated CTLs target viral proteins or fragments thereof that are presented on the surface of reactivated virally infected cells.

In some embodiments, the effective amount of the viral therapy vaccine is an amount that displays killing of virally infected cells that have been reactivated from their latent state.

Non-limiting examples of viral therapy vaccines include cytotoxic T lymphocytes (CTL) boosters. Non-limiting examples of CTL boosters include viral proteins that are presented on the surface of infected cells, such as B Gag, Nef, Rev, Tat, and/or Env peptides.

In some embodiments, the method comprises co-administering a combination of ingenol-3-angelate (PEP005), JQ1, and a cytotoxic T lymphocyte (CTL) booster. In other embodiments, the method comprises co-administering a combination of ingenol-3-angelate (PEP005), GSK343, and a CTL booster. In yet other embodiments, the method comprises co-administering a combination of ingenol-3-angelate (PEP005), vorinostat (suberanilohydroxamic acid; SAHA), and a CTL booster.

In particular embodiments, a combination of ingenol-3-angelate (PEP005) with one or more additional latency reactivation agents (e.g., JQ1, GSK343, and/or SAHA) and a viral therapy vaccine is capable of synergistically inducing reactivation of the latent virus and increasing an immune response to reactivated virally infected cells.

In other embodiments, the viral therapy vaccine is administered before ingenol-3-angelate (PEP005) and/or the one or more additional latency reactivation agents is administered.

In certain embodiments, the viral therapy vaccine is administered orally, topically, intravenously, intraperitoneally, intramuscularly, intralesionally, intrathecally, intranasally, subcutaneously, parenterally, or transmucosally.

In some embodiments, the virus is selected from the group consisting of a human immunodeficiency virus (HIV), a cytomegalovirus (CMV), adenoviruses, papovaviruses, herpesviruses, varicella-zoster virus, Epstein-Barr virus, pox viruses, vaccinia virus, hepatitis B virus, rhinoviruses, hepatitis A virus, poliovirus, rubellavirus, hepatitis C virus, arboviruses, rabiesvirus, influenza viruses A and B, measles virus, mumps virus, and HTLV I and II. In particular embodiments, the virus is selected from the group consisting of a human immunodeficiency virus (HIV), a cytomegalovirus (CMV), and an adenovirus.

In some embodiments, the subject is a human. In other embodiments, the subject is receiving anti-retroviral therapy (ART), e.g., highly active anti-retroviral therapy (HAART), suppressive anti-retroviral therapy, and the like.

3. Kits

In yet other aspects, the present invention provides a kit comprising: (a) ingenol-3-angelate (PEP005); and (b) one or more additional latency reactivation agents.

In some embodiments, the kit further comprises a label with instructions for administering the ingenol-3-angelate (PEP005) and/or the one or more additional latency reactivation agents.

In certain embodiments, the one or more additional latency reactivation agents is selected from the group consisting of a positive transcription elongation factor b activator, a histone methyltransferase (HMT) inhibitor, a histone deacetylase (HDAC) inhibitor, a DNA methyltransferase inhibitor, an NF-κB activator, an Akt/HEXIM-1 modulator, a Jak/Stat pathway modulator, a diterpene compound (e.g., an ingenol derivative, a phorbol ester), a macrolide lactone, a diacylglycerol (DAG) lactone, a protein kinase C (PKC) activator, and combinations thereof.

In particular embodiments, the one or more additional latency reactivation agents is a positive transcription elongation factor b activator. In certain instances, the positive transcription elongation factor b activator is JQ1, i.e., the kit comprises a combination of ingenol-3-angelate (PEP005) and JQ1.

In particular embodiments, the one or more additional latency reactivation agents is a histone methyltransferase (HMT) inhibitor. In certain instances, the positive transcription elongation factor b activator is GSK343, i.e., the kit comprises a combination of ingenol-3-angelate (PEP005) and GSK343.

In particular embodiments, the one or more additional latency reactivation agents is a histone deacetylase (HDAC) inhibitor. In certain instances, the positive transcription elongation factor b activator is vorinostat (suberanilohydroxamic acid; SAHA), i.e., the kit comprises a combination of ingenol-3-angelate (PEP005) and SAHA.

In certain embodiments, the kit further comprises a viral therapy vaccine. Non-limiting examples of viral therapy vaccines include cytotoxic T lymphocytes (CTL) boosters. Non-limiting examples of CTL boosters include viral proteins that are presented on the surface of infected cells, such as B Gag, Nef, Rev, Tat, and/or Env peptides.

In some embodiments, the kit comprises a combination of ingenol-3-angelate (PEP005), JQ1, and a cytotoxic T lymphocytes (CTL) booster. In other embodiments, the kit comprises a combination of ingenol-3-angelate (PEP005), GSK343, and a CTL booster. In yet other embodiments, the kit comprises a combination of ingenol-3-angelate (PEP005), vorinostat (suberanilohydroxamic acid; SAHA), and a CTL booster.

IV. Latency Reactivation Agents

The present invention provides compositions and kits comprising ingenol-3-angelate (PEP005) as a latency reactivation agent and one or more additional latency reactivation agents. The present invention also provides methods for reactivating a latent virus by administering an effective amount of ingenol-3-angelate (PEP005) as a latency reactivation agent alone or in combination with one or more additional latency reactivation agents.

Non-limiting examples of additional latency reactivation agents include positive transcription elongation factor b activators, histone methyltransferase (HMT) inhibitors, histone deacetylase (HDAC) inhibitors, DNA methyltransferase inhibitors, NF-κB activators, Akt/HEXIM-1 modulators, Jak/Stat pathway modulators, diterpene compounds (e.g., ingenol derivatives, phorbol esters), macrolide lactones, diacylglycerol (DAG) lactones, protein kinase C (PKC) activators, juglone (5HN, 5-hydroxynaphthalene-1,4-dione), disulfiram, AV6 (4-3',4'-dichloroanilino-6-methoxyquinoline), pharmaceutically acceptable salts thereof, derivatives thereof, and combinations thereof.

1. Ingenol-3-Angelate (PEP005)

Ingenol-3-angelate, also known as ingenol mebutate, PEP005, or PICATO®, is a natural product found in the plant *Euphorbia peplus*. Ingenol-3-angelate is an ester of the diterpene ingenol and angelic acid. The full IUPAC chemical name of ingenol-3-angelate is (1aR,2S,5R,5aS,6S,8aS,9R,10aR)-5,5a-Dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e][10]annulen-6-yl (2Z)-2-methylbut-2-enoate. The structure of ingenol-3-angelate is shown below:

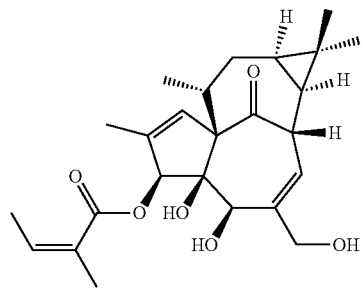

2. Positive Transcription Elongation Factor b Activators

Positive transcription elongation factor b, also known as P-TEFb, plays an essential role in the regulation of transcription by RNA polymerase II (Pol II) in eukaryotes. For the HIV virus, P-TEFb is targeted by the HIV Tat protein which bypasses normal cellular P-TEFb control and directly brings P-TEFb to the promoter proximal paused polymerase in the HIV genome. In certain embodiments, activators of P-TEFb are capable of binding to, stimulating, increasing, activating, facilitating, enhancing activation or enzymatic activity, sensitizing or upregulating the activity or expression of P-TEFb. In certain other embodiments, activators of P-TEFb are capable of increasing, enhancing, or upregulating the expression of an mRNA that encodes P-TEFb. Non-limiting examples positive transcription elongation factor b activators include JQ1, hexamethylene bisacetamide (HMBA), and combinations thereof.

In particular embodiments, the positive transcription elongation factor b activator is JQ1. The full IUPAC chemical name of JQ1 is (S)-tert-butyl 2-(4-(4-chlorophenyl)-2,3,9-trimethyl-6H-thieno[3,2-f][1,2,4]triazolo[4,3-a][1,4]diazepin-6-yl)acetate. JQ1 is an inhibitor of the bromo and extra terminal (BET) family of bromodomain proteins. BET proteins are key mediators for the assembly of the P-TEFb complex. The structure of JQ1 is shown below:

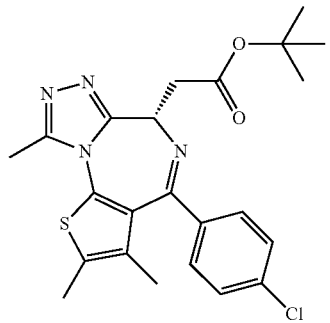

3. Histone Methyltransferase (HMT) Inhibitors

Histone methyltransferases, or HMTs, are histone-modifying enzymes that catalyze the transfer of methyl groups to lysine and arginine residues of histone proteins. By modifying the methylation of histone proteins, HMTs play an important biological role in the epigenetic modification of chromatin that directly impacts cellular activities including gene expression, DNA methylation, and genomic stability. Methylation of histone protein H3 at lysines 9 and 27 has been implicated in HIV latency (see, Shirakawa et al., Trends Microbiol, 21(6):277-285 (2013)). In certain embodiments, inhibitors of HMTs are capable of binding to, inhibiting, partially or totally blocking stimulation or enzymatic activity, decreasing, preventing, delaying activation, inactivating, desensitizing, or down regulating the activity or expression of HMTs. In certain other embodiments, inhibitors of HMTs are capable of decreasing, down regulating, or inhibiting the expression of an mRNA that encodes HMT. Non-limiting examples of HMT inhibitors include GSK343, BIX01294, chaetocin, 3-deazaneplanocin A (DZNep), G9a, and combinations thereof.

In particular embodiments, the HMT inhibitor is GSK343. GSK343 is an inhibitor of EZH2, which is a histone H3-lysine 27 methyltransferase. Inhibition of EZH2 has been implicated in reactivating latent HIV-infected cells. The chemical structure of GSK343 is shown below:

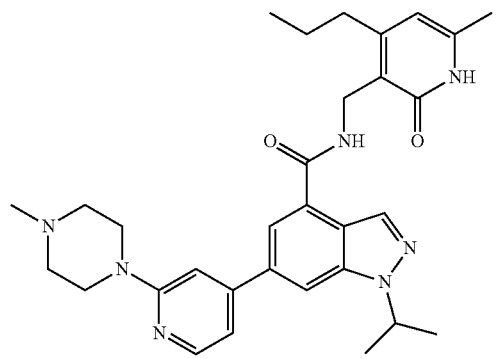

4. Histone Deacetylase (HDAC) Inhibitors

Histone deacetylases, also known as HDACs, are enzymes that remove acetyl groups from N-acetylated lysine amino acids on histone proteins. This process allows the histone proteins to more tightly wrap around DNA molecules. HDAC inhibitors have been shown to induce reactivation of virally infected latent cells, including herpes simples virus and HIV (see, Danaher et al., J Neurovirol, 11(3):306-17 (2005) and Shirakawa et al., Trends Microbiol, 21(6):277-85 (2013)). In certain embodiments, inhibitors of HDACs are capable of binding to, inhibiting, partially or totally blocking stimulation or enzymatic activity, decreasing, preventing, delaying activation, inactivating, desensitizing, or down regulating the activity or expression of HDACs. In certain other embodiments, inhibitors of HDACs are capable of decreasing, down regulating, or inhibiting the expression of an mRNA that encodes HDAC. Exemplary HDAC inhibitors include, but are not limited to, vorinostat, suberoyl bis-hydroxamic acid (SBHA), trichrostatin A (TsA), scriptaid, oxamflatin, givinostat (ITF2357), belinostat (PXD101), droxinostat, CG05/CG06, valproic acid (VPA), sodium butyrate, apicidin, and combinations thereof.

In particular embodiments, the HDAC inhibitor is vorinostat. Vorinostat is also known as suberanilohydroxamic acid, SAHA, or ZOLINZA®. The full IUPAC chemical name for SAHA is N-Hydroxy-N'-phenyloctanediamide. The chemical structure of vorinostat is shown below:

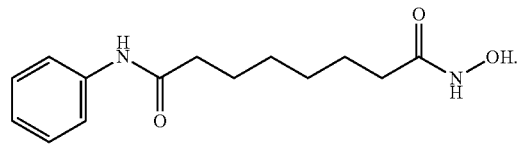 [SMILES: O=C(CCCCCCC(=O)Nc1ccccc1)NO]

5. DNA Methyltransferase Inhibitors

DNA methyltransferases are enzymes that transfer a methyl group to DNA. DNA methylation typically acts to suppress gene transcription, and methylation patterns play an important role in epigenetics. As such, inhibitors of DNA methyltransferase can directly alter cellular gene expression. Indeed, DNA methyltransfase inhibitors, in altering the gene expression pattern, can induce reactivation of HIV infected cells (see, Blazkova et al., PLoS Pathog, 5(8):e1000554 (2009)). In certain embodiments, inhibitors of DNA methyltransferases are capable of binding to, inhibiting, partially or totally blocking stimulation or enzymatic activity, decreasing, preventing, delaying activation, inactivating, desensitizing, or down regulating the activity or expression of DNA methyltransferases. In certain other embodiments, inhibitors of DNA methyltransferases are capable of decreasing, down regulating, or inhibiting the expression of an mRNA that encodes DNA methyltransferase. Non-limiting examples of DNA methyltransferases include decitabine, azacitidine, and combinations thereof.

6. NF-κB Activators

NF-κB is a protein complex that controls, among other things, transcription of cellular DNA; thus, it is a transcription factor. In some instances, activated NF-κB binds to DNA-binding sites where expression of specific genes is turned on. Several viruses, including HIV, have binding sites of NF-κB that control the expression of viral genes. NF-κB activation has been implicated in the reactivation of infected cells from their latent state (see, Hiscott et al., *J. Clin. Invest.*, 107(2):143-151 (2001)). In certain embodiments, activators of NF-κB are capable of binding to, stimulating, increasing, activating, facilitating, enhancing activation or enzymatic activity, sensitizing or upregulating the activity or expression of NF-κB or members of the NF-κB signaling pathway. In certain other embodiments, activators of NF-κB are capable of increasing, enhancing, or upregulating the expression of an mRNA that encodes NF-κB or members of the NF-κB signaling pathway. Non-limiting examples of NF-κB activators include 12-deoxyphorbol-13-acetate (prostratin), phorbol myristate acetate (PMA), TNFα, and combinations thereof.

7. Akt/HEXIM-1 Modulators

Non-phosphorylated HEXIM-1, in combination with other cellular factors including 7SK snRNA, forms a complex with positive transcription elongation factor b (P-TEFb) that sequesters P-TEFb and represses PTEFb activity. When HEXIM-1 is phosphorylated via the phosphoinositide 3-kinase/RAC-alpha serine/threonine-protein kinase (PI3K/Akt) pathway, the protein complex sequestering P-TEFb is released, thereby activating P-TEFb. For the HIV virus, activation of the PI3K/Akt pathway and phosphorylation of HEXIM-1 leading to the release of active P-TEFb has been implicated in the reactivation of HIV infected cells (see, Contreras et al. *PLOS Pathog.*, 3(10):e146 (2007)). In certain embodiments, modulators of Akt/HEXIM-1 are capable of binding to, stimulating, increasing, activating, facilitating, enhancing activation or enzymatic activity, sensitizing or upregulating the activity or expression of members of the PI3K/Akt pathway. In certain other embodiments, modulators of Akt/HEXIM-1 are capable of increasing, enhancing, or upregulating the expression of an mRNA that encodes members of the PI3K/Akt pathway. Non-limiting examples of Akt/HEXIM-1 modulators include hexamethylene bisacetamide (HMBA).

8. Jak/Stat Pathway Modulators

The Jak/Stat pathway is a transcription regulation pathway that transmits information from chemical signals outside the cell to gene promoters on the DNA in the cell nucleus. The pathway is made up of three components, a cellular membrane receptor, a Janus kinase (Jak), and a signal transducer and activator of transcription (Stat). The receptor is activated by a signal from a chemical messenger, thereby activating the kinase function of Jak, which then autophosphorylates itself. The STAT protein then binds to the phosphorylated receptor, where STAT is phosphorylated by JAK. The phosphorylated STAT protein binds to another phosphorylated STAT protein (dimerizes) and translocates into the cell nucleus. In the nucleus, the dimer binds to DNA and promotes transcription of genes responsive to STAT. An activated Jak/Stat pathway has been associated with actively replicating retroviral infections such as HIV (see, Kohler et al., *JLB*, 73(3) 407-416 (2003)). In certain embodiments, modulators of the Jak/Stat pathway are capable of binding to, stimulating, increasing, activating, facilitating, enhancing activation or enzymatic activity, sensitizing or upregulating the activity or expression of members of the Jak/Stat pathway. In certain other embodiments, modulators of the Jak/Stat pathway are capable of increasing, enhancing, or upregulating the expression of an mRNA that encodes members of the Jak/Stat pathway. Non-limiting examples of Jak/Stat pathway modulators include IL-7.

9. Diterpene Compounds

Diterpenes are a class of organic compounds based off of four isoprene units which are derived from genanylgeraniol pyrophosphate, and most diterpenes are of fungal or plant origin. In some instances, diterpenes have been shown to activate the protein kinase C (PKC) pathway. In certain embodiments, diterpenes are capable modulating the PKC pathway by binding to, stimulating, increasing, activating, facilitating, enhancing activation or enzymatic activity, sensitizing or upregulating the activity or expression of the members of the PKC family. In certain other embodiments, diterpenes are capable modulating the PKC pathway by increasing, enhancing, or upregulating the expression of an mRNA that encodes members of the PKC family. Non-limiting examples of diterpenes include ingenol derivatives, phorbol esters, SJ23B, gnidimacrin, and combinations thereof.

In some embodiments, the ingenol derivative is an ester of the diterpene ingenol and an organic acid. In certain embodiments, the organic acid is a saturated or unsaturated optionally substituted $C_1$-$C_{22}$ organic acid. In some instances, the ingenol derivative is selected from the group consisting of ingenol-3-trans-cinnamate (ING A), ingenol-3-hexanoate (ING B), ingenol-3-dodecanoate (ING C), 3-(2,4,6-dodecatrienoyl)-ingenol, 3-(2,4,6,8-tetradecatetranoyl)-ingenol, 20-hydroxy-ingenol-3-angelate, 20-O-acetyl-ingenol-3-angelate, and combinations thereof. In other instances, the ingenol derivative is any one of the compounds described in US 2015/0030638 and US 2003/0166613, the disclosures of which are hereby incorporated by reference in their entirety for all purposes.

Phorbol esters are tetracyclic members of the diterpene family. Phorbol is the parent diterpene of phorbol esters. Biologically, phorbol esters mimic the action of diacylglycerol, an activator of protein kinase C (PKC). In certain embodiments, phorbol esters are capable modulating the PKC pathway by binding to, stimulating, increasing, activating, facilitating, enhancing activation or enzymatic activity, sensitizing or upregulating the activity or expression of the members of the PKC family. In certain other embodiments, phorbol esters are capable modulating the PKC pathway by increasing, enhancing, or upregulating the expression of an mRNA that encodes members of the PKC family. Non-limiting examples of phorbol esters include phorbol myristate acetate (PMA), 12-deoxyphorbol-13-acetate (prostratin), 12-deoxyphorbol 13-phenylacetate (DPP), and combinations thereof.

10. Macrolide Lactones

Macrolide lactones are organic compounds that contain a large macrocyclic lactone ring. The lactone rings of macrolide lactones are usually 14, 15, or 16-membered. In some instances, macrolide lactones such as bryostatin and analogs thereof have been shown to activate the protein kinase C (PKC) pathway and can induce HIV reactivation in latently infected cells as described in DeChristopher et al., *Nature Chemistry*, 4, 705-710 (2012). In certain embodiments, macrolide lactones are capable of modulating the PKC pathway by binding to, stimulating, increasing, activating, facilitating, enhancing activation or enzymatic activity, sensitizing or upregulating the activity or expression of members of the PKC family. In certain other embodiments, macrolide lactones are capable modulating the PKC pathway by increasing, enhancing, or upregulating the expression of an mRNA that encodes members of the PKC pathway. Non-limiting examples of macrolide lactones include bryostatin.

11. Diacylglycerol (DAG) Lactones

Diacylglycerol (DAG) lactones are effective modulators of critical cellular signaling pathways. Diacylglycerol (DAG) is a known activator of protein kinase C (PKC) and the PKC pathway, and DAG lactones are structural mimetics of DAG. As such, DAG lactones are also capable of activating the PKC pathway and can induce HIV reactivation in latently infected cells. In certain embodiments, DAG lactones are capable of modulating the PKC pathway by binding to, stimulating, increasing, activating, facilitating, enhancing activation or enzymatic activity, sensitizing or upregulating the activity or expression of members of the PKC family. In certain other embodiments, DAG lactones are capable modulating the PKC pathway by increasing, enhancing, or upregulating the expression of an mRNA that encodes members of the PKC pathway. Non-limiting examples of DAG lactones are described in Hamer et al. (*J. Virology*, 77(19):10227-10236 (2003)).

12. Protein Kinase C (PKC) Activators

Protein kinase C, also known as PKC, is a family of protein kinase enzymes that are involved in controlling the function of many other proteins and cellular processes by phosphorylating the hydroxyl groups of serine and threonine amino acid residues of these proteins. Activation of PKC has many downstream effects, one of them being NF-κB activation, which can lead to HIV reactivation in latently infected cells. PKC activity is activated by, among other things, diacylglycerol (DAG) or DAG mimetics. In certain embodiments, activators of PKC are capable of binding to, stimulating, increasing, activating, facilitating, enhancing activation or enzymatic activity, sensitizing or upregulating the activity or expression of PKC. In certain other embodiments, activators of PKC are capable of increasing, enhancing, or upregulating the expression of an mRNA that encodes PKC. Non-limiting examples of PKC activators include diterpenes, phorbol esters, macrolide lactones, and DAG lactones such as those compounds described herein.

V. Viral Therapy Vaccines

In certain aspects, the present invention provides compositions and kits comprising ingenol-3-angelate (PEP005) alone or with one or more additional latency reactivation agents to reactivate latent virally infected cells in combination with a viral therapy vaccine to increase a subject's immune response (e.g., cytotoxic T lymphocyte (CTL) response) to more effectively combat and kill the reactivated virally infected cells. In other aspects, the present invention provides methods for reactivating a latent virus in a virally infected cell and increasing a subject's immune response (e.g., CTL response) to more effectively combat and kill the reactivated virally infected cells comprising administering ingenol-3-angelate (PEP005) as a latency reactivation agent alone or with one or more additional latency reactivation agents in combination a viral therapy vaccine.

Non-limiting examples of viral therapy vaccines include cytotoxic T lymphocytes (CTL) boosters. Non-limiting examples of cytotoxic T lymphocytes (CTL) boosters include viral proteins that are presented on the surface of infected cells. In HIV, those proteins include B Gag, Nef, Rev, Tat, Env, Pol, Vpr, Vpu, and Vif peptides. Other non-limiting examples of CTL boosters include viral DNA, RNA, and other biologic or non-biologic material.

Cytotoxic T lymphocytes (CTLs) are part of the adaptive immune response, and play a critical role in fighting viral infections. CTLs recognize and bind infected cells using T-cell receptors (TCR). TCRs contain a highly variable binding region that allow them to recognize a large range of antigens. TCRs bind to the major histocompatibility complex I (MHC I) of infected cells presenting an appropriate antigen. TCRs binding is highly specific, so only a small number of CTLs will be able to recognize a particular antigen. Once an antigen is recognized by CTLs binding to the MHC I complex of the infected cell, they activate to induce cellular death. Activated CTLs proliferate to fight the detected infection.

For the HIV virus, CTL response is limited by viral mutational rate. The high mutational rate in the proteins expressed on the cellular MHC complex creates 'escape mutations' that can avoid detection of activated CTLs, making the viral infection difficult to irradicate. The use of a viral therapy vaccine to induce and boost CTL response to better combat the infection, particularly in latently reactivated virally infected cells, is provided herein. In some embodiments, viral therapy vaccines stimulate CTL response to more effectively combat and kill the reactivated virally infected cells. In certain embodiments, CTLs are stimulated with a mixture of consensus HIV peptides known to be exhibited on the MHC I complex of infected cells.

VI. Pharmaceutical Compositions

The compounds described herein are useful in the manufacture of a pharmaceutical composition or a medicament for reactivating latent viral reservoirs in an infected subject. In certain aspects, a pharmaceutical composition or medicament can be administered to a subject for the treatment of a viral infection such as an HIV infection that leads to the reduction or elimination of the virus from latent reservoirs in infected resting cells such as central and/or transitional memory CD4+ T cells. In certain other aspects, a pharmaceutical composition or medicament can be administered to a subject for the treatment of a viral infection such as an HIV infection that leads to the reactivation of virally infected cells from latent reservoirs and activation of the subject's immune system to combat and kill the recently reactivated virally infected cells.

Pharmaceutical compositions or medicaments for use in the present invention can be formulated by standard techniques or methods well-known in the art of pharmacy using one or more physiologically acceptable carriers or excipients. Suitable pharmaceutical carriers are described herein and in, e.g., "Remington's Pharmaceutical Sciences" by E. W. Martin. Compounds and agents of the present invention and their physiologically acceptable salts and solvates can be formulated for administration by any suitable route, including, but not limited to, orally, topically, nasally, rectally, pulmonary, parenterally (e.g., intravenously, subcutaneously, intramuscularly, etc.), and combinations thereof. In some embodiments, the therapeutic agent is dissolved in a liquid, for example, water. The most suitable route of administration in any given case will depend in part on the nature, severity, and optionally, the stage of the viral infection. Co-administration of a plurality or combination of compounds may be by the same or different route of administration or together in the same pharmaceutical formulation.

The pharmaceutical compositions of the present invention can include ingenol-3-angelate (PEP005) in combination with positive transcription elongation factor b activators, histone methyltransferase (HMT) inhibitors, histone deacetylase (HDAC) inhibitors, DNA methyltransferase inhibitors, NF-κB activators, Akt/HEXIM-1 modulators, Jak/Stat pathway modulators, diterpene compounds (e.g., ingenol derivatives, phorbol esters), macrolide lactones, diacylglycerol (DAG) lactones, protein kinase C (PKC) activators, and combinations thereof, or any pharmaceutically acceptable salts thereof, as an active ingredient and a pharmaceutically acceptable carrier and/or excipient or diluent. In some embodiments, the pharmaceutical composition can include ingenol-3-angelate (PEP005) in combination with JQ1, GSK343, SAHA, and combinations thereof. In other embodiments, the pharmaceutical composition can include ingenol-3-angelate (PEP005) in combination with one or more latency reactivation agents (e.g., JQ1, GSK343, and/or SAHA) and one or more viral therapy vaccines (e.g., a CTL booster). A pharmaceutical composition of the invention may optionally contain additional therapeutic ingredients, e.g., one or more compounds for use in anti-retroviral therapy.

The compounds of the present invention can be combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein.

In certain embodiments, the pharmaceutical compositions are suitable for systemic administration. Systemic administration includes enteral administration (e.g., absorption of the compound through the gastrointestinal tract) or parenteral administration (e.g., injection, infusion, or implantation). In some embodiments, the compositions may be administered via a syringe or intravenously.

In some embodiments, the present invention provides a pharmaceutical composition including ingenol-3-angelate (PEP005) in combination with a positive transcription elongation factor b activator, such as JQ1, and a pharmaceutically acceptable excipient. In some embodiments, the present invention provides a pharmaceutical composition including ingenol-3-angelate (PEP005) in combination with a histone methyltransferase (HMT) inhibitor, such as GSK343, and a pharmaceutically acceptable excipient. In some embodiments, the present invention provides a pharmaceutical composition including ingenol-3-angelate (PEP005) and a histone deacetylase (HDAC) inhibitor, such as SAHA, and a pharmaceutically acceptable excipient. In some embodiments, the present invention provides a pharmaceutical composition including ingenol-3-angelate (PEP005) in combination with one or more latency reactivation agents (e.g., JQ1, GSK343, and/or SAHA), one or more viral therapy vaccines (e.g., a CTL booster), and a pharmaceutically acceptable excipient. In some of these embodiments, the pharmaceutically acceptable excipient includes a salt or a diluent.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulfate, and/or (f) absorbents, colorants, flavors and sweeteners. In some embodiments, the tablet contains a mixture of hydroxypropyl methylcellulose, polyethyleneglycol 6000 and titanium dioxide. Tablets may be either film coated or enteric coated according to methods known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

Compositions for pulmonary administration include, but are not limited to, dry powder compositions consisting of the powder of a compound described herein, or a salt thereof, and the powder of a suitable carrier and/or lubricant. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

The compounds can also be formulated in rectal compositions, for example, suppositories or retention enemas, for example, containing conventional suppository bases, for example, cocoa butter or other glycerides.

The compositions set forth herein can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the compound(s) can be in powder form for reconstitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the compound(s).

Furthermore, the compound(s) can be formulated as a depot preparation. Such long-acting formulations can be administered by implantation (e.g., subcutaneously or intramuscularly) or by intramuscular injection. Thus, for example, one or more of the compounds described herein can be formulated with suitable polymeric or hydrophobic materials (e.g., as an emulsion in an acceptable oil) or ion exchange resins, or as sparingly soluble derivatives, for example, as a sparingly soluble salt.

In some embodiments, the compounds are prepared with a polysaccharide such as chitosan or derivatives thereof (e.g., chitosan succinate, chitosan phthalate, etc.), pectin and derivatives thereof (e.g., amidated pectin, calcium pectinate, etc.), chondroitin and derivatives thereof (e.g., chondroitin sulfate), and alginates.

In some embodiments, the compounds are loaded onto polymeric nanoparticles that can target the site of infection. Examples of nanoparticles include biodegradable nanoparticles, pH-sensitive nanoparticles (e.g., comprising Eudragit® S100), trimethylchitosan nanoparticles, polymeric nanoparticles (e.g., comprising PLGA, PEG-PLGA and/or PEG-PCL), and mannose-grafted polymeric nanoparticles. See, e.g., Coco et al., Int. J. Pharm. 440:3-12 (2013).

The compounds can be encapsulated in a controlled drug-delivery system such as a pressure controlled delivery capsule (see, e.g., Takaya et al., J. Control Rel., 50:111-122 (1998)), a colon targeted delivery system, a osmotic controlled drug delivery system, and the like. The pressure controlled delivery capsule can contain an ethylcellulose membrane. The colon target delivery system can contain a tablet core containing lactulose which is over coated with an acid soluble material, e.g., Eudragit E®, and then overcoated with an enteric material, e.g., Eudragit L®. The osmotic controlled drug delivery system can be a single or more osmotic unit encapsulated with a hard gelatin capsule (e.g., capsule osmotic pump; commercially available from, e.g., Alzet, Cupertino, Calif.). Typically, the osmotic unit contains an osmotic push layer and a drug layer, both surrounded by a semipermeable membrane. For a broad overview of delivery systems, see, Banga, A. J., THERAPEUTIC PEPTIDES AND PROTEINS: FORMULATION, PROCESSING, AND DELIVERY SYSTEMS, Technomic Publishing Company, Inc., Lancaster, Pa. (1995), incorporated herein by reference.

Polymers can be used for ion-controlled release of compositions of the present invention. Various degradable and non-degradable polymeric matrices for use in controlled drug delivery are known in the art (see, Langer R., Accounts Chem. Res., 26:537-542 (1993)). For example, the block copolymer, polaxamer 407, exists as a viscous yet mobile liquid at low temperatures but forms a semisolid gel at body temperature. In other embodiments, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)).

In some embodiments, the compositions further include a pharmaceutical surfactant. In other embodiments, the compositions further include a cryoprotectant. Non-limiting examples of cryoprotectants include glucose, sucrose, trehalose, lactose, sodium glutamate, PVP, cyclodextrin, 2-hydroxypropyl-13-cyclodextrin (HPI3CD) glycerol, maltose, mannitol, saccharose, and mixtures thereof.

VII. Methods of Administration

Pharmaceutical compositions or medicaments can be administered to a subject at a therapeutically effective dose to reactivate latent infections by viruses, as described herein. In some embodiments, the pharmaceutical composition or medicament is administered to a subject in an amount sufficient to elicit an effective therapeutic response in the subject. In certain embodiments, the pharmaceutical composition or medicament can be administered to a subject at a therapeutically effective dose to reactivate virally infected cells from latent reservoirs and increase the subject's immune system to combat and kill reactivated virally infected cells.

In some embodiments, the methods of administration comprise administering ingenol-3-angelate (PEP005) alone or in combination with one or more additional latency reactivation agents including positive transcription elongation factor b activators, histone methyltransferase (HMT) inhibitors, histone deacetylase (HDAC) inhibitors, DNA methyltransferase inhibitors, NF-κB activators, Akt/HEXIM-1 modulators, Jak/Stat pathway modulators, diterpene compounds (e.g., ingenol derivatives, phorbol esters), macrolide lactones, diacylglycerol (DAG) lactones, protein kinase C (PKC) activators, and combinations thereof to a patient in need thereof. In some embodiments, the methods of administration can include PEP005 in combination with JQ1, GSK343, SAHA, and combinations thereof.

In some embodiments, ingenol-3-angelate (PEP005) is administered to a patient infected with a virus, such as HIV, to reactivate a latent viral infection.

In some embodiments, ingenol-3-angelate (PEP005) is administered in combination with a positive transcription elongation factor b activator, such as JQ1, to a patient infected with a virus, such as HIV, to reactivate a latent viral infection.

In some embodiments, ingenol-3-angelate (PEP005) is administered in combination with a histone methyltransferase (HMT) inhibitor, such as GSK343, to a patient infected with a virus, such as HIV, to reactivate a latent viral infection.

In some embodiments, ingenol-3-angelate (PEP005) is administered in combination with a histone deacetylase (HDAC) inhibitor, such as SAHA, to a patient infected with a virus, such as HIV, to reactivate a latent viral infection.

In some embodiments, ingenol-3-angelate (PEP005) is administered in combination with a DNA methyltransfase inhibitor to a patient infected with a virus, such as HIV, to reactivate a latent viral infection.

In some embodiments, ingenol-3-angelate (PEP005) is administered in combination with an NF-κB activator to a patient infected with a virus, such as HIV, to reactivate a latent viral infection.

In some embodiments, ingenol-3-angelate (PEP005) is administered in combination with a Akt/HEXIM-1 modulator to a patient infected with a virus, such as HIV, to reactivate a latent viral infection.

In some embodiments, ingenol-3-angelate (PEP005) is administered in combination with a Jak/Stat pathway modulator to a patient infected with a virus, such as HIV, to reactivate a latent viral infection.

In some embodiments, ingenol-3-angelate (PEP005) is administered in combination with a diterpene compound to a patient infected with a virus, such as HIV, to reactivate a latent viral infection.

In some embodiments, ingenol-3-angelate (PEP005) is administered in combination with an ingenol derivative to a patient infected with a virus, such as HIV, to reactivate a latent viral infection.

In some embodiments, ingenol-3-angelate (PEP005) is administered in combination with a phorbol ester to a patient infected with a virus, such as HIV, to reactivate a latent viral infection.

In some embodiments, ingenol-3-angelate (PEP005) is administered in combination with a macrolide lactone to a patient infected with a virus, such as HIV, to reactivate a latent viral infection.

In some embodiments, ingenol-3-angelate (PEP005) is administered in combination with a diacylglycerol lactone to a patient infected with a virus, such as HIV, to reactivate a latent viral infection.

In some embodiments, ingenol-3-angelate (PEP005) is administered in combination with a protein kinase C activator, such as a diterpene compound, to a patient infected with a virus, such as HIV, to reactivate a latent viral infection.

In some embodiments, ingenol-3-angelate (PEP005) is administered with a viral therapy vaccine and optionally one or more latency reactivation agents to a patient infected with a virus, such as HIV, to reactivate a latent viral infection (i.e., latent virally infected cells) and to increase the patient's immune system to combat and kill the reactivated virally infected cells.

The formulations of the present invention are useful in the manufacture of a pharmaceutical composition or a medicament. A pharmaceutical composition or medicament can be administered to a subject in need thereof, e.g. a patient infected with a viral infection, such as, but not limited to HIV, CMV, and adenovirus.

In certain methods of reactivating a latent virus, set forth herein, the methods comprise first administering ingenol-3-angelate (PEP005), to a patient infected with a latent virus, and then administering a positive transcription elongation factor b activator, such as JQ1, to the patient. In certain methods of reactivating a latent virus, set forth herein, the methods comprise first administering a positive transcription elongation factor b activator, such as JQ1, to a patient infected with a latent virus, and then administering ingenol-3-angelate (PEP005) to the patient. In certain other methods of reactivating a latent virus, ingenol-3-angelate (PEP005) and a positive transcription elongation factor b activator, such as JQ1, are administered simultaneously to a patient infected with a latent virus.

In certain methods of reactivating a latent virus, set forth herein, the methods comprise first administering ingenol-3-angelate (PEP005), to a patient infected with a latent virus, and then administering a histone methyltransferase (HMT) inhibitor, such as GSK343, to the patient. In certain methods of reactivating a latent virus, set forth herein, the methods comprise first administering a histone methyltransferase (HMT) inhibitor, such as GSK343, to a patient infected with a latent virus, and then administering ingenol-3-angelate (PEP005) to the patient. In certain other methods of reactivating a latent virus, ingenol-3-angelate (PEP005) and a histone methyltransferase (HMT) inhibitor, such as GSK343, are administered simultaneously to a patient infected with a latent virus.

In certain methods of reactivating a latent virus, set forth herein, the methods comprise first administering ingenol-3-angelate (PEP005), to a patient infected with a latent virus, and then administering a histone deacetylase (HDAC) inhibitor, such as SAHA, to the patient. In certain methods of reactivating a latent virus, set forth herein, the methods comprise first administering a histone deacetylase (HDAC) inhibitor, such as SAHA, to a patient infected with a latent virus, and then administering ingenol-3-angelate (PEP005) to the patient. In certain other methods of reactivating a latent virus, ingenol-3-angelate (PEP005) and a histone deacetylase (HDAC) inhibitor, such as SAHA, are administered simultaneously to a patient infected with a latent virus.

In certain methods of reactivating a latent virus and combating and killing reactivated virally infected cells, set forth herein, the methods comprise first administering a viral therapy vaccine to a patient infected with a latent virus, and then administering ingenol-3-angelate (PEP005) to the patient. In certain other methods of reactivating a latent virus and combating and killing reactivated virally infected cells, set forth herein, the methods comprise first administering a viral therapy vaccine to a patient infected with a latent virus, and then administering ingenol-3-angelate (PEP005) as well as one or more latency reactivating agents to the patient. In certain other methods of reactivating a latent virus and combating and killing reactivated virally infected cells, set forth herein, the methods comprise simultaneously administering a viral therapy vaccine, the ingenol-3-angelate (PEP005), and optionally one or more latency reactivating agents to a patient infected with a latent virus.

In some embodiments, the present invention provides a method of delivering an effective amount of ingenol-3-angelate (PEP005) alone or in combination with one or more additional latency reactivation agents including positive transcription elongation factor b activators, histone methyltransferase (HMT) inhibitors, histone deacetylase (HDAC) inhibitors, DNA methyltransferase inhibitors, NF-κB activators, Akt/HEXIM-1 modulators, Jak/Stat pathway modulators, diterpene compounds (e.g., ingenol derivatives, phorbol esters), macrolide lactones, diacylglycerol (DAG) lactones, protein kinase C (PKC) activators, and combinations thereof to a patient in need thereof.

In some embodiments, the present invention provides a method of delivering an effective amount of a viral therapy vaccine and ingenol-3-angelate (PEP005) alone or in combination with one or more additional latency reactivation agents described herein.

VIII. Dosage

Pharmaceutical compositions or medicaments can be administered to a subject at a therapeutically effective dose to reactivate latent viral infections as described herein. The pharmaceutical composition or medicament is administered to a subject in an amount sufficient to elicit an effective therapeutic response in the subject.

The dosage of compounds administered is dependent on the subject's body weight, age, individual condition, surface area or volume of the area to be treated, and/or on the form of administration. The size of the dose will also be determined by the existence, nature, and extent of any adverse effects that accompany the administration of a particular compound in a particular subject. Typically, a dosage of the active compounds is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies, and repetition rates.

In some embodiments, a unit dosage for oral administration to a subject (e.g., human) of about 50 to about 70 kg may contain between about 1 and about 500 mg, about 5 and about 500 mg, about 5 and about 250 mg, about 25 to about 250 mg, about 100 and about 1000 mg, about 200 and about 2000 mg, about 500 and about 5000 mg, or about 1000 and about 2000 mg of the compound(s). In particular embodiments, a unit dosage for oral administration to a subject (e.g., human) of about 50 to about 70 kg may contain about 5 mg, 10 mg, 15 mg, 20 mg, 25 mg, 30 mg, 35 mg, 40 mg, 45 mg, 50 mg, 75 mg, 100 mg, 200 mg, 300 mg, 400 mg, 500 mg, 600 mg, 700 mg, 800 mg, 900 mg, 1000 mg, 1250 mg, 1500 mg, 2000 mg, 2500 mg, 3000 mg, or more of the compound(s).

In some embodiments, a unit dosage for intravenous administration to a subject (e.g., human) of about 50 to about 70 kg may contain between about 0.1 and about 100 mg, about 0.5 and about 100 mg, about 0.5 and about 50 mg, about 0.5 and about 25 mg, about 0.5 and about 10 mg, about 0.25 to about 50 mg, about 0.25 to about 25 mg, about 0.1 to about 50 mg, about 0.1 to about 25 mg, or about 0.1 to about 10 mg of the compound(s). In particular embodiments, a unit dosage for intravenous administration to a subject (e.g., human) of about 50 to about 70 kg may contain about 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 75 mg, 100 mg, or more of the compound(s).

Exemplary doses of the compositions described herein include milligram or microgram amounts of the composition per kilogram of subject weight (e.g., about 1 microgram per kilogram to about 500 milligrams per kilogram, about 10 micrograms per kilogram to about 5 milligrams per kilogram, about 10 microgram per kilogram to about 500 micrograms per kilogram, or about 1 microgram per kilogram to about 100 micrograms per kilogram. It is furthermore understood that appropriate doses of a composition depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In some embodiments, a pharmaceutical composition or medicament of the present invention is administered orally, e.g., in a dose in the range of from about 1 to about 1000 micrograms (µg) of compound per kg of subject body weight, from about 1 to about 500 µg/kg body weight, from about 10 to about 1000 µg/kg body weight, from about 10 to about 500 µg/kg body weight, from about 50 to about 1000 µg/kg body weight, from about 50 to about 500 µg/kg body weight, from about 100 to about 1000 µg/kg body weight, or from about 100 to about 500 µg/kg body weight. In particular embodiments, the dose is about 10, 25, 50, 75, 100, 200, 300, 400, 500, 600, 700, 800, 900, or 1000 µg/kg body weight. The dose can be administered once per day or divided into sub-doses and administered in multiple doses, e.g., twice, three times, or four times per day. However, as will be appreciated by a skilled artisan, oral compositions described herein may be administered in different amounts and at different times.

In some embodiments, a pharmaceutical composition or medicament of the present invention is administered intravenously, e.g., in a dose in the range of from about 1 to about 500 micrograms (µg) of compound per kg of subject body weight, from about 1 to about 200 µg/kg body weight, from about 1 to about 100 µg/kg body weight, from about 10 to about 500 µg/kg body weight, from about 10 to about 200 µg/kg body weight, from about 10 to about 100 µg/kg body weight, or from about 10 to about 80 µg/kg body weight. In particular embodiments, the dose is about 1, 5, 10, 15, 20, 25, 30, 35, 40, 45, 50, 55, 60, 65, 70, 75, 80, 85, 90, 95, 100, 200, 300, 400, or 500 µg/kg body weight. The dose can be administered once per day or divided into sub-doses and administered in multiple doses, e.g., twice, three times, or four times per day. However, as will be appreciated by a skilled artisan, intravenous compositions described herein may be administered in different amounts and at different times.

In certain embodiments, ingenol-3-angelate (PEP005) is administered orally at a dose between about 100 to about 500 µg/kg body weight. In other embodiments, ingenol-3-angelate (PEP005) is administered intravenously at a dose between about 10 to about 80 µg/kg body weight. In particular embodiments, ingenol-3-angelate (PEP005) is adminstered in combination with one or more additional latency reactivation agents described herein. In some embodiments, each compound may be administered at a dose of the individual compounds that is effective for reactivating a latent virus. In other embodiments, each compound may be administered at a lower dose relative to the dose of the individual compounds that is effective for reactivating a latent virus. Without being bound to any particular theory, it has been found that the administration of a lower dose of one or more additional latency reactivation agents with a lower dose of ingenol-3-angelate (PEP005) is advantageous because such a combination of compounds reduces or eliminates the side-effects associated with the administration of the additional latency reactivation agents at the higher concentrations that are effective for reactivating a latent virus when they are used alone.

In some embodiments, the lower dose of ingenol-3-angelate (PEP005) when used in combination with one or more additional latency reactivation agents is about 100 µg/kg body weight or less for oral administration (e.g., about 1, 5, 10, 15, 20, 25, 30, 35, 40, 45, 50, 55, 60, 65, 70, 75, 80, 85, 90, 95, or 100 µg/kg body weight) or about 10 µg/kg body weight of less for intravenous administration (e.g., about 0.1, 0.2, 0.3, 0.4, 0.5, 0.6, 0.7, 0.8, 0.9, 1, 2, 3, 4, 5, 6, 7, 8, 9, or 10 µg/kg body weight). In other embodiments, the lower dose of the one or more additional latency reactivation agents is reduced by about 25% to about 35% (e.g., by about 25%, 30%, or 35%) compared to the dose of the additional latency reactivation agent alone.

In some embodiments, the compounds are administered one or more times a day, e.g., 1, 2, 3, 4, 5, 6, 7, 8, 9, 10, or more times a day.

In some embodiments, the compounds are administered for about 1 to about 31 days, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the compounds are administered for at least 1 day. In other embodiments, the compounds are administered for one or more weeks, e.g., 1, 2, 3, 4, 5, 6, 7, 8, 9, 10, 11, 12, 13, 14, or more weeks. In yet other embodiments, the compounds are administered for one or more months, e.g., 1, 2, 3, 4, 5, 6, 7, 8, 9, 10, 11, 12, or more months.

To achieve the desired therapeutic effect, compounds may be administered for multiple days at the therapeutically effective daily dose. Thus, therapeutically effective administration of compounds to treat a pertinent condition or disease described herein in a subject requires periodic (e.g., daily or twice daily) administration that continues for a period ranging from three days to two weeks or longer. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every day, every other day, or, if higher dose ranges are employed and tolerated by the subject, twice a week.

Optimum dosages, toxicity, and therapeutic efficacy of such compounds may vary depending on the relative potency of individual compounds and can be determined by standard pharmaceutical procedures in experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While compounds that exhibit toxic side-effects can be used, care should be taken to design a delivery system that targets such compounds to the affected site to minimize potential damage to normal cells and, thereby, reduce side-effects.

The data obtained from, for example, animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration.

A dose can be formulated in animal models to achieve a concentration range that includes the $IC_{50}$ (the concentration of the agent that achieves a half-maximal inhibition of symptoms) as determined in cell culture. Such information can be used to more accurately determine useful doses in humans. Levels in stool or an enteric tissue sample can be measured, for example, by high performance liquid chromatography (HPLC). In general, the dose equivalent of compounds is from about 1 ng/kg to about 100 mg/kg for a typical subject.

The dosage of a pharmaceutical composition of the present invention can be monitored and adjusted throughout treatment, depending on severity of symptoms, frequency of recurrence, and/or the physiological response to the therapeutic regimen. Those of skill in the art commonly engage in such adjustments in therapeutic regimens.

In some embodiments, a pharmaceutical composition or medicament is administered to a patient at a therapeutically effective dose to induce reactivation of latent virally infected cells. The pharmaceutical composition or medicament is administered to a patient in an amount sufficient to elicit an effective therapeutic response in the patient. An effective therapeutic response is a response that at least partially reactivates latent virally infected cells. An amount adequate to accomplish this is defined as a "therapeutically effective dose."

Single or multiple administrations of the compositions are administered depending on the dosage and frequency as required and tolerated by the patient. In any event, the composition should provide a sufficient quantity of the compounds of the invention to effectively treat the patient. Generally, the dose is sufficient to induce viral reactivation from latent virally infected cells without producing unacceptable toxicity or side-effects to the patient.

IX. Kits, Containers, Devices, and Systems

A wide variety of kits and systems can be prepared according to the present invention, depending upon the intended user of the kit and system and the particular needs of the user. In some embodiments, the present invention provides a kit that includes ingenol-3-angelate (PEP005) and one or more additional latency reactivation agents selected from positive transcription elongation factor b activators, histone methyltransferase (HMT) inhibitors, histone deacetylase (HDAC) inhibitors, DNA methyltransferase inhibitors, NF-κB activators, Akt/HEXIM-1 modulators, Jak/Stat pathway modulators, diterpene compounds (e.g., ingenol derivatives, phorbol esters), macrolide lactones, diacylglycerol (DAG) lactones, protein kinase C (PKC) activators, and combinations thereof. In certain embodiments, the kit includes ingenol-3-angelate (PEP005) and a compound selected from JQ1, GSK343, SAHA, and combinations thereof. In certain embodiments, the kit includes ingenol-3-angelate (PEP005) and JQ1. In other embodiments, the kit includes ingenol-3-angelate (PEP005) and GSK343. In yet other embodiments, the kit includes ingenol-3-angelate (PEP005) and SAHA. In other embodiments, the kit includes ingenol-3-angelate (PEP005), one or more additional latency reactivation agents (e.g., JQ1, GSK343, and/or SAHA), and one or more viral therapy vaccines (e.g., CTL booster).

Some of the kits described herein include a label describing a method of administering ingenol-3-angelate (PEP005) and/or one or more additional latency reactivation agents described herein. Some of the kits described herein include a label describing a method of reactivating a latent virus, e.g., HIV, CMV, or adenovirus.

The compositions of the present invention, including but not limited to compositions including ingenol-3-angelate (PEP005), one or more additional latency reactivation agents, and optionally a viral therapy vaccine described herein may, if desired, be presented in a bottle, jar, vial, ampoule, tube, or other container-closure system approved by the Food and Drug Administration (FDA) or other regulatory body, which may provide one or more dosages containing the compounds. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as described herein, a container closure system including the formulation or a dosage unit form including the formulation, and a notice or instructions describing a method of use as described herein.

In some embodiments, the kit includes a container which is compartmentalized for holding the various elements of a formulation (e.g., the dry ingredients and the liquid ingredients) or composition, instructions for making the formulation or composition, and instructions for administering the formulation or composition for reactivating a latent virus such as, e.g., HIV, CMV, adenovirus, or combinations thereof.

In certain embodiments, the kit may include the pharmaceutical preparation in dehydrated or dry form, with instructions for its rehydration (or reconstitution) and administration.

Kits with unit doses of the compounds described herein, e.g. in oral, rectal, transdermal, or injectable doses (e.g., for intramuscular, intravenous, or subcutaneous injection), are provided. In such kits, an informational package insert describing the use and attendant benefits of the composition for reactivating a latent virus may be included in addition to the containers containing the unit doses.

Some embodiments of the present invention include packages that include ingenol-3-angelate (PEP005) and one or more additional latency reactivation agents.

Some other embodiments of the present invention include packages that include ingenol-3-angelate (PEP005), one or more additional latency reactivation agents (e.g., JQ1, GSK343, and/or SAHA), and one or more viral therapy vaccines (e.g., CTL booster).

X. Example

The following example is offered to illustrate, but not to limit, the claimed invention.

Example 1. Synergistic Reactivation of Latent HIV Expression by ingenol-3-angelate, PEP005, Targeted NF-κB Signaling in Combination with JQ1 Induced p-TEFb Activation Although anti-retroviral therapy (ART) is highly effective in suppressing HIV replication, it fails to eradicate the virus from HIV-infected individuals. Stable latent HIV reservoirs are rapidly established early after HIV infection. Therefore, effective strategies for eradication of the HIV reservoirs are urgently needed. This example demonstrates that ingenol-3-angelate (PEP005), the only active component in a previously FDA approved drug (PICATO) for the topical treatment of precancerous actinic keratosis, can effectively reactivate latent HIV in vitro and ex vivo with relatively low cellular toxicity. Biochemical analysis showed that PEP005 reactivated latent HIV through the induction of the pS643/S676-PKCδ/θ-IκBα/ε-NF-κB signaling pathway. Importantly, PEP005 alone was sufficient to induce expression of fully elongated and processed HIV RNAs in primary CD4+ T cells from HIV infected individuals receiving suppressive ART. Furthermore, PEP005 and the P-TEFb agonist, JQ1, exhibited synergism in reactivation of latent HIV with a combined effect that is 7.5-fold higher than the effect of PEP005 alone. Conversely, PEP005 suppressed HIV infection of primary CD4+ T cells through down-modulation of cell surface expression of HIV co-receptors. As such, this example demonstrates that PEP005 is a safe and effective compound for HIV eradication strategies.

INTRODUCTION

Anti-retroviral therapy (ART) is effective in suppressing HIV replication but it fails to eliminate latent viral reservoirs in HIV infected resting CD4+ T cells which, in blood, consist mainly of central and transitional memory CD4+ T cells [1-4]. Current ART options do not eradicate HIV from infected cells. In addition, these cells are invisible to the virus-specific immune responses in the setting of viral latency [5,6]. The viral reservoir is rapidly seeded and HIV latency might be established immediately after virus infection [7,8]. Despite initiation of ART in infants within hours of birth to HIV infected mothers, stable viral reservoirs were established and viral rebound occurred when therapy was interrupted [9]. In the simian immunodeficiency virus (SIV) model of AIDS, stable viral reservoirs are established within 2.5 days of infection [10]. The viral reactivation was detected in rhesus macaques following therapy interruption despite the initiation of ART at 3 days post SIV infection [10,11]. Collectively, these studies demonstrate that a very early initiation of ART may not be sufficient to prevent nor eliminate latent virus reservoirs [9,11,12]. It has been observed that the morbidity of HIV persistence in HIV-positive individuals on long-term ART includes drug toxicities and a higher risk of developing complications including dyslipidemia, cardiovascular disease and insulin resistance [13-15]. Therefore, a therapeutic cure of HIV is urgently needed that leads to viral eradication and experimental strategies for directly targeting HIV latent reservoirs are warranted.

Recent studies have explored an experimental strategy for viral eradication of HIV infected CD4+ T cells by activating HIV transcription and viral antigen expression from the latent viral reservoirs in the presence of ART [6]. This would lead to the detection and clearance of infected cells by the virus-specific host immune responses while the ART prevents new rounds of infection. Cytopathic effects of the viral reactivation would further increase the clearance of the latent viral reservoir. This "shock and kill" strategy was applied in a pilot clinical trial using the histone deacetylase (HDAC) inhibitor, vorinostat, in patients receiving suppressive ART [16-18]. The findings from these studies showed some promise but failed to result in significant clearance of residual HIV reservoirs. Potential mechanisms of this failure include the modest induction of HIV by this earlier generation of latency reversing agents (LRAs) used singly and due to immune defects in clearance of infected cells in spite of the reactivation of viral expression [19,20]. These studies demonstrate an urgent need for the development of new strategies both for disrupting HIV latency and facilitating elimination of infected cells after HIV expression is reactivated.

Several cell signaling pathways are critical for the establishment and maintenance of HIV latency [6,21,22]. Disruption of one or more of these pathways could lead to effective reactivation of HIV from latency. Various compounds have been tested for the disruption of HIV latency, and those inducing HIV reactivation from the viral long terminal repeat (LTR) through the stimulation of the protein kinase C (PKC)-NF-κB pathway showed high potency. These include phorbol esters (PMA and prostratin) and non-phorbol ester diterpenes (bryostatin and gnidimacrin) that induce NF-κB nuclear translocation and activation through the PKC pathway [22,23]. Some of these compounds effectively induce latent HIV reactivation in vitro at picomolar levels [24,25]. The LRAs, functioning through the PKC-NF-κB signaling, are able to reactivate latent HIV across a broad range of HIV latency models [20]. A recent study showed that LRAs stimulating PKC-NF-κB signaling may be most effective in inducing complete transcription of HIV from resting CD4+ T cells of HIV infected individuals on suppressive ART [26]. Moreover, these compounds cause down-modulation of the expression of cell surface receptors, CD4, CXCR4 or CCR5, and protect cells against HIV infection [22]. Therefore, LRAs that activate PKC-NF-κB signaling are potential candidates for HIV cure studies. We previously reported that an ingenol ester, ingenol-3-hexanoate or IngB, is an excellent candidate for the reactivation of HIV from latency [24]. The modified ingenol-3-hexanoate was originally isolated from an Amazonian plant, *Euphorbia tirucalli*. It exerts low toxicity in CD4+ T cells and does not induce global T-cell activation. It caused reactivation of latent HIV at nanomolar levels [24]. However, since IngB induces expression and activation of both NF-κB and CyclinT1/CDK9, and stimulates IFNγexpression in primary CD4+ T cells, further search for new ingenol compounds with better HIV reactivation potential and lower cellular toxicity is needed [24, 27, 28].

Among previously identified ingenol compounds, ingenol-3-angelate (PEP005) is currently approved for clinical use. A recently FDA approved drug, PICATO, for the topical treatment of precancerous actinic keratosis contains ingenol-3-angelate as an active component [29]. A prior study suggested that ingenol-3-angelate could induce HIV expression from the U1 monocyte cell line harboring HIV genome [30]. In the current study, we report that PEP005 can effectively reactivate latent HIV through the activation of the pS643/S676-PKCδ/θ-IκBα/ε-NF-κB pathway in an HIV latency model in vitro but does not induce or increase NF-κB protein production by itself. It also reactivated full-length HIV transcription based on an assay targeting the poly A tail region of HIV transcripts in cells from ART-suppressed HIV-positive individuals, while exerting minimal toxicity and effects on T cell activation ex vivo [26]. Importantly, the effect of PEP005 was synergistic with JQ1, a p-TEFb activator, and the combination was highly potent in reactivating latent HIV expression both in vitro and ex vivo. Our findings identify this anti-cancer drug, PEP005, as having a distinct mechanism of molecular signaling and as a compound for advancing HIV eradication strategies.

Materials and Methods

Cell Culture:

J-Lat A1 cells (harboring a single copy of latent HIV LTR and one copy of green fluorescent protein gene under the HIV LTR control) or U1 cells (harboring two latent HIV genomes with defective Tat gene) were cultured in RPMI1640 medium with 10% fetal bovine serum (FBS) and 1% Pen/strep in a 37° C. incubator containing 5% $CO_2$ [24,31]. Both of the cell lines were obtained from NIH AIDS Reagent Program. For reactivation of HIV LTR, cells were treated with PMA (Sigma), JQ1 (Biovision), Prostatin (Sigma), SAHA (Santa Cruz), TNF-α (BD), GSK343 (Sigma), or PEP005 (Tocris Bioscience) for 24 h. HIV reactivation was quantified by GFP expression using flow cytometry and the data were analyzed using FlowJo Software for J-Lat A1 cells, or by quantitative RT-PCR (RT-qPCR) for J-Lat A1 and U1 cells. Cell viability was evaluated using Live/Dead dye (Life Technologies) by flow cytometry. So far, there is not a single in vitro cell culture model available that captures all the features of HIV latency. However, PKC agonists seem to reactivate latent HIV in all the cell culture models of viral latency. Similar to other J-Lat cell lines, the J-Lat A1 clone has been widely used by researchers for HIV latency studies. The T-cell-derived J-Lat A1 cells harbor one copy of a construct containing a Tat and a green fluorescent protein (GFP) gene framed by the 5' and 3' HIV LTR [32]. The J-Lat A1 cells also contain the TAR loop located within the R region of HIV LTR (nt +1 to +60), which provides an opportunity for Tat-TAR interactions for the modulation of transcription and transcriptional elongation. Consequently, the J-Lat A1 cell model is a suitable cell culture model to investigate latency reversal by PKC agonists.

Primary CD4+ T Cell Isolation and Detection of T Cell Activation Markers:

Peripheral blood samples were collected from 13 HIV-infected individuals receiving suppressive ART for >3 years except for one patient. All subjects had suppression of plasma viremia for more than 6 months (Average 5.84 years). At the time of the study enrollment, CD4+ T cell counts in peripheral blood samples ranged from 264 to 1100 cells/mm$^3$ (Average 639 cell/mm$^3$) and plasma viral loads were <20 copies per ml as measured by qPCR (Table 1). Isolation of the peripheral blood mononuclear cells (PBMC) and purification of CD4+ T cells using the EasySep kit (STEMCELL Technologies Inc. Vancouver, BC, Canada) were performed as previously described [24]. The purified CD4+ T cells were plated at a density of 1×10$^6$ cells/ml and treated with 200 ng/ml PMA plus 2 μM Ionomycin, 6-12 nM PEP005, 2 μM of JQ1, or 12 nM PEP005 plus 2 μM JQ1 for 6 hrs or 48 hrs and the cells were collected for RNA purification. To measure changes in the cell activation status of CD4+ and CD8+ T cell subsets, PBMCs were isolated from uninfected controls and 2×10$^6$ cells were incubated with DMSO, 200 ng/ml PMA plus 2 μM Ionomycin, 6-12 nM PEP005 for 24 hrs or 72 hrs, and immunostained with anti-CD3, anti-CD38, anti-CD69, or anti-HLA-DR antibodies (Biolegend) for 20 min at 4° C. Cells were fixed in 1% PFA and analyzed by flow cytometry (FlowJo software from TreeStar). In addition, PBMCs from HIV-negative uninfected controls were similarly treated for 24 or 72 hrs and cells were collected for cytokine analysis using RT-qPCR.

TABLE 1

Characteristics of HIV-positive individuals receiving HAART

| Patients | Age | Sex | Viral load | CD4 count | ART | Time under ART (years) |
|---|---|---|---|---|---|---|
| 2040 | 45 | M | <20 | 347 | Tenofovir/Emtricitabine/Raltegravir | 4 |
| 2041 | 56 | M | <20 | 1095 | Emtricitabine/tenofovir/efavirenz | 7 |
| 2044 | 60 | F | <20 | 1100 | Emtricitabine/tenofovir/efavirenz | 8 |
| 2050 | 48 | M | <20 | 757 | Emtricitabine/tenofovir/efavirenz | 8 |
| 2051 | 56 | M | <20 | 368 | Emtricitabine/tenofovir/efavirenz | 5 |
| 2052 | 35 | M | <20 | 264 | Lopinavir/Ritonavir | 4 |
| 2053 | 50 | M | <20 | 260 | Atazanavir/Ritonavir | 6 |
| 2054 | 53 | M | <20 | 477 | Emtricitabine/tenofovir/efavirenz | 12 |
| 2055 | 45 | M | <20 | 736 | Tenofovir/Emtricitabine/Atazanavir/Ritonavir | 6 |
| 2056 | 63 | M | <20 | 510 | Nevirapine/Tenofovir/Emtricitabine | 5 |
| 2057 | 55 | M | <20 | 775 | Tenofovir/Emtricitabine/Atazanavir/Ritonavir | 3 |

TABLE 1-continued

Characteristics of HIV-positive individuals receiving HAART

| Patients | Age | Sex | Viral load | CD4 count | ART | Time under ART (years) |
|---|---|---|---|---|---|---|
| 2060 | 57 | M | <20 | 813 | Atazanavir/Ritonavir/ Tenofovir/Emtricitabine | 6 |
| 2061 | 57 | M | <20 | 805 | Elvitegravir/Cobicistat// Emtricitabine/Tenofovir | 2 |

Cell Viability and Proliferation Measurements:

Cells were placed in 96-well plates and incubated for 24 or 72 h hrs with compounds. Cell viability was measured using MTT assay (Roche Laboratories), and cell proliferation/S-phase progression was determined by using BrdU ELISA kit (Cell signaling, #1863).

Immunoblot Analysis:

One million J-Lat A1 cells or PBMCs from HIV-negative uninfected controls were incubated with 12 nM PEP005 for 6 hrs. Whole cell protein extracts were prepared with RIPA buffer containing proteinase inhibitors and phosphatase inhibitors (Sigma). Expression of the isoforms of PKC protein or NF-κB/p65 was evaluated using the PKC Isoform Sampler Antibody Kit (Cell Signaling, 9960S) or anti-NF-κB/p65 (Abcam). The level of phosphorylation of PKC was determined using anti-Phospho-Ser664-PKCδ, anti-Phospho-Ser643/676 PKCδ or anti-Phospho-T538-PKCθ (Millipore), and the level of phosphorylation of IκB was determined using p-IκBα(Ser32), p-IκBβ (Thr19/Ser23) or p-IκBε(Ser18/22) antibodies (Millipore).

HIV RNA Quantification in Patient Samples: Total RNA was extracted using the Qiagen RNeasy Kit that included a DNA digestion step. Quantitative RT-PCR was performed using Taqman Fast Virus 1-Step Master Mix (Applied Biosystems) in a ViiA7 real-time PCR system (Applied Biosystems). Transcripts containing the U5 region of the 5' LTR were amplified using well-conserved primers (HXB2 559-543, 626-643) and fluorescent probe (HXB2 559-584) [24, 33]. Transcripts containing the U3 to R region of the 3' LTR including a Poly A tail were amplified in a one-step RT-PCR procedure related to a recently published assay with primers and probe binding sites as follows: gccctcagatgctrcatataa (SEQ ID NO:8) (HXB2 9496-9516), tttttttttttttttttttttttttgaag (SEQ ID NO:1) (9632-9636+poly T) and FAM-tgcctg-tactgggtctctctggttag-MGB (SEQ ID NO:2) (HXB2 9529-9554) [26,34]. External HIV RNA standards were prepared from in vitro transcripts quantified by spectrophotometry.

Quantitative Analysis of Synergy of Latency Reversing Agent Combinations:

We adapted the Bliss independence model as implemented by Laird et al. to test for synergy when PEP005 was combined with other latency reversing agents [35,36]. For drugs x and y, we used the equation $fa_{xy,P}=fa_x+fa_y-(fa_x)(fa_y)$, where $fa_{xy,P}$ represents the predicted fraction affected by the combination of drug x and drug y given the observed effects of drug x ($fa_x$) and drug y ($fa_y$) used individually and $fa_{xy,O}$=the observed effect when x and y were tested together. Calculation of $fa_x$ for U1 cells and patient derived T cells followed the approach of Laird for intracellular HIV RNA: $fa_x$=(HIV RNA copies with drug x−background copies with DMSO)/(HIV RNA copies with PMA−background copies with DMSO). For these analyses, we included data for which every parameter for the synergy analysis was available and excluded individual cases where some of the parameters were not available. In cases where one or more experimental drug conditions resulted in RNA expression exceeding the PMA condition, we imputed the highest HIV RNA value in that experiment +1 to represent the denominator for calculation of $fa_x$. The calculation of $fa_x$ for J-Lat A1 cells used the % GFP positive cells in place of intracellular HIV RNA. With this model, $\Delta fa_{xy}=fa_{xy,O}$ (the observed fraction affected by the drug combination)−$fa_{xy,P}$ (the predicted fraction affected by the drug combination) provides an indication of synergy ($\Delta fa_{xy}>0$), additive effect (Bliss independence) ($\Delta fa_{xy}=0$) or antagonism ($\Delta fa_{xy}<0$). Calculations analyzing synergy were done using Python. Statistical significance was determined using a one tailed ratio t-test executed in the statistical package "R".

Chromatin immunoprecipitation (ChIP): ChIP assay was performed as previously described [24,37]. Briefly, $1\times10^6$ J-Lat A1 cells were incubated with PEP005, or PKCδ/θ inhibitor (PKGδi, Millipore/Calbiochem), fixed in 1% formaldehyde then resuspended in lysis buffer containing 1% SDS, 10 mM EDTA, 50 mM Tris-HCl, pH 8.1 (ChIP Assay Kit, Millipore) and protease inhibitor cocktail (Sigma-Aldrich). Lysates were sonicated to obtain DNA fragments of 200-1500 bp. The immune complex was retrieved by incubating for 45 min with 50 μl of protein A/G-agarose beads saturated with BSA/salmon sperm DNA. Following the washes, the chromatin was eluted and reverse cross-linked overnight. DNA was extracted (Qiagen PCR purification kit) and quantitative real-time PCR was performed using Agilent Brilliant Ultra-Fast SYBR Green QPCR reagent using the 7500 real-time PCR System. The upstream primer sequence was 5'-AGCTTGCTACAAGGGACTTTCC-3' (SEQ ID NO:3), and the downstream primer sequence was 5'-AC-CCAGTACAGGCAAAAAGCAG-3' (SEQ ID NO:4).

Real-time PCR analysis of GFP or HIV gene expression: Total RNA was isolated from J-Lat A1 cells or U1 cells using the RNeasy Kit (Qiagen) followed by digestion with DNase I (Invitrogen). First strand cDNA was synthesized using Superscript II (Invitrogen). Real-time PCR (TaqMan) was performed on a ViiA 7 detector using the following primer/probe set: for J-Lat A1 cells, primer 1: 5'-GGAGC-GACCATCTTCTTCA-3' (SEQ ID NO:5), primer 2: 5'-AGGGTGTCGCCCTCGAA-3 ' (SEQ ID NO:6), probe 5'-FAM CTACAAGACCC GCGCCGAGGTG TAMRA-3' (SEQ ID NO:7), for U1 cells HIV 5' LTR primers/probe were used (see above) [24]. The GAPDH primer/probe set was purchased from Applied Biosystems.

Pre-Treatment of Primary CD4+ T Cells with PEP005 and HIV-1 Infection of Primary CD4+ T Cells:

Primary CD4+ T cells were isolated from peripheral blood samples of healthy HIV-negative donors and were pre-treated with PEP005 overnight. The CD4+ T cells were infected with HIV-1 (HIV-1 IIIB expanded in Jurkat T cells, 100 ng p24-gag) through spinoculation as described previously [38]. Following an exposure of 24 hrs to HIV, the cells were washed. Cell supernatants were collected and HIV p24 levels were measured by ELISA. The cells were also collected for RNA extraction and measurement of viral transcripts by RT-qPCR.

Statistical Analysis:

Means and standard errors (SE) were calculated for all data points from at least 3 independent experiments in triplicates. Statistical significance was determined using the two-way Student t test, where p value<0.05 considered significant.

Results

PEP005 Induces HIV Expression in an HIV Latency Cell Culture Model In Vitro.

In order to determine the potential of PEP005 to induce HIV expression, J-Lat A1 cells, an established HIV latency lymphocyte cell culture model in vitro [24,32,39], were treated with increasing concentrations (2-40 nM) of PEP005 (FIG. 1A). PEP005 induced HIV expression in a dose-dependent manner and in the absence of any apparent cellular toxicity. A 7-fold increase in the reactivation of HIV latency was detected in J-Lat A1 cells at 20 nM of PEP005 as compared to untreated controls (FIGS. 1B and 1C). The effect of PEP005 on HIV expression was evident even at the 2 nM level. Compared to other compounds known to reactivate HIV from latency, PEP005 appeared to be more potent than SAHA (a histone deacetylase inhibitor), JQ1 (a BET bromodomain inhibitor) and GSK343 (an inhibitor of EZH2) (FIG. 1D). At the 10 nM level, PEP005-induced HIV reactivation was similar to that induced by PMA and more potent than 2 μM Prostratin (p=0.012). Interestingly, although EZH2 was shown to be critical for establishment of HIV latency through tri-methylation of H3K27 and inhibition of EZH2 by 3-deazaneplanocin A (DZNep) resulted in reactivation of latent HIV in vitro [40], the specific EZH2 inhibitor, GSK343 (recently developed by GSK) [41,42], failed to induce HIV expression in J-Lat A1 cells (FIG. 1D). Taken together, these data show that PEP005 is highly potent in reactivating latent HIV in vitro.

The Effect of PEP005 on Reactivation of Latent HIV is Potently Enhanced by Combination with JQ1 in Both J-Lat A1 Cells and U1 Cells In Vitro.

Several molecular pathways are involved in the establishment and maintenance of HIV latency [6,21]. In order to optimally reactivate latent HIV expression, we utilized combinations of latency reversing agents (LRAs) in the J-Lat A1 cells and U1 cells in vitro [43]. Several compounds were selected including the HDAC inhibitor, SAHA (500 nM); the BET bromodomain inhibitor, JQ1 (2 μM); the EZH2 inhibitor, GSK343 (2 μM); and the PKC agonist Prostratin (10 in combination with PEP005 (6 nM). A lower concentration of PEP005 was used in these assays since PEP005 is very potent in reactivating latent HIV expression (FIG. 1D) and the combined effects of it with other LRAs would be difficult to distinguish at a higher concentration of PEP005 [24]. PEP005 induced reactivation of latent HIV and was highly effective in combination with JQ1 in J-Lat A1 cells (FIG. 2A). Surprisingly, GSK343 alone could not effectively induce HIV expression but was able to enhance the magnitude of latent HIV reactivation by PEP005. These findings indicate that pre-disruption of H3K27Me3-mediated chromatin repression may be required for enhanced latent HIV reactivation. Interestingly, Prostratin also showed a trend for enhancing effect of PEP005 on latent HIV reactivation. However, this was not statistically significant.

To determine whether the combined effects of PEP005 on latent HIV reactivation occurs in other latent HIV-infected immune cell types, we examined HIV transcription in U1 cells, a well-studied promonocyte cell line that harbors two complete HIV genomes with Tat gene mutations and is used as an HIV latency cell culture model [31]. While PEP005 alone induced about 25-fold increase in latent HIV reactivation compared to controls, addition of JQ1 boosted induction of HIV transcription to more than 250-fold increase (FIG. 2B). We found a combined effect of PEP005 on reactivation of HIV latency with GSK343, as well as with SAHA in U1 cells. We previously reported a similar pattern of synergy when J-Lat A1 cells were treated with IngB and JQ1 [24].

Our data indicated that PEP005 synergistically reactivates latent HIV in both J-Lat A1 cells and U1 cells. To assess whether these combined effects meet criteria for drug synergy, we compared the experimentally observed combined effects in J-Lat A1 cells and U1 cells to the effects predicted under the Bliss independence model for combined drug effects ([35] and FIGS. 2C and 2D). This model assumes that if two compounds act through different mechanisms, their effects are merely additive in the absence of synergistic interactions. In contrast, effects of combinations that are greater or lesser than the idealized Bliss independence prediction imply synergy or antagonism, respectively [31]. We found that PEP005 demonstrates significant synergism with JQ1 or EZH2 inhibitors to induce GFP expression in vitro (FIG. 2C). HDAC inhibitor SAHA and another PKC agonist Prostratin did not exhibit synergy with PEP005. In U1 cells, PEP005 synergized significantly with JQ1 or SAHA to induce HIV mRNA expression in vitro (FIG. 2D), but GSK343 did not exhibit synergy with PEP005. Taken together, PEP005 exerted a synergistic effect with JQ1 on reactivation of HIV from latency in both J-Lat A1 and U1 cell lines.

PEP005 Disrupts HIV Latency Through IκBα/ε-pSer664/Ser676-PKCδ/θ-NF-κB Signaling.

Figure 3:
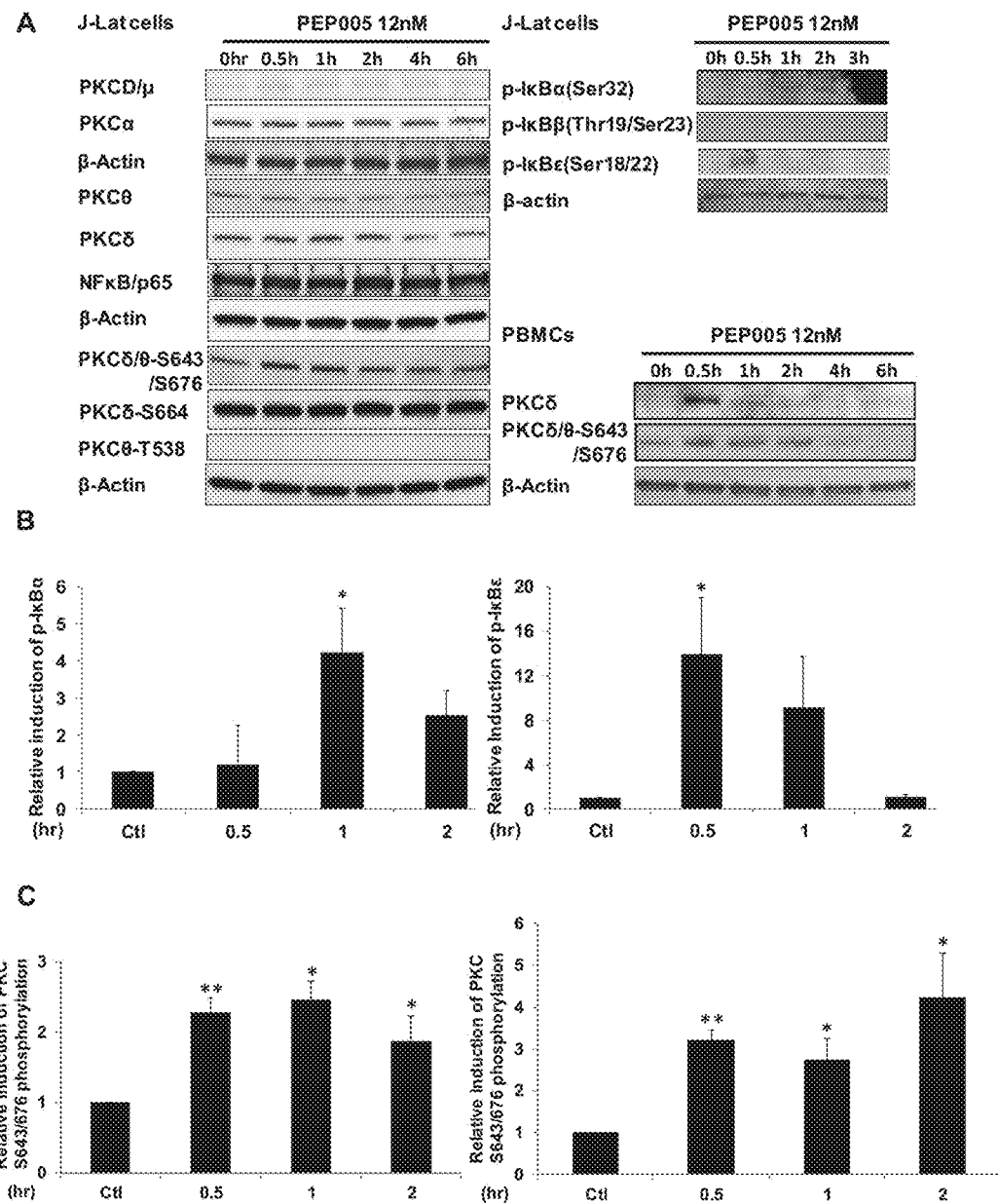
FIG. 3: PEP005 activates PKCδ/θ-IκBα/ε-NF-κB signaling. (A) J-Lat A1 cells or PBMCs isolated from peripheral blood of healthy HIV-negative individuals were treated with 12 nM of PEP005 for up to 6 hours. Western blot analysis was performed to detect the expression of PKC isoforms, IκB isoforms, as well as expression of NF-κB/p65. (B) Quantitation of phosphorylation of IκBα or IκBε in J-Lat A1 cells after 2 hr treatment with PEP005 in panel A. Relative band intensities from three independent experiments in J-Lat A1 cells as determined using ImageJ (NIH) are shown in the bar graph. * $p<0.05$. (C) Quantitation of PKCδ/θ S643/S676 phosphorylation after 2 hr treatment of PEP005 in panel A. Relative band intensities from three independent experiments in J-Lat A1 cells (Left panel) or PBMCs (Right panel) as determined using ImageJ (NIH) are shown in the bar graph. * $p<0.05$, ** $p<0.01$.
Figure 4:
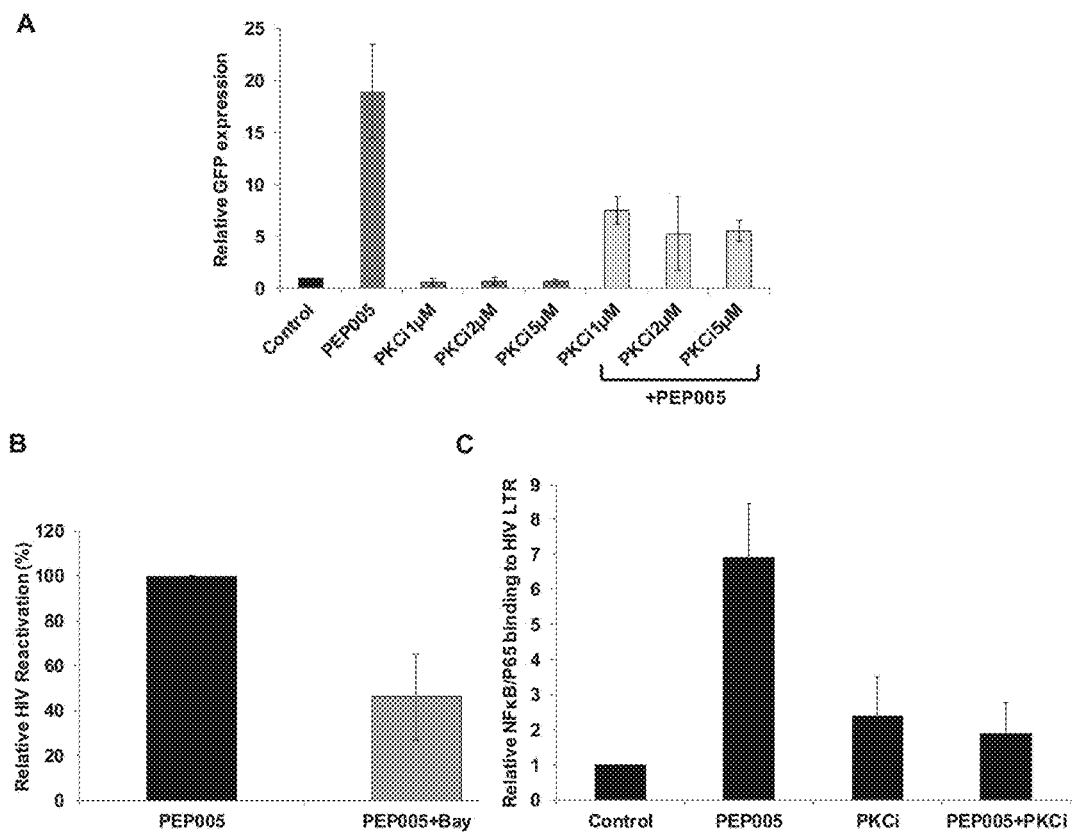
FIG. 4: PEP005-induced HIV reactivation is mediated through PKCδ/θ-IκBα/ε-NF-κB signaling. (A) PEP005-induced HIV reactivation is suppressed by inhibition of the PKCδ/θ. J-Lat A1 cells were treated with 6 nM of PEP005 in the presence of 1, 2 or 5 µM of PKC inhibitor (PKCθ/δ inhibitor; Milipore/Calbiochem (539649)) and evaluated for GFP expression by RT-qPCR. (B) NF-κB inhibition partially suppresses PEP005-induced HIV reactivation in J-Lat A1 cells. J-Lat A1 cells were treated with 6 nM of PEP005 in the presence of 2.5 µM Bay 11-7082, an NF-κB inhibitor, and were evaluated for GFP expression by RT-qPCR. (C) J-Lat A1 cells were treated with PEP005 or alternatively with PKC inhibitor alone or in the presence of PEP005 and the relative binding of NF-κB to the HIV LTR was determined using ChIP-qPCR.

Although it was shown that PEP005 can activate the PKC-NF-κB pathway, it is not known at which step of the PKC-NF-κB pathway is modulated during the reactivation of latent HIV. Therefore, we examined protein expression of several components of the PKC pathway in J-Lat A1 cells by Western blot analysis using antibodies specific for four PKC super families, including PKCμμ/D, PKCα, PKCδ, and PKCθ. There was no significant induction of expression of these PKC proteins except for a modest up-regulation of PKCδ that was detected at 1 hr following 12 nM PEP005 treatment. Moreover, rapid phosphorylation of Ser643/Ser676 in PKCδ/θ was induced by PEP005 with greater than a two-fold increase as early as 30 minutes post treatment (FIGS. 3A-C). These findings were further validated in PEP005 treated PBMCs from healthy donors. To investigate the involvement of the up-stream kinases in PKC-NF-κB signaling, Western blot analysis was performed using anti-phospho-IκB antibodies. Our data showed that PEP005 treatment induced phosphorylation of IκBα and IκBε, but not of IκBβ (FIGS. 3A-B). Interestingly, expression of NF-κB/p65 did not change in the presence of PEP005 (FIG. 3A). This is clearly different from the effects of IngB treatment which involved an increased expression of NF-κB/p65 protein [24]. To further confirm the role of PKC-NF-κB signaling in reactivation of HIV latency, J-Lat A1 cells were treated with a PKCθ/δ inhibitor (FIG. 4A). Our data showed that inhibition of PKCθ/δ resulted in a reduction of latent HIV reactivation by more than 65%. The addition of the NF-κB inhibitor, Bay-11-7082, to J-Lat A1 cells resulted in an approximately 50% reduction in PEP005-induced disruption of HIV latency (FIG. 4B). To determine whether PEP005 reactivates latent HIV by promoting NFκB/p65 binding to the HIV LTR, ChIP-qPCR assays were performed with J-Lat A1 cells treated with 12 nM of PEP005 with or without PKCδ/θ inhibitor. PEP005 treatment resulted in a 6-fold increase in NF-κB/p65 binding to HIV LTR region (FIG. 4C). This increase was reduced by more than 70% following the addition of PKC inhibitor. Collectively, our findings indicate that PEP005-induced reactivation of latent HIV most likely occurs through the PKCδ/θ-NF-κB signaling pathway. However, this does not exclude a possibility that other PKC isoforms are also potentially involved.

PEP005 Displays Minimal Toxicity in Primary CD4+ T Cells.

Figure 5:
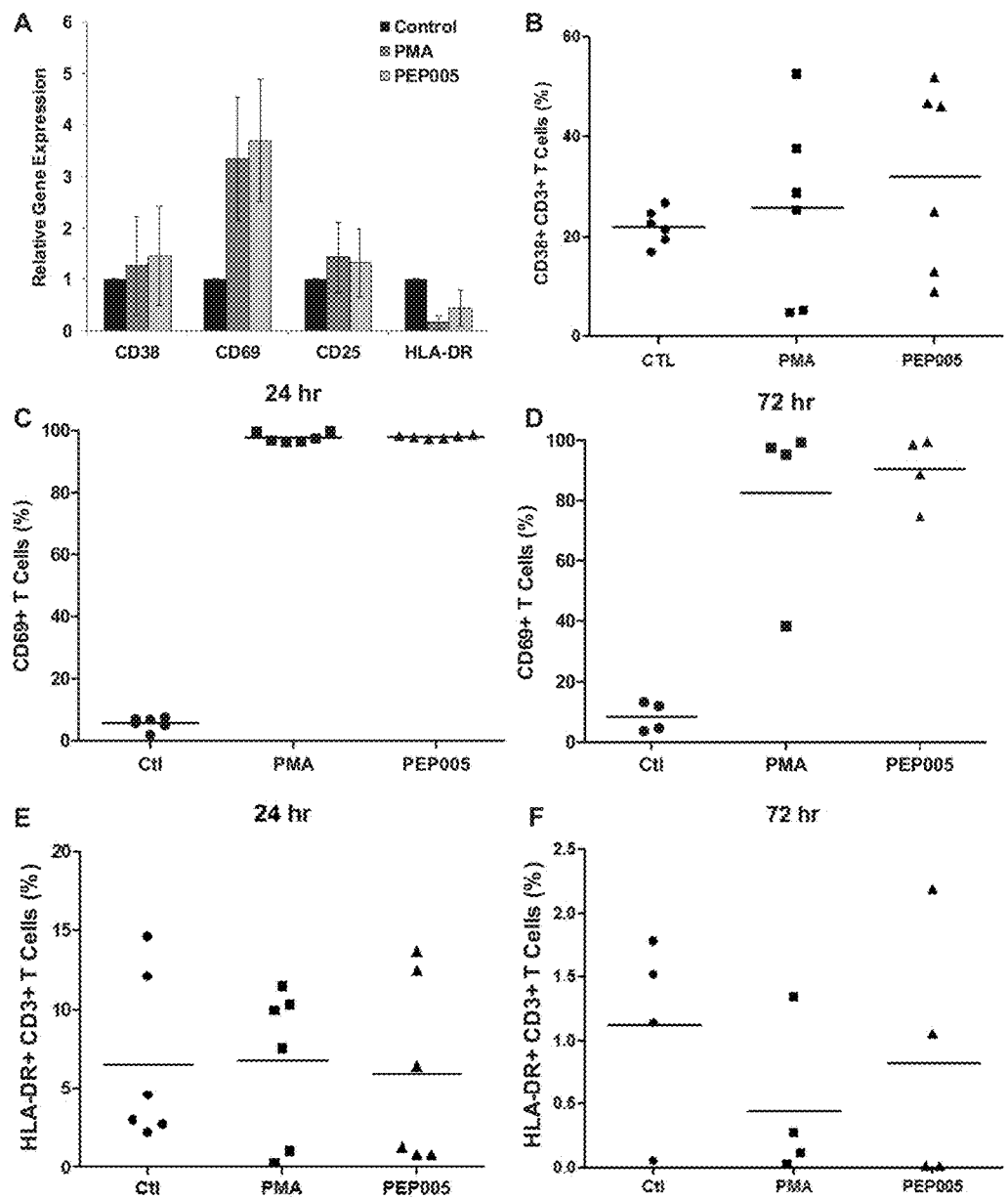
FIG. 5: Expression of T cell activation markers in PEP005-treated primary CD4+ T cells. (A) CD4+ T cells were isolated from uninfected control subjects and treated with 12 nM PEP005 for 24 hrs. Total RNA was extracted, and gene expression of CD38, CD69, CD25, or HLA-DR was analyzed by RT-qPCR. (B-F) PBMCs isolated from peripheral blood of healthy HIV-negative donors were treated for 24 or 72 hours with 12 nM of PEP005, and the expression of CD38 (B), CD69 (C, D), and HLA-DR (E, F) was evaluated using flow cytometry after co-staining with the CD3 T cell marker.
Figure 6:
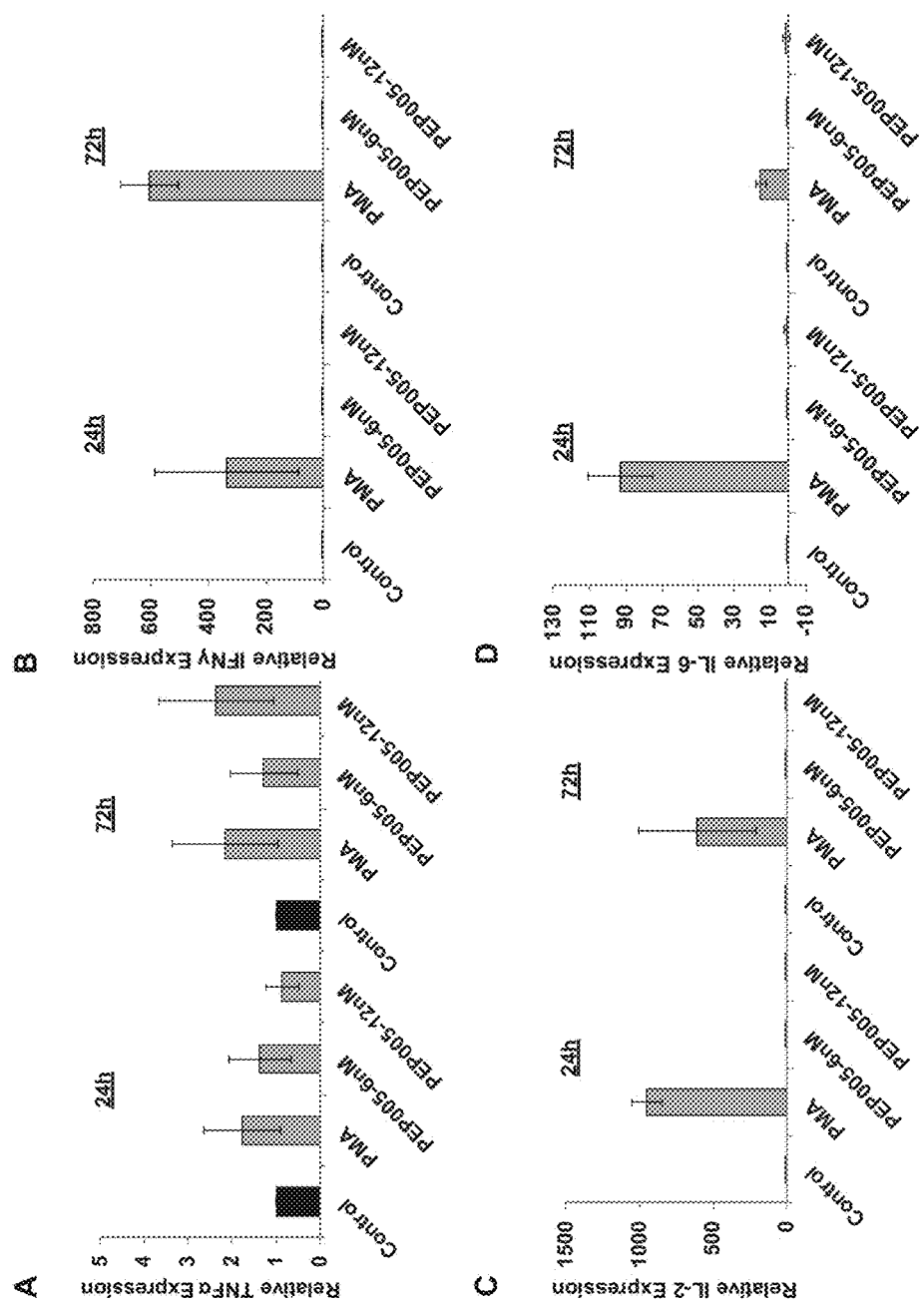
FIG. 6: PEP005 does not induce expression of pro-inflammatory cytokines in primary CD4+ T cells from peripheral blood of HIV-negative donors. CD4+ T cells were isolated from healthy donors and treated with 6 or 12 nM of PEP005 for 24 or 72 hours, and the relative expression of TNF-α (A), IFN-γ (B), IL-2 (C), and IL-6 (D) was quantified using RT-qPCR and normalized to GAPDH internal control.

To be clinically applicable, effective LRAs should be highly potent, minimally cytotoxic and able to penetrate anatomic sanctuaries and immune cell types without inducing global T cell activation [22]. Therefore, we sought to examine the effects of PEP005 on T cell activation and cytotoxicity. Evaluation of the expression of T cell activation biomarkers by RT-qPCR showed that PEP005 treatment did not cause any significant change in the expression of CD38, CD25, or HLA-DR in purified primary CD4+ T cells (FIG. 5A). However, there was an increased expression of CD69 in CD4+ T cells. Flow cytometric analysis of global T cells for the expression of CD38, CD69, or HLA-DR further supported the gene expression data. There was no significant change in the expression of CD38 (24 hr) and HLA-DR in CD4+ T cells (FIGS. 5B, 5E and 5F). However, there was an increase in expression of CD69, an inducible glycoprotein that is expressed early during T lymphocytes activation (FIGS. 5C and 5D). These findings provide additional evidence that PEP005 reverses HIV latency through PKC-NF-κB signaling in vivo. Since the expression of CD69 is dependent on NF-κB binding to its promoter region, it is understandable that PEP005 induced PKC-NF-κB signaling would up-regulate CD69 expression in CD4+ T cells [44].

We examined the potential side effects of PEP005 on the inflammatory cytokine expression as a possible consequence of increased CD69 production. It is well recognized that acutely or chronically HIV infected individuals seem to express higher levels of inflammatory cytokines including IL-6 and TNF-α in the peripheral blood [45-47]. Therefore, it is important that the agents for disrupting HIV latency do not exacerbate the unresolved chronic immune activation and inflammatory cytokine expression during HIV eradication interventions. To address this question, we examined CD4+ T cells purified from PBMCs of healthy HIV-negative donors ex vivo for pro-inflammatory cytokine expression following stimulation with PEP005 for 24 or 72 hours. The expression levels of TNF-α, IFN-γ, IL-2, and IL-6 cytokines were determined by RT-qPCR (FIGS. 6A-D). There was no significant increase in the expression of these cytokines, except for TNF-α that showed a tendency towards an up-regulation. However, the increase was not statistically significant.

Figure 7:
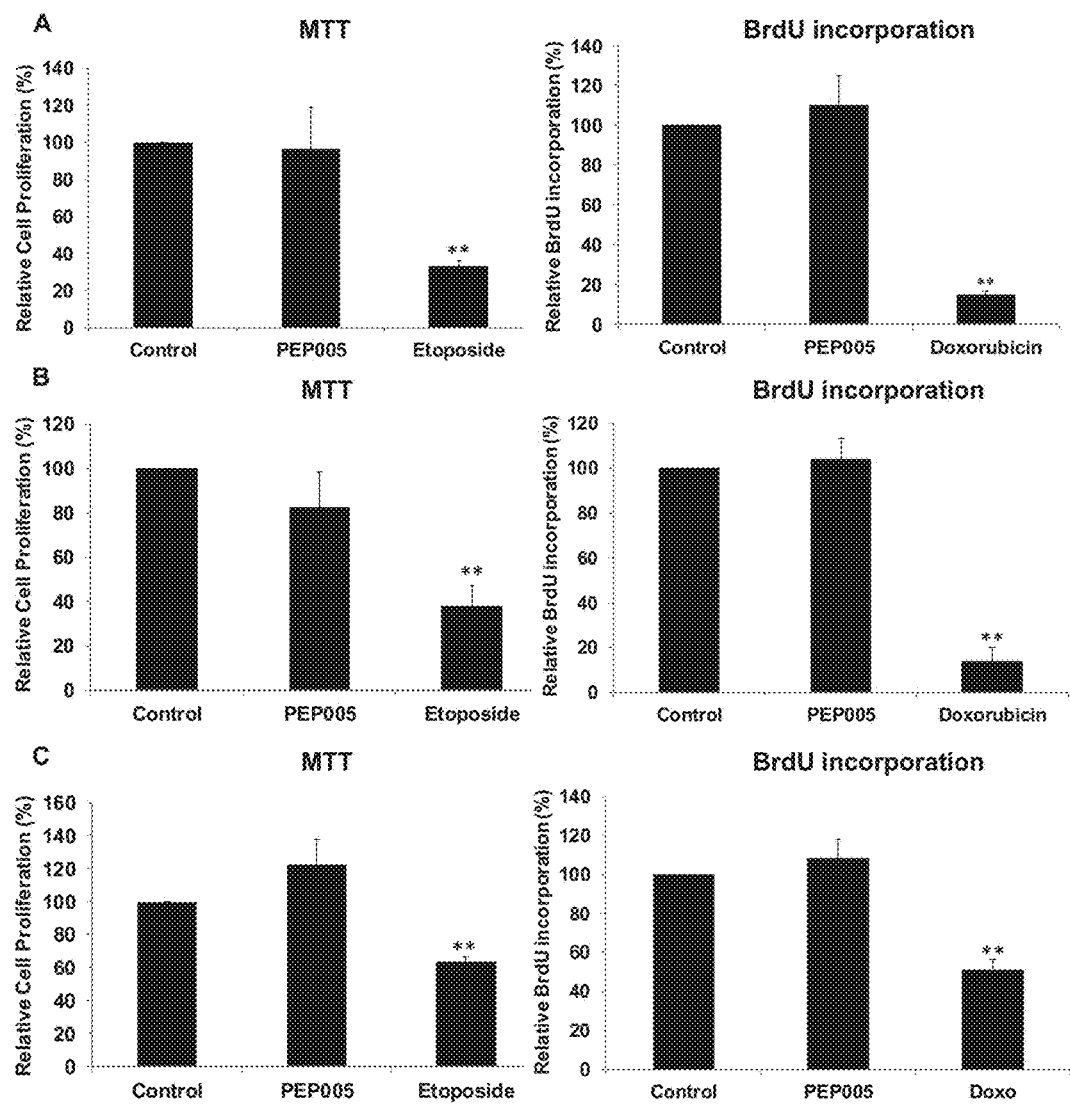
FIG. 7: PEP005 causes minimal cytotoxicity and T cell proliferation. To evaluate the impact of PEP005 on the cell viability, U1 cells (A), J-Lat A1 cells (B) and CD4+ T cells (C) were treated with 12 nM of PEP005 for 24 hours, the cell viability was examined with the MTT assay and the S-phase cell cycle progression was evaluated after BrdU incorporation using BrdU ELISA. 25-50 µM Etoposide or 100-150 µM Doxorubicin (Doxo) served as positive controls for MTT and BrdU assays respectively [48-50]. Statistical analysis was performed in comparison with controls. **, $p<0.01$.

In order to further evaluate the effects of PEP005 on T cell activation, we determined the ability of PEP005 to induce T cell proliferation and cytotoxicity using BrdU incorporation and MTT assays. PEP005 induced minimal levels of cellular toxicity in both J-Lat A1 and U1 cell lines, as well as in primary CD4+ T cells from peripheral blood samples of healthy HIV-negative donors (FIG. 7). Importantly, PEP005 treatment did not induce any significant increase in the proportion of cells in S-phase with J-Lat A1 cells, U1 cells or primary CD4+ T cells. In summary, despite the increased CD69 expression, minimal to no induction was found for the expression of pro-inflammatory cytokines and no significant impact was seen on cell cycling, indicating that PEP005 is a potential LRA candidate for evaluation in vivo.

PEP005 Induces Latent HIV Expression in Primary CD4+ T Cells Ex Vivo from Individuals with Suppressive ART.

Figure 8:
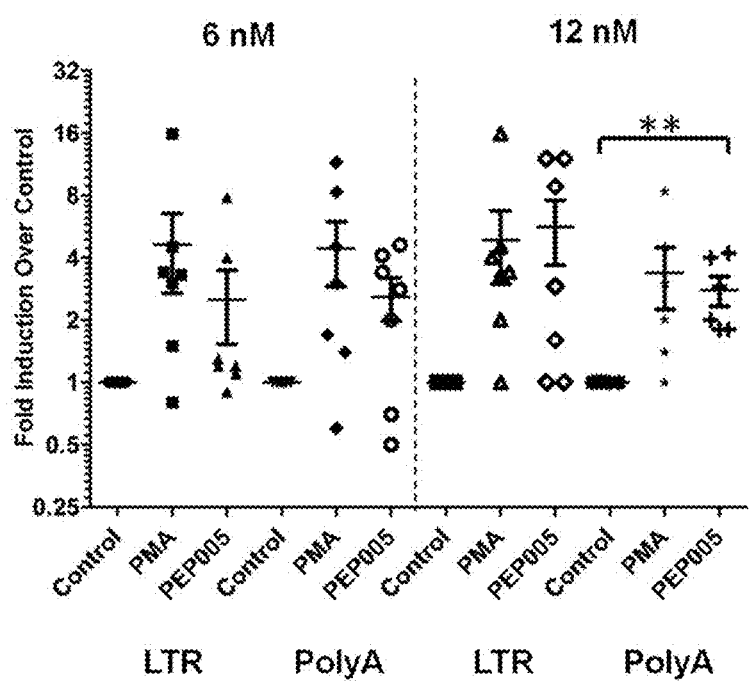
FIG. 8: PEP005 induces full-length HIV transcripts in primary CD4+ T cells from HIV infected individuals on suppressive ART. Primary CD4+ T cells were isolated from peripheral blood of HIV infected individuals on suppressive ART and treated with 6 or 12 nM PEP005, 200 ng/ml PMA plus 2 µM Ionomycin, or DMSO for 6 hours. Induction of HIV transcription was measured using RT-qPCR for the 5' LTR region or Poly A region of the virus. **, $p<0.01$.

We examined the ability of PEP005 to induce latent HIV expression in primary CD4+ T cells from HIV infected individuals under suppressive ART. The viral loads were below 20 copies/ml of plasma and the CD4+ T cell counts ranged from 260 to 1100 (Table 1). Two different doses (6 nM and 12 nM) of PEP005 were added for 6 hrs to purified primary CD4+ T cells from the peripheral blood of these individuals. The level of HIV mRNA expression was measured by RT-qPCR with primers/probe specific for the HIV 5' LTR region. The magnitude of induction of HIV RNA transcription by PMA we observed in this study differs somewhat from earlier studies [51] because of differences in experimental design (shorter incubation times, PMA concentration) as well as the inherent variability of responses of latently infected primary CD4+ T cells to LRAs. At 6 nM, PEP005 induced an increase in HIV transcription in 2 out of 7 individuals; at 12 nM, HIV transcription was observed in 5 out of 7 individuals (FIG. 8). To verify the capacity of PEP005 to reactivate latent HIV to produce full-length transcripts, RT-qPCR was performed using the primers/probe targeting HIV 3' polyadenylation (poly A) region [26]. After 6 hours of PEP005 treatment, 5 of the 7 donors had 2 fold or >2 fold increase in full-length HIV transcripts, while 5 of the 6 donors showed 2 or >2 fold increase after 12 nM of treatment. These results indicate that PEP005 is effective in reactivating transcription of HIV from latently infected cells ex vivo (FIG. 8). A higher dose of PEP005 is expected to induce more potent reactivation of latent HIV from patient samples.

HIV Induction in Primary CD4+ T Cells from HIV Infected Individuals on ART is Enhanced by the Combination of PEP005 with JQ1.

Figure 2:
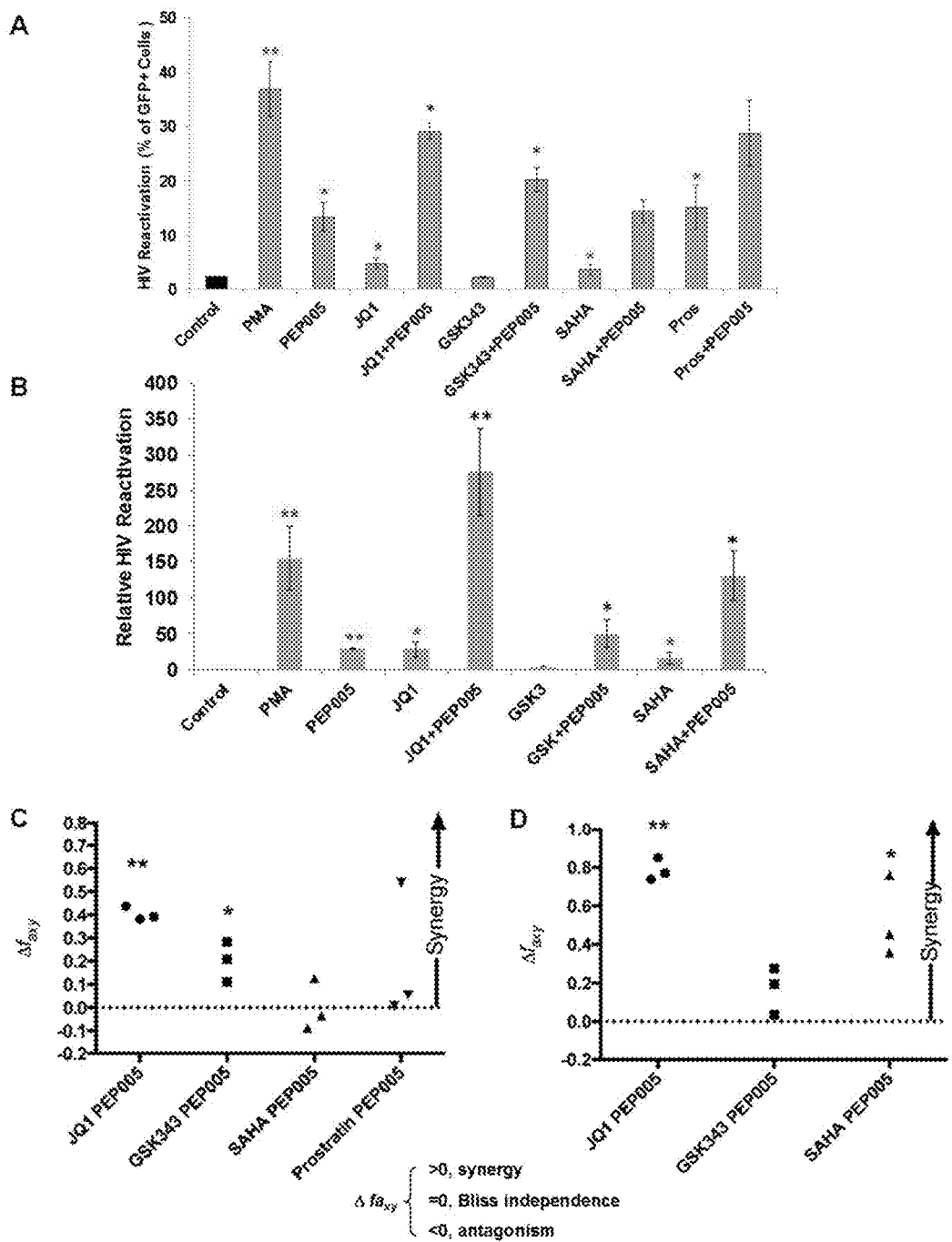
FIG. 2: PEP005 synergizes with other latency reversing agents in reactivating latent HIV. (A) J-Lat A1 cells were treated with 5 ng/ml PMA, 6 nM PEP005, 500 nM SAHA, 2 µM JQ1, 2 µM GSK343, or 10 µM Prostratin alone or in combination with 6 nM PEP005 for 24 hours and the percentage of GFP expressing cells was determined using flow cytometry. **, $p<0.01$; *, $p<0.05$ compared with control treatment; **, $p<0.01$; *, $p<0.05$ compared with PEP005 treatment alone. (B) The U1 cells were treated with 5 ng/ml PMA, 6 nM PEP005, 500 nM SAHA, 2 µM JQ1, or 2 µM GSK343, alone or in combination with 6 nM PEP005 for 24 hours and the HIV transcription was evaluated using RT-qPCR. Numbers indicate fold-increase over the control. **, $p<0.01$; *, $p<0.05$ compared with control treatment; **, $p<0.01$; *, $p<0.05$ compared with PEP005 treatment alone. (C and D) PEP005 synergizes with other LRAs to significantly increase GFP or HIV-1 mRNA expression in J-Lat A1 (C) or U1 (D) cell lines. The Bliss independence model was utilized for calculation of synergy for LRA combinations [35]. Dotted horizontal line signifies pure additive effect ($\Delta f_{axy}=0$). Synergy is defined as $\Delta f_{axy}>0$ while $\Delta f_{axy}<0$ indicates antagonism. Statistical significance was determined using a one tailed ratio t-test comparing predicted and observed drug combination effects. *$p<0.05$; **$p<0.01$.
Figure 9:
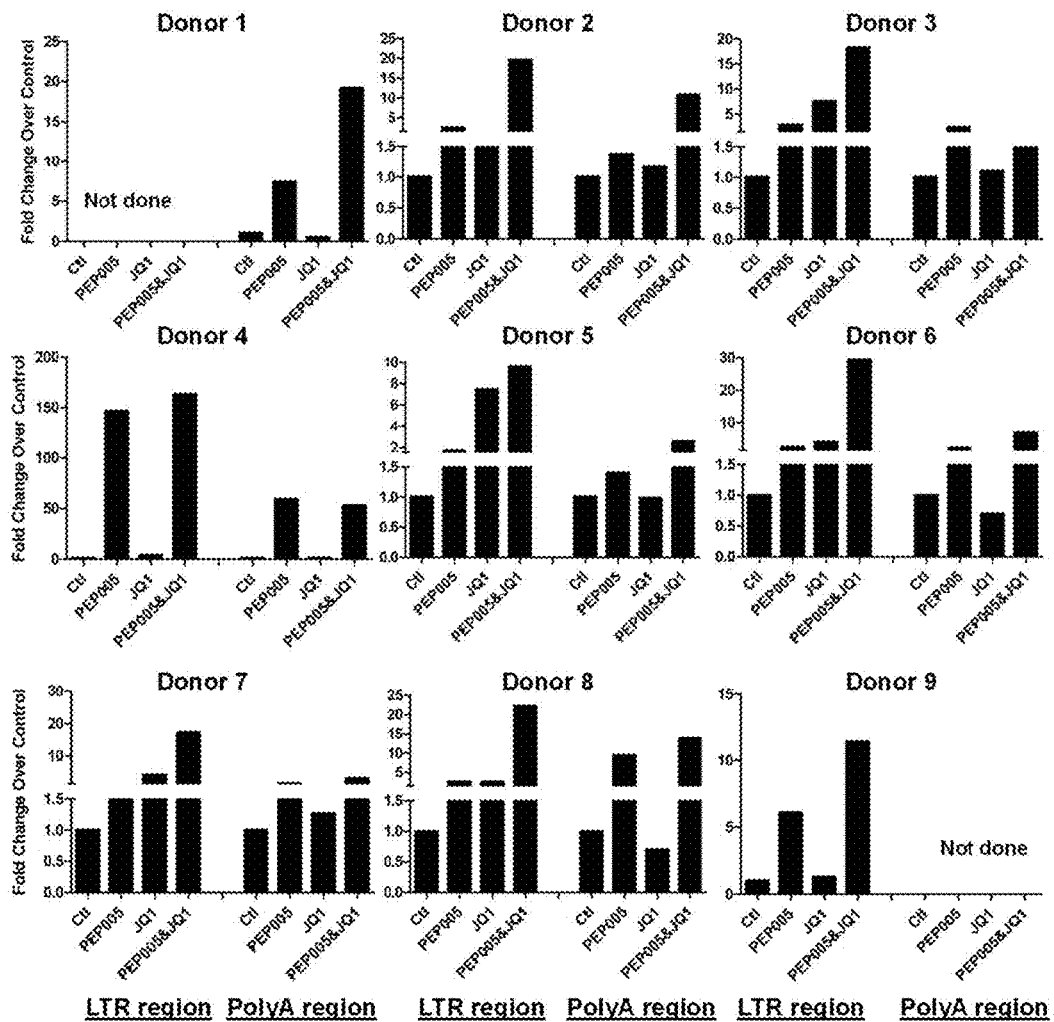
FIG. 9: PEP005 and JQ1 synergistically induce HIV transcription 6 hrs after treatment in primary CD4+ T cells from HIV infected individuals on suppressive ART. Primary CD4+ T cells were isolated from the peripheral blood of HIV positive individuals on suppressive ART and treated with 12 nM PEP005 alone or in combination with JQ1 for 6 hours, and HIV transcription was quantified using RT-qPCR for the 5' LTR region or Poly A region of the virus. The amount of cDNA was only enough to amplify either Poly A region or LTR region during PCR in donor 1 and donor 9.
Figure 10:
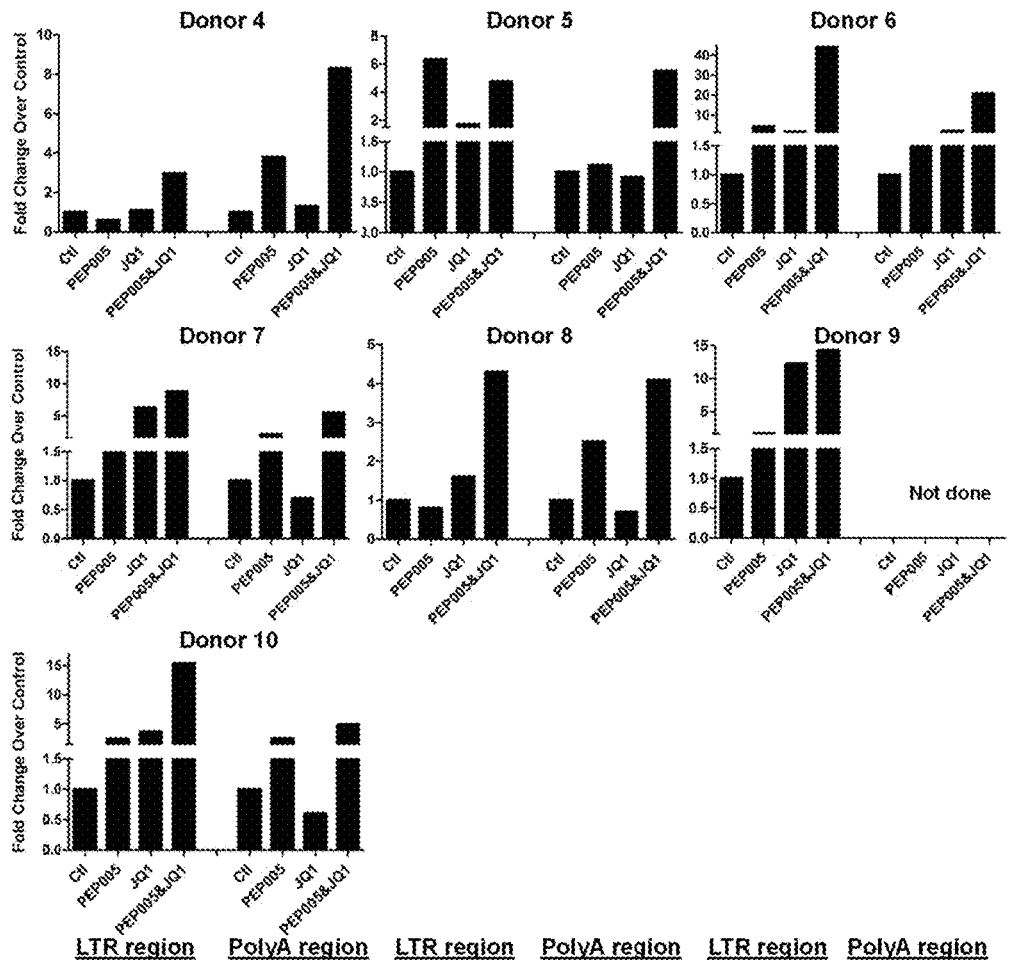
FIG. 10: PEP005 and JQ1 synergistically induce HIV transcription 48 hrs after treatment in primary CD4+ T cells from HIV infected individuals on suppressive ART. Primary CD4+ T cells were isolated from the peripheral blood of HIV positive individuals on suppressive ART and treated with 12 nM PEP005 alone or in combination with JQ1 for 48 hours, and HIV transcription was quantified using RT-qPCR for the 5' LTR region or Poly A region of the virus. The amount of cDNA was only enough to amplify LTR region during PCR in donor 9.
Figure 11:
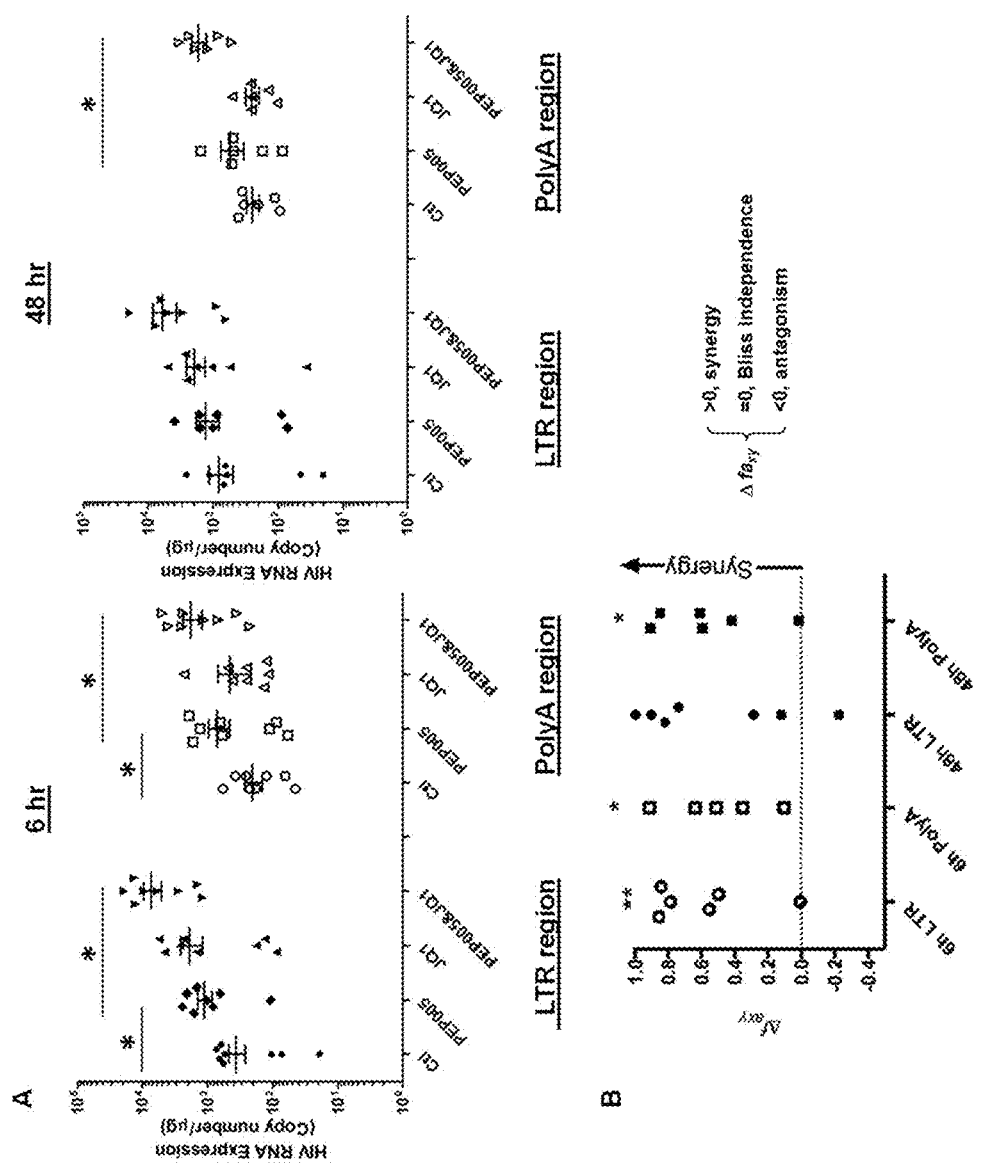
FIG. 11: PEP005 and JQ1 synergistically induce HIV transcription in primary CD4+ T cells from HIV infected individuals on suppressive ART. Primary CD4+ T cells were isolated from the peripheral blood of HIV positive individuals on suppressive ART and treated with 12 nM PEP005 alone or in combination with JQ1 for 6 or 48 hours, and HIV transcription was quantified using RT-qPCR for the 5' LTR region or Poly A region of the virus. (A) Copy number of HIV RNA in one μg total RNA in the primary CD4+ T cells after reactivation with 12 nM PEP005. *, p<0.05. (B) PEP005 synergizes with JQ1 to significantly increase HIV mRNA expression in primary CD4+ T cells isolated from patients under suppressive ART. The Bliss independence model was utilized for calculation of synergy for LRA combinations [35]. Dotted horizontal line signifies pure additive effect ($\Delta f_{axy}=0$). For these analyses, we included all data for which every parameter for the synergy analysis was available and excluded individual cases where the parameters were not met. Synergy is defined as $\Delta f_{axy}>0$ while $\Delta f_{axy}<0$ indicates antagonism. Statistical significance was determined using a one tailed paired ratio t-test comparing predicted and observed drug combination effects. *p<0.05; **p<0.01.

Our data showed that PEP005 used in combination with JQ1 resulted in synergistic reactivation of HIV expression in both the J-Lat A1 cells and the U1 cell models of HIV latency in vitro (FIG. 2). This prompted us to examine whether the combination of JQ1 and PEP005 would significantly enhance the ex vivo induction of latent HIV expression in primary CD4+ T cells from HIV infected individuals on suppressive ART. HIV transcription was measured by RT-qPCR following the treatment of cells with 12 nM PEP005 alone, 2 μM JQ1 alone, or 12 nM PEP005 plus 2 μM JQ1 for 6 hrs or 48 hrs. After 6 hrs of stimulation, a strong combined effect of PEP005 and JQ1 induced transcription of HIV RNA using 5' LTR assay was seen in CD4+ T cell samples from all individuals except one. When transcripts were measured with assay for the HIV poly A region, an enhanced combination effect was seen in 6 of 8 HIV infected individuals. In donor 1 and donor 9, the amount of cDNA was only sufficient to measure HIV RNA with either the Poly A region or LTR region assay (FIG. 9). The combination treatment at 48 hrs was similarly more potent compared to PEP005 treatment alone in 6 of 7 patient samples when assessed by assay of HIV 5' LTR region (up to 10 fold increase) and in all 6 patient samples by assay of the Poly A region of the HIV genome (1.6 to 14 fold increase). In donor 9, the amount of cDNA was only sufficient for the Poly A region assay (FIG. 10). When analyzed as HIV RNA copy number in 1 μg of total RNA from CD4+ T cells, PEP005 significantly induced latent HIV reactivation compared with control treatment after 6 hr incubation, and combined treatment of PEP005 with JQ1 further significantly induced full-length latent HIV reactivation compared with PEP005 treatment alone after 6 or 48 hr incubation (*, p<0.05; ** p<0.01, FIG. 11A). Applying the Bliss independence model for combined drug effects, criteria for synergistic ex vivo reactivation of full length latent HIV transcription by PEP005 and JQ1 were met with the caveat that this assessment does not determine whether these viral transcripts were translated into viral proteins of viral particles (FIG. 11B).

Taken together, PEP005 exerted a synergistic effect with JQ1 on reactivation of HIV transcription from latency in both cell line models and from CD4+ T cells obtained from patients on suppressive ART that included expression of fully elongated and processed HIV RNAs.

PEP005 Down-Regulates Cell Surface Expression of HIV Receptors on Primary CD4+ T Cells.

Figure 12:
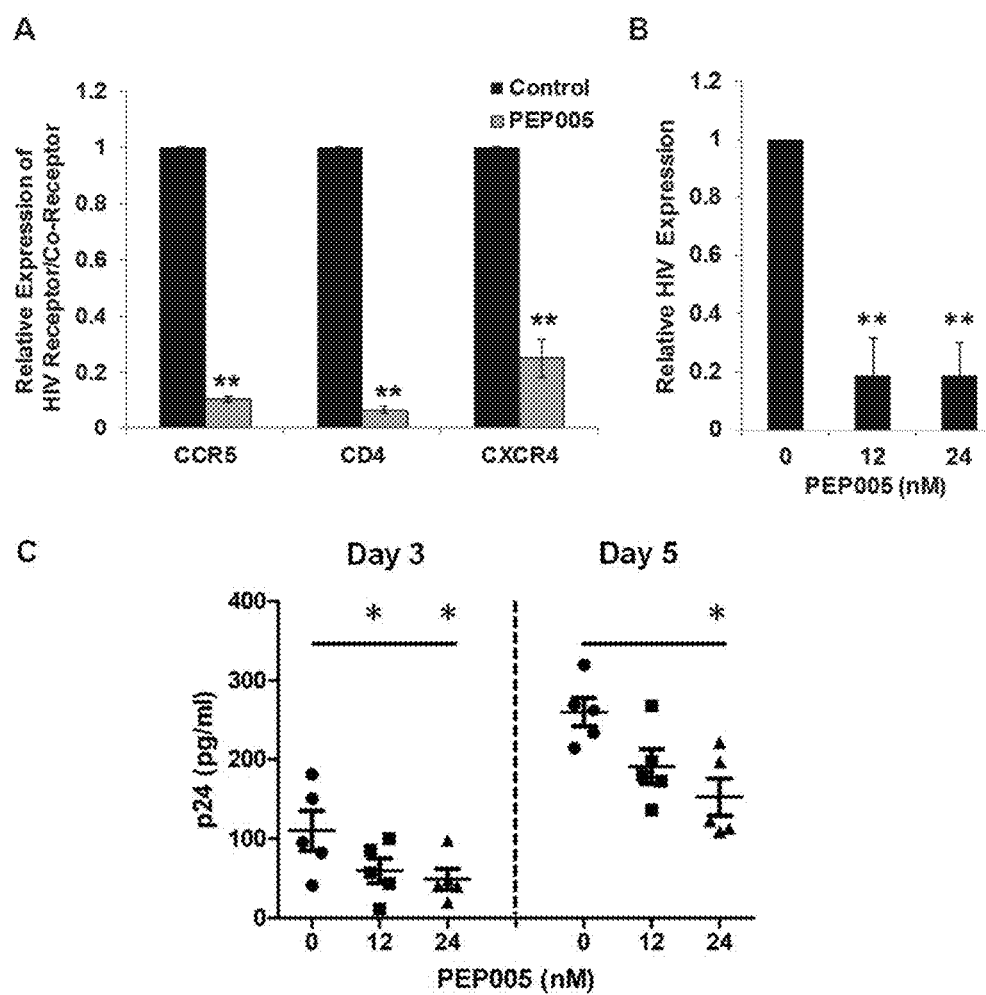
FIG. 12: PEP005 down-modulates the expression of CD4, CCR5 and CXCR4 and inhibits HIV infection of primary CD4+ T cells ex vivo. (A) PEP005 inhibits expression of HIV receptors/co-receptors. The CD4+ T cells were isolated from the peripheral blood of HIV-negative uninfected controls and treated with 12 nM PEP005 for 72 hours. The expression of CD4, CCR5 and CXCR4 genes was evaluated using RT-qPCR after normalizing for GAPDH. (B) and (C) PEP005 inhibits HIV infection of primary CD4+ T cells ex vivo. Primary CD4+ T cells were pre-treated with 12 or 24 nM PEP005 overnight and infected with the virus. The CD4+ T cells were incubated for 5 days without PEP005. The cells were collected for RT-qPCR targeting the HIV LTR region (B), or supernatants were collected for p24 ELISA (C). *, p<0.05; **, p<0.01.

Recent studies have shown that Prostratin and analogs down-modulate HIV receptor/co-receptor expression, which could have protective effects against the viral infection [52,53]. Conversely, SAHA, known to induce latent HIV expression in HIV infected individuals receiving ART, was reported to increase susceptibility of naive CD4+ T cells to HIV acquisition [54]. Diterpene compounds are known to inhibit expression of HIV receptors/co-receptors including CD4, CCR5, and CXCR4, which are important for the viral attachment and entry into immune cells [27, 52, 53, 55, 56]. We sought to examine the effect of PEP005 on the cell surface expression of HIV receptors and co-receptors in CD4+ T cells. Primary CD4+ T cells from peripheral blood samples of healthy HIV-negative donors were treated with 12 nM PEP005 and evaluated for the expression levels of CD4, CCR5, and CCXR4 using RT-qPCR. Our data showed that PEP005 treatment caused a significant reduction in the expression of all these HIV receptors/co-receptors, indicating that PEP005 may not pose the risk of increasing susceptibility of CD4+ T cells to HIV infection during its reactivation of HIV latency (FIG. 12A). Instead, PEP005 contributed to suppression of propagating HIV infection of CD4+ T cells following the reactivation of latent HIV. To investigate the potentially protective effects of PEP005, primary CD4+ T cells were infected with HIV with or without pre-treatment of 12 or 24 nM PEP005 for 24 hrs. The virological outcome in the CD4+ T cell cultures in vitro was monitored for 5 days. We observed that PEP005 dampened HIV gene expression as well as decreased the level of viral replication as determined at 3 and 5 days after HIV infection of primary CD4+ T cells (FIGS. 12B and 12C). These findings demonstrate that PEP005 prevents HIV infection of naive CD4+ T cells through down-modulation of HIV co-receptor expression (CD4, CXCR4 and CCR5), which is beneficial during the process of latent HIV reactivation.

DISCUSSION

Since the discovery of stable, latent viral reservoirs in HIV-infected individuals in spite of long-term suppressive ART, several studies have been performed to better understand the mechanisms of the establishment of HIV latency as well as to identify crucial steps for the maintenance of the viral latency [5,6,21]. The identification of memory CD4+ T cells, mostly central memory CD4+ T cells, as the major viral reservoir has provided clues for designing novel strategies for HIV eradication [5,57]. Accordingly, a "shock and kill" strategy was proposed to eradicate latent HIV reservoirs [6]. Diterpene compounds are among the potential candidates for disrupting HIV latency. They are more potent than several other LRAs in inducing latent HIV expression in multiple HIV latency models including in vitro J-Lat cell lines, primary CD4+ T cell based cell cultures, and resting CD4+ T cells from the peripheral blood of HIV infected individuals [20,24]. Diterpenes can down-modulate the expression of cell surface receptors that are known to mediate HIV attachment and entry and can potentially prevent the spread of viral infection to bystander CD4+ T cells [27, 52-54]. Therefore, it is useful to identify diterpene compounds suitable for HIV cure studies that could reactivate HIV from the latent reservoirs with low to minimal cytotoxicity while preventing new viral infections of CD4+ T cells.

The data from this study show, for the first time, that PEP005, a diterpene compound, can effectively reactivate latent HIV expression in vitro and ex vivo. It has been reported that an ingenol ester, IngB, is also able to reactivate HIV from latency [24,27]. Both of these compounds showed efficacy in reactivation of HIV latency at low nanomolar levels without exerting apparent cytotoxicity. IngB could induce increased levels of protein expression of NF-κB and P-TEFb, IFNγ [24,27], while PEP005 does not increase NF-κB protein expression levels. Activation of NF-κB and P-TEFb is essential for HIV reactivation from latency. However, excessive induction of these proteins may potentially be problematic because NF-κB is a master regulator for multiple signaling pathways, and P-TEFb is a general activator of transcriptional elongation, that also contributes to multiple signaling pathways [58,59]. Further studies are warranted to investigate whether IngB or PEP005 alone can induce protein expression of NF-κB or P-TEFb in resting CD4+ T cells, and not just in proliferating CD4+ T cells. Thirdly, IngB induced IFNγprotein expression [24,27], while PEP005 barely caused any increase in this or other inflammatory cytokine expression.

Although PEP005 shares a similar core structure with IngB, its C3 side chain structure is different and quite distinct from IngB (FIG. 1). Substitution of the C3-ester by different aliphatic and aromatic side chains confer markedly different biological properties [60,61], so it is likely that differences in molecular mechanisms of action and different T cell activation properties between PEP005 and Ingenol B are conferred by the structural differences of the C3-R. Consequently, PEP005 may offer several advantages over IngB. High levels of ingenols, up to 20 μM, induced NF-κB-independent cell death in Jurkat cells [62]. This concentration is about 1000-fold higher than the PEP005 concentrations used in this study, indicating that low concentrations of PEP005 capable of HIV reactivation may trigger signaling pathways differently and result in its low-to-minimal cytotoxicity. Therefore, the use of PEP005 at low concentrations for reactivation of latent HIV is important to minimize cytotoxic effects.

In the recently FDA-approved drug PICATO, PEP005 is the only active component with PKC agonist activity. Pharmacokinetic studies of PEP005 have been performed in small animals in vivo. Similar to the safety of the topical application of PICATO, the systemic (intravenous) use of PEP005 in small animals (mini pig and rat model) was reported to be relatively safe, with the maximum nonlethal dose >73 μg/kg (See, Assessment report of PICATO to European Medicines Agency, Sep. 20, 2012). These data support the use of PEP005 in HIV cure studies.

Since multiple molecular signaling pathways are involved in establishment and maintenance of HIV latency, a single LRA may not be adequate to achieve disruption of the multi-pronged regulatory mechanisms promoting HIV latency. SAHA, an HDAC inhibitor, shows some ability to reactivate HIV. However, the efficacy of SAHA varies among HIV infected individuals indicating that SAHA alone may not be sufficient for effective reactivation of latent HIV for all HIV infected individuals [16,17,63]. Therefore, a combination of compounds should be explored to induce viral expression from latently infected cells [43]. Our data show that PEP005 alone potently reactivates latent HIV expression in vitro. However, a combination of PEP005 and JQ1 was substantially more effective in inducing latent HIV in J-Lat A1 cells or U1 cells and in ex vivo primary CD4+ T cells from infected patients receiving suppressive ART. This could be attributed to potentiating effects of the PKC-NF-κB pathway on p-TEFb mechanism for reactivating. The range of drug concentrations that provides the best drug synergy using PEP005 can be determined [64].

Synergistic reactivation of latent HIV is also achieved by combining JQ1 with other ingenol compounds, as it has been observed that JQ1 boosted the reversal of HIV latency by IngB in J-Lat A1 cells [24]. However, it is not known whether this combined treatment leads to a synergistic effect on HIV expression in patient cells under ART ex vivo. Recently, Sillicano and colleagues showed that PKC agonists, such as Prostratin or Bryostatin 1, had a synergistic effect with JQ1 on the reactivation latent HIV ex vivo [35]. It was intriguing to note that GSK343, an EZH2 inhibitor, had no capacity to reactivate latent HIV by itself, but displayed increased potency in combination with PEP005 in J-Lat A1 cells. These observations are complemented by a study showing that GSK343 boosts SAHA or JQ1 reactivation of latent HIV in a primary resting T-cell model of HIV latency [65]. These findings indicate that pre-disruption of methylation of histone tails may facilitate efficient reactivation of latent HIV in combination with a second LRA.

PEP005 displayed potent activity to reactivate HIV from latency, producing polyadenylated viral transcripts while exerting minimal to low cytotoxicity and in the absence of major global T cell activation. Until now, only Bryostatin and PMA have been shown to stimulate comparable transcription of polyadenylated HIV RNA in primary CD4+ T cells isolated from HIV infected individuals on suppressive ART [26]. Considering that PEP005 had a similar capacity as PMA to reactivate latent HIV both in vitro and ex vivo (FIG. 1D and FIG. 8), and that PEP005 could induce GFP protein expression in J-Lat A1 cells (FIG. 1), PEP005 is useful for inducing HIV virus expression in vivo. There was an indication that PEP005 up-regulated TNFα to some extent, but these effects were not significantly different compared to controls. Similar to what is found with other PKC agonists, PEP005-induced NF-κB activation leads to increased expression of CD69 since its promoter contains multiple NF-κB binding sites [44]. However, it was interesting to note that cell proliferation was not significantly altered in J-Lat A1, U1 cells or primary CD4+ T cells, and inflammatory cytokine expression was not significantly enhanced by PEP005. These findings indicate that modulation of some of the T-cell activation markers may not necessarily lead to global T-cell activation. It has also been proposed that a low level of T cell activation may be required for efficient reactivation of HIV latency [26]. The ability of PEP005 to reduce cell surface expression of CD4, CCR5, and CXCR4 on T cells directly impacts susceptibility of primary CD4+ T cells to in vitro HIV infection. This supports the concept that reactivation of latent HIV by PEP005 may block viral spread to uninfected bystander CD4+ T cells, making it an attractive compound for advancing to clinical HIV cure studies. This study demonstrates that ingenols, including PEP005, represent a new group of compounds for combating HIV latency for viral eradication.

XI. References

1. Finzi D, Hermankova M, Pierson T, Carruth L M, Buck C, et al. (1997) Identification of a reservoir for HIV-1 in patients on highly active antiretroviral therapy. Science 278: 1295-1300.
2. Siliciano J D, Kajdas J, Finzi D, Quinn T C, Chadwick K, et al. (2003) Long-term follow-up studies confirm the stability of the latent reservoir for HIV-1 in resting CD4+ T cells. Nat Med 9: 727-728.
3. Wong J K, Hezareh M, Gunthard H F, Havlir D V, Ignacio C C, et al. (1997) Recovery of replication-competent HIV despite prolonged suppression of plasma viremia. Science 278: 1291-1295.
4. Chun T W, Stuyver L, Mizell S B, Ehler L A, Mican J A, et al. (1997) Presence of an inducible HIV-1 latent reservoir during highly active antiretroviral therapy. Proc Natl Acad Sci USA 94: 13193-13197.
5. Chomont N, El-Far M, Ancuta P, Trautmann L, Procopio F A, et al. (2009) HIV reservoir size and persistence are driven by T cell survival and homeostatic proliferation. Nat Med 15: 893-900.
6. Richman D D, Margolis D M, Delaney M, Greene W C, Hazuda D, et al. (2009) The challenge of finding a cure for HIV infection. Science 323: 1304-1307.
7. Lerner P, Guadalupe M, Donovan R, Hung J, Flamm J, et al. (2011) The gut mucosal viral reservoir in HIV-infected patients is not the major source of rebound plasma viremia following interruption of highly active antiretroviral therapy. J Virol 85: 4772-4782.
8. Guadalupe M, Reay E, Sankaran S, Prindiville T, Flamm J, et al. (2003) Severe CD4+ T-cell depletion in gut lymphoid tissue during primary human immunodeficiency virus type 1 infection and substantial delay in restoration following highly active antiretroviral therapy. J Virol 77: 11708-11717.
9. Giacomet V, Trabattoni D, Zanchetta N, Biasin M, Gismondo M, et al. (2014) No cure of HIV infection in a child despite early treatment and apparent viral clearance. Lancet 384: 1320.
10. Hirao L A, Grishina I, Bourry O, Hu W K, Somrit M, et al. (2014) Early mucosal sensing of SIV infection by paneth cells induces IL-1beta production and initiates gut epithelial disruption. PLoS Pathog 10: e1004311.
11. Whitney J B, Hill A L, Sanisetty S, Penaloza-MacMaster P, Liu J, et al. (2014) Rapid seeding of the viral reservoir prior to SIV viraemia in rhesus monkeys. Nature.
12. Persaud D, Gay H, Ziemniak C, Chen Y H, Piatak M, Jr., et al. (2013) Absence of detectable HIV-1 viremia after treatment cessation in an infant. N Engl J Med 369: 1828-1835.
13. Shalit P (2014) Management of dyslipidemia in patients with human immunodeficiency virus. Rev Cardiovasc Med 15 Suppl 1: S38-46.
14. Freitas P, Carvalho D, Santos A C, Madureira A J, Martinez E, et al. (2014) Adipokines, hormones related to body composition, and insulin resistance in HIV fat redistribution syndrome. BMC Infect Dis 14: 347.
15. Nasi M, Pinti M, De Biasi S, Gibellini L, Ferraro D, et al. (2014) Aging with HIV infection: A journey to the center of inflammAIDS, immunosenescence and neuroHIV. Immunol Lett.
16. Archin N M, Liberty A L, Kashuba A D, Choudhary S K, Kuruc J D, et al. (2012) Administration of vorinostat disrupts HIV-1 latency in patients on antiretroviral therapy. Nature 487: 482-485.
17. Elliott J H, Wightman F, Solomon A, Ghneim K, Ahlers J, et al. (2014) Activation of HIV transcription with short-course vorinostat in HIV-infected patients on suppressive antiretroviral therapy. PLoS Pathog 10: e1004473.
18. Rasmussen T A, Schmeltz Sogaard O, Brinkmann C, Wightman F, Lewin S R, et al. (2013) Comparison of HDAC inhibitors in clinical development: effect on HIV production in latently infected cells and T-cell activation. Hum Vaccin Immunother 9: 993-1001.
19. Shan L, Deng K, Shroff N S, Durand C M, Rabi S A, et al. (2012) Stimulation of HIV-1-specific cytolytic T lymphocytes facilitates elimination of latent viral reservoir after virus reactivation. Immunity 36: 491-501.
20. Spina C A, Anderson J, Archin N M, Bosque A, Chan J, et al. (2013) An in-depth comparison of latent HIV-1 reactivation in multiple cell model systems and resting CD4+ T cells from aviremic patients. PLoS Pathog 9: e1003834.
21. Jiang G, Espeseth A, Hazuda D J, Margolis D M (2007) c-Myc and Sp1 contribute to proviral latency by recruiting histone deacetylase 1 to the human immunodeficiency virus type 1 promoter. J Virol 81: 10914-10923.
22. Jiang G, Dandekar S (2014) Targeting NF-kappaB signaling with protein kinase C agonists as an emerging strategy for combating HIV latency. AIDS Res Hum Retroviruses.
23. Beans E J, Fournogerakis D, Gauntlett C, Heumann L V, Kramer R, et al. (2013) Highly potent, synthetically accessible prostratin analogs induce latent HIV expression in vitro and ex vivo. Proc Natl Acad Sci USA 110: 11698-11703.
24. Jiang G, Mendes E A, Kaiser P, Sankaran-Walters S, Tang Y, et al. (2014) Reactivation of HIV latency by a newly modified Ingenol derivative via protein kinase Cdelta-NF-kappaB signaling. AIDS.
25. Huang L, Ho P, Yu J, Zhu L, Lee K H, et al. (2011) Picomolar dichotomous activity of gnidimacrin against HIV-1. PLoS One 6: e26677.
26. Bullen C K, Laird G M, Durand C M, Siliciano J D, Siliciano R F (2014) New ex vivo approaches distinguish effective and ineffective single agents for reversing HIV-1 latency in vivo. Nat Med 20: 425-429.
27. Abreu C M, Price S L, Shirk E N, Cunha R D, Pianowski L F, et al. (2014) Dual role of novel ingenol derivatives from *Euphorbia tirucalli* in HIV replication: inhibition of de novo infection and activation of viral LTR. PLoS One 9: e97257.
28. Pandelo Jose D, Bartholomeeusen K, da Cunha R D, Abreu C M, Glinski J, et al. (2014) Reactivation of latent HIV-1 by new semi-synthetic ingenol esters. Virology 462-463C: 328-339.
29. Fidler B, Goldberg T (2014) Ingenol mebutate gel (picato): a novel agent for the treatment of actinic keratoses. P T 39: 40-46.
30. Warrilow D, Gardner J, Darnell G A, Suhrbier A, Harrich D (2006) HIV type 1 inhibition by protein kinase C modulatory compounds. AIDS Res Hum Retroviruses 22: 854-864.
31. Emiliani S, Fischle W, Ott M, Van Lint C, Amella C A, et al. (1998) Mutations in the tat gene are responsible for human immunodeficiency virus type 1 postintegration latency in the U1 cell line. J Virol 72: 1666-1670.
32. Jordan A, Bisgrove D, Verdin E (2003) HIV reproducibly establishes a latent infection after acute infection of T cells in vitro. EMBO J 22: 1868-1877.
33. Kumar A M, Borodowsky I, Fernandez B, Gonzalez L, Kumar M (2007) Human immunodeficiency virus type 1 RNA Levels in different regions of human brain: quantification using real-time reverse transcriptase-polymerase chain reaction. J Neurovirol 13: 210-224.
34. Shan L, Rabi S A, Laird G M, Eisele E E, Zhang H, et al. (2013) A novel PCR assay for quantification of HIV-1 RNA. J Virol 87: 6521-6525.
35. Laird G M, Bullen C K, Rosenbloom D I, Martin A R, Hill A L, et al. (2015) Ex vivo analysis identifies effective HIV-1 latency-reversing drug combinations. J Clin Invest.
36. Bliss C I (1939) The toxicity of poisons applied jointly. Annals of Applied Biology 26: 585-615.
37. Jiang G, Sancar A (2006) Recruitment of DNA damage checkpoint proteins to damage in transcribed and non-transcribed sequences. Mol Cell Biol 26: 39-49.
38. Tang Y, George A, Nouvet F, Sweet S, Emeagwali N, et al. (2014) Infection of female primary lower genital tract epithelial cells after natural pseudotyping of HIV-1: possible implications for sexual transmission of HIV-1. PLoS One 9: e101367.
39. Lavigne M, Eskeland R, Azebi S, Saint-Andre V, Jang S M, et al. (2009) Interaction of HP1 and Brg1/Brm with the globular domain of histone H3 is required for HP1-mediated repression. PLoS Genet 5: e1000769.
40. Friedman J, Cho W K, Chu C K, Keedy K S, Archin N M, et al. (2011) Epigenetic silencing of HIV-1 by the histone H3 lysine 27 methyltransferase enhancer of Zeste 2. J Virol 85: 9078-9089.
41. Verma S K, Tian X, LaFrance L V, Duquenne C, Suarez D P, et al. (2012) Identification of Potent, Selective, Cell-Active Inhibitors of the Histone Lysine Methyltransferase EZH2. ACS Med Chem Lett 3: 1091-1096.
42. Amatangelo M D, Garipov A, Li H, Conejo-Garcia J R, Speicher D W, et al. (2013) Three-dimensional culture sensitizes epithelial ovarian cancer cells to EZH2 methyltransferase inhibition. Cell Cycle 12: 2113-2119.
43. Margolis D M, Hazuda D J (2013) Combined approaches for HIV cure. Curr Opin HIV AIDS 8: 230-235.
44. Lopez-Cabrera M, Munoz E, Blazquez M V, Ursa M A, Santis A G, et al. (1995) Transcriptional regulation of the gene encoding the human C-type lectin leukocyte receptor AIM/CD69 and functional characterization of its tumor necrosis factor-alpha-responsive elements. J Biol Chem 270: 21545-21551.
45. Stacey A R, Norris P J, Qin L, Haygreen E A, Taylor E, et al. (2009) Induction of a striking systemic cytokine cascade prior to peak viremia in acute human immunodeficiency virus type 1 infection, in contrast to more modest and delayed responses in acute hepatitis B and C virus infections. J Virol 83: 3719-3733.
46. Macal M, Sankaran S, Chun T W, Reay E, Flamm J, et al. (2008) Effective CD4+ T-cell restoration in gut-associated lymphoid tissue of HIV-infected patients is associated with enhanced Th17 cells and polyfunctional HIV-specific T-cell responses. Mucosal Immunol 1: 475-488.
47. Guadalupe M, Sankaran S, George M D, Reay E, Verhoeven D, et al. (2006) Viral suppression and immune restoration in the gastrointestinal mucosa of human immunodeficiency virus type 1-infected patients initiating therapy during primary or chronic infection. J Virol 80: 8236-8247.
48. Don A S, Martinez-Lamenca C, Webb W R, Proia R L, Roberts E, et al. (2007) Essential requirement for sphingosine kinase 2 in a sphingolipid apoptosis pathway activated by FTY720 analogues. J Biol Chem 282: 15833-15842.
49. Ferreira P M, Lima D J, Debiasi B W, Soares B M, Machado Kda C, et al. (2013) Antiproliferative activity of *Rhinella marina* and *Rhaebo guttatus* venom extracts from Southern Amazon. Toxicon 72: 43-51.
50. Johnson T M, Meade K, Pathak N, Marques M R, Attardi L D (2008) Knockin mice expressing a chimeric p53

51. Ho Y C, Shan L, Hosmane N N, Wang J, Laskey S B, et al. (2013) Replication-competent noninduced proviruses in the latent reservoir increase barrier to HIV-1 cure. Cell 155: 540-551.
52. Kulkosky J, Culnan D M, Roman J, Dornadula G, Schnell M, et al. (2001) Prostratin: activation of latent HIV-1 expression suggests a potential inductive adjuvant therapy for HAART. Blood 98: 3006-3015.
53. Mehla R, Bivalkar-Mehla S, Zhang R, Handy I, Albrecht H, et al. (2010) Bryostatin modulates latent HIV-1 infection via PKC and AMPK signaling but inhibits acute infection in a receptor independent manner. PLoS One 5: e11160.
54. Lucera M, Tilton C A, Mao H, Dobrowolski C, Tabler C, et al. (2014) The histone deacetylase inhibitor vorinostat (SAHA) increases the susceptibility of uninfected CD4+ T cells to HIV by increasing the kinetics and efficiency of post-entry viral events. J Virol.
55. Kalinina O V, Pfeifer N, Lengauer T (2013) Modelling binding between CCR5 and CXCR4 receptors and their ligands suggests the surface electrostatic potential of the co-receptor to be a key player in the HIV-1 tropism. Retrovirology 10: 130.
56. Bedoya L M, Marquez N, Martinez N, Gutierrez-Eisman S, Alvarez A, et al. (2009) SJ23B, a jatrophane diterpene activates classical PKCs and displays strong activity against HIV in vitro. Biochem Pharmacol 77: 965-978.
57. Soriano-Sarabia N, Bateson R E, Dahl N P, Crooks A M, Kuruc J D, et al. (2014) The quantitation of replication-competent HIV-1 in populations of resting CD4+ T cells. J Virol.
58. Baldwin A S, Jr. (2001) Series introduction: the transcription factor NF-kappaB and human disease. J Clin Invest 107: 3-6.
59. Zhou Q, Li T, Price D H (2012) RNA polymerase II elongation control. Annu Rev Biochem 81: 119-143.
60. Liang X, Grue-Sorensen G, Mansson K, Vedso P, Soor A, et al. (2013) Syntheses, biological evaluation and SAR of ingenol mebutate analogues for treatment of actinic keratosis and non-melanoma skin cancer. Bioorg Med Chem Lett 23: 5624-5629.
61. Sorg B, Schmidt R, Hecker E (1987) Structure/activity relationships of polyfunctional diterpenes of the ingenane type. I. Tumor-promoting activity of homologous, aliphatic 3-esters of ingenol and of delta 7,8-isoingenol-3-tetradecanoate. Carcinogenesis 8: 1-4.
62. Blanco-Molina M, Tron G C, Macho A, Lucena C, Calzado M A, et al. (2001) Ingenol esters induce apoptosis in Jurkat cells through an AP-1 and NF-kappaB independent pathway. Chem Biol 8: 767-778.
63. Blazkova J, Chun T W, Belay B W, Murray D, Justement J S, et al. (2012) Effect of histone deacetylase inhibitors on HIV production in latently infected, resting CD4(+) T cells from infected individuals receiving effective antiretroviral therapy. J Infect Dis 206: 765-769.
64. Chou T C (2006) Theoretical basis, experimental design, and computerized simulation of synergism and antagonism in drug combination studies. Pharmacol Rev 58: 621-681.
65. Tripathy M K, McManamy M E, Burch B D, Archin N M, Margolis D M (2015) H3K27 demethylation at the proviral promoter sensitizes latent HIV to the effects of vorinostat in ex-vivo cultures of resting CD4+ T cells. J Virol.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A composition comprising ingenol-3-angelate (PEP005) and one or more additional latency reactivation agents, wherein PEP005 is present in an amount effective to synergistically enhance a therapeutic benefit of the one or more additional latency reactivation agents, wherein the therapeutic benefit comprises reactivation of a latent virus in a subject infected with the virus,
   wherein the one or more additional latency reactivation agents is a positive transcription elongation factor b activator, and
   wherein the virus is a human immunodeficiency virus (HIV).

2. The composition of claim 1, wherein the positive transcription elongation factor b activator is selected from the group consisting of JQ1, hexamethylene bisacetamide (HMBA), and combinations thereof.

3. The composition of claim 1, further comprising a viral therapeutic vaccine.

4. A method for reactivating a latent virus in a subject infected with the virus, the method comprising administering to the subject an effective amount of the composition of claim 1.

5. The method of claim 4, wherein the amount of the ingenol-3-angelate (PEP005) is an amount that is capable of inducing RNA transcription from the latent virus in an infected cell from the subject.

6. The method of claim 4, wherein the amount of the ingenol-3-angelate (PEP005) is an amount that displays low to minimal cytotoxicity without inducing global T cell activation.

7. The method of claim 4, wherein the amount of the ingenol-3-angelate (PEP005) is an amount that suppresses or prevents the reactivated latent virus from infecting uninfected CD4+ T cells in the subject.

8. The method of claim 4, wherein the positive transcription elongation factor b activator is selected from the group consisting of JQ1, hexamethylene bisacetamide (HMBA), and combinations thereof.

9. A kit comprising: (a) ingenol-3-angelate (PEP005); and (b) one or more additional latency reactivation agents, wherein PEP005 is present in an amount effective to synergistically enhance a therapeutic benefit of the one or more additional latency reactivation agents, wherein the therapeutic benefit comprises reactivation of a latent virus in a subject infected with the virus,
   wherein the one or more additional latency reactivation agents is a positive transcription elongation factor h activator, and
   wherein the virus is a human immunodeficiency virus (HIV).

* * * * *

UNITED STATES PATENT AND TRADEMARK OFFICE
CERTIFICATE OF CORRECTION

PATENT NO. : 10,376,486 B2
APPLICATION NO. : 15/426437
DATED : August 13, 2019
INVENTOR(S) : Guochun Jiang and Satya Dandekar Page 1 of 1

It is certified that error appears in the above-identified patent and that said Letters Patent is hereby corrected as shown below:

In the Claims

In Column 52, Lines 22-23 (Claim 9) delete "agents is a positive transcription elongation factor h activator, and" and enter --agents is a positive transcription elongation factor b activator, and--

Signed and Sealed this
Twenty-ninth Day of October, 2019

Andrei Iancu
*Director of the United States Patent and Trademark Office*